(12) United States Patent
Giobbi et al.

(10) Patent No.: US 8,508,336 B2
(45) Date of Patent: Aug. 13, 2013

(54) PROXIMITY-BASED HEALTHCARE MANAGEMENT SYSTEM WITH AUTOMATIC ACCESS TO PRIVATE INFORMATION

(75) Inventors: John Giobbi, Bend, OR (US); Ryan Gallivan, Bend, OR (US); Kent Yundt, Bend, OR (US)

(73) Assignee: Proxense, LLC, Bend, OR (US)

( * ) Notice: Subject to any disclaimer, the term of this patent is extended or adjusted under 35 U.S.C. 154(b) by 667 days.

(21) Appl. No.: 12/371,170

(22) Filed: Feb. 13, 2009

(65) Prior Publication Data

US 2009/0206992 A1    Aug. 20, 2009

Related U.S. Application Data

(60) Provisional application No. 61/028,847, filed on Feb. 14, 2008, provisional application No. 61/075,117, filed on Jun. 24, 2008, provisional application No. 61/090,243, filed on Aug. 20, 2008, provisional application No. 61/090,878, filed on Aug. 21, 2008, provisional application No. 61/102,987, filed on Oct. 6, 2008.

(51) Int. Cl.
    *G05B 19/00*    (2006.01)
(52) U.S. Cl.
    USPC ....... 340/5.81; 340/5.82; 340/5.83; 340/5.74; 705/2; 705/3; 235/382
(58) Field of Classification Search
    USPC ................. 340/5.81, 5.82, 5.83, 5.74; 705/2, 705/3; 235/382
    See application file for complete search history.

(56) References Cited

U.S. PATENT DOCUMENTS

| | | | | |
|---|---|---|---|---|
| 5,541,583 | A | * | 7/1996 | Mandelbaum ............. 340/10.51 |
| 6,040,786 | A | * | 3/2000 | Fujioka .......................... 340/928 |
| 6,325,285 | B1 | * | 12/2001 | Baratelli ........................ 235/380 |
| 6,633,981 | B1 | | 10/2003 | Davis |
| 7,676,380 | B2 | * | 3/2010 | Graves et al. ..................... 705/2 |
| 2002/0010679 | A1 | | 1/2002 | Felsher |
| 2003/0088441 | A1 | * | 5/2003 | McNerney ........................ 705/3 |

(Continued)

OTHER PUBLICATIONS

International Preliminary Report and Written Opinion of The International Searching Authority, Jul. 1, 2010, 8 pages.

(Continued)

*Primary Examiner* — Jennifer Mehmood
*Assistant Examiner* — Andrew Bee
(74) *Attorney, Agent, or Firm* — Patent Law Works LLP

(57) ABSTRACT

A healthcare management system and method provide efficient and secure access to private information. A portable physical device, referred to herein as a Personal Digital Key or "PDK", stores one or more profiles in memory. The biometric profile is acquired in a secure trusted process and is uniquely associated with an individual that is authorized to use and is associated with the PDK. The PDK can wirelessly transmit the identification information including a unique PDK identification number and the biometric profile over a secure wireless channel for use in an authentication process. The PDK is configured to wirelessly communicate with a reader. A provider interface coupled to the reader, and the reader is further configured to receive profile information from the PDK. The healthcare management system also includes an auto login server configured to communicate with the provider interface to allow access to information in a patient database.

17 Claims, 41 Drawing Sheets

(56) References Cited

U.S. PATENT DOCUMENTS

| | | | | |
|---|---|---|---|---|
| 2003/0137404 | A1 | 7/2003 | Bonneau et al. | |
| 2004/0128389 | A1 | 7/2004 | Kopchik | |
| 2004/0167465 | A1 | 8/2004 | Mihai et al. | |
| 2005/0005136 | A1* | 1/2005 | Chen et al. | 713/186 |
| 2005/0055242 | A1 | 3/2005 | Bello et al. | |
| 2005/0055244 | A1 | 3/2005 | Mullan et al. | |
| 2005/0114150 | A1* | 5/2005 | Franklin | 705/1 |
| 2005/0139656 | A1* | 6/2005 | Arnouse | 235/382 |
| 2005/0182661 | A1* | 8/2005 | Allard et al. | 705/3 |
| 2005/0187792 | A1* | 8/2005 | Harper | 705/2 |
| 2005/0216313 | A1* | 9/2005 | Claud et al. | 705/3 |
| 2006/0022042 | A1* | 2/2006 | Smets et al. | 235/451 |
| 2006/0074713 | A1* | 4/2006 | Conry et al. | 705/2 |
| 2006/0136742 | A1 | 6/2006 | Giobbi | |
| 2006/0144943 | A1* | 7/2006 | Kim | 235/451 |
| 2006/0229909 | A1* | 10/2006 | Kaila et al. | 705/2 |
| 2006/0273176 | A1* | 12/2006 | Audebert et al. | 235/451 |
| 2006/0279412 | A1 | 12/2006 | Holland et al. | |
| 2007/0005403 | A1* | 1/2007 | Kennedy et al. | 705/4 |
| 2007/0019845 | A1* | 1/2007 | Kato | 382/126 |
| 2007/0033072 | A1* | 2/2007 | Bildirici | 705/3 |
| 2007/0100939 | A1 | 5/2007 | Bagley | |
| 2007/0158411 | A1* | 7/2007 | Krieg | 235/380 |
| 2007/0159994 | A1 | 7/2007 | Brown et al. | |
| 2007/0204078 | A1 | 8/2007 | Boccon-Gibod et al. | |
| 2007/0245157 | A1 | 10/2007 | Giobbi | |
| 2007/0260888 | A1 | 11/2007 | Giobbi | |
| 2008/0071577 | A1* | 3/2008 | Highley | 705/3 |
| 2008/0129450 | A1 | 6/2008 | Riegebauer | 340/5.86 |
| 2008/0228524 | A1* | 9/2008 | Brown | 705/3 |
| 2008/0251579 | A1* | 10/2008 | Larsen | 235/380 |
| 2008/0316045 | A1* | 12/2008 | Sriharto et al. | 340/825.49 |
| 2009/0076849 | A1* | 3/2009 | Diller | 705/3 |

OTHER PUBLICATIONS

PCT International Search Report and Written Opinion, PCT/US09/34095, Mar. 25, 2009, 9 pages.

"File Security, Keychains, Encryption, and More with Mac OS X (10.3+)" (Apr. 4, 2005) by John Hendron; 30 pages; originally downloaded from http://www.johnhendron.net/documents/OSX_Security.pdf.

"Smart Card Setup Guide" (2006) by Apple et al.; 16 pages; originally downloaded from http://manuals.info.apple.com/en_US/Smart_Card_Setup_Guide.pdf.

PCT International Search Report and Written Opinion, PCT Application No. PCT/US08/87835, Feb. 11, 2009, 8 pages.

NPL "Imation USB 2.0 Micro Hard Drive" (Nov. 22, 2005) by Dan Costa; retrieved Mar. 11, 2013; converted to PDF originally from http://www.pcmag.com/article2/0,2817,1892209,00.asp; 1 pg.

"Automatically unlock PC when entering proximity" (Dec. 7, 2005) by bohrsatom et al.; retrieved Mar. 11, 2013; converted to PDF originally from http://www.salling.com/forums/viewtopic.php?t=3190; 5 pgs.

"SplashID—Secure Password Manager for PDAs and Smartphones" (Mar. 8, 2007) by SplashID; converted to PDF originally from http://www.splashdata.com/splashid/ via http://www.archive.org/; retrieved Mar. 11, 2013; 3 pgs.

"Automate proximity and location-based computer actions" (Jun. 5, 2007) by Adam Pash; retrieved Mar. 11, 2013; converted to PDF originally from http://lifehacker.com/265822/automate-proximity-and-location+based-computer-actions; 3 pgs.

NPL "magicJack: Could It Be the Asterisk Killer?" (Aug. 1, 2007) by Nerd Vittles; retrieved Mar. 11, 2013; converted to PDF originally from http://nerdvittles.com/index.php?p=187; 3 pgs.

NPL "BlueProximity—Leave it—it's locked, come back—it's back too . . . " (Aug. 26, 2007) by BlueProximity; converted to PDF originally from http://blueproximity.sourceforge.net/ via http://www.archive.org/; retrieved Mar. 11, 2013; 1 pg.

* cited by examiner

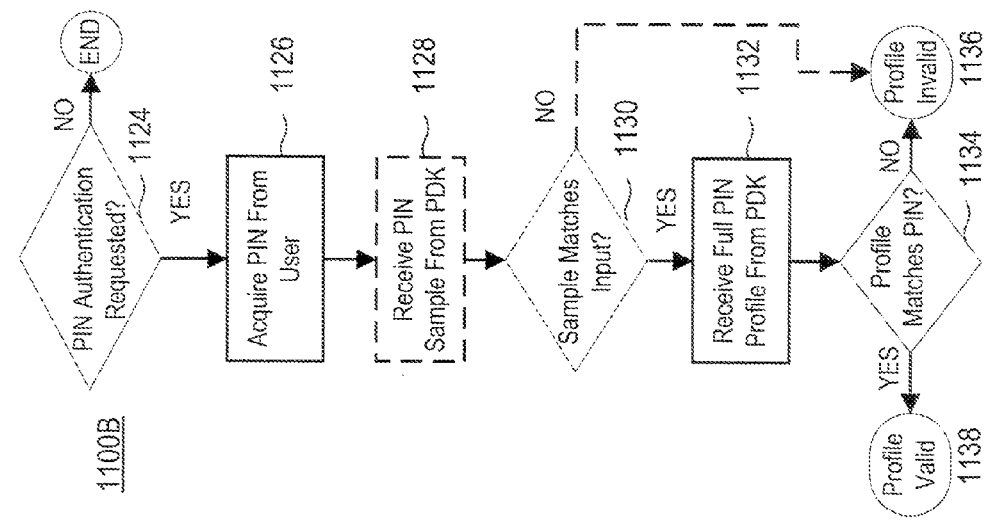

PROXIMITY-BASED HEALTHCARE MANAGEMENT SYSTEM WITH AUTOMATIC ACCESS TO PRIVATE INFORMATION

CROSS REFERENCE TO RELATED APPLICATIONS

This application claims the benefit of U.S. Patent Application No. 61/028,847, entitled "ProxMediSys" filed Feb. 14, 2008; U.S. Patent Application No. 61/075,117, entitled "ProxMed" filed Jun. 24, 2008; U.S. Patent Application No. 61/090,234, entitled "ProxMed" filed Aug. 20, 2008; U.S. Patent Application No. 61/090,878, entitled "ProxMed Integrated Proximity-Based Systems for Healthcare" filed Aug. 21, 2008; and U.S. Patent Application No. 61/102,987, entitled "ProxMed" filed Oct. 6, 2008, the entire contents of which are all incorporated herein by reference.

BACKGROUND OF THE INVENTION

1. Field of Art

This disclosure generally relates to the field of radio frequency identification (RFID) and electronic authentication, and more specifically, to systems and methods for automatic and secure authentication and identification for healthcare.

2. Description of the Related Art

Optimizing patient care is an ever-changing and challenging endeavor. Ensuring quality patient care that is safe, efficient and cost-effective is very important to patients, as well as healthcare providers. Conventional technologies used in the healthcare industry for aiding provider patient care, monitoring patient treatment, receiving and retrieving patient data and monitoring provider activity have not yet provided optimal features to meet these needs. Recently, software application systems have been developed in an attempt to improve patient care and provider performance.

These days, most healthcare facilities utilize electronic software and applications to securely store and efficiently access private patient information. In order to access the patient information, a patient must provide a certain amount of information at each provider visit. The information provided is an attempt to confirm the patient's identity and that the patient's current information is up to date. For example, each time a patient visits his or her doctor for a check-up, he or she typically walks up to the registration table and is greeted by a receptionist or other healthcare provider. The patient must then provide his or her name, the time of the appointment, and the name of the patient's doctor. Often, the receptionist or other healthcare provider must also confirm that the patient's insurance and address information in the system is still correct and up to date. Typically, the patient is then given a medical history form to complete. The patient typically completes a form while waiting for his or her appointment in the waiting room.

Yet another problem in the prior art is the management of and access to electronic records of patients. In most healthcare institutions, healthcare providers can gain access to a patient's electronic records with authorized entry into the healthcare software application system. In order to prove authorization, providers are equipped with a unique username and password. Each time a provider needs to access patient information, they must log in to the system using their unique name and password. Further, each time they are done accessing the electronic records, they must log out of the system to ensure that unauthorized use does not occur. The process of logging in and logging off each time may prove to be quite time-consuming given the number of patients a provider visits in a given day.

Another problem in the prior art is the utilization of equipment in medical facilities and making sure they are deployed in a matter that maximizes their usage and availability. For example, in many hospitals the location of equipment is not tracked and monitored other than by conducting an annual inventory of the equipment. Thus, the medical staff is not aware if some the equipment is not being used or located in an area where it is not required. Thus, tracking of the location of equipment continues to be a problem.

Another problem in the prior art is the monitoring of provider performance to ensure optimal quality patient care. Typically, in many healthcare facilities, an admitted patient is treated by multiple healthcare providers. During the patient's stay, the patient may be seen by multiple healthcare providers and each healthcare provider attends to the patient at multiple times during the day. Further, each provider treats multiple patients while on duty. Current healthcare software applications have been developed to help establish clear and consistent communication between the various providers and ensure optimal record keeping. Given these dynamics, monitoring provider performance and ensuring consistent, safe and effective patient care can be challenging.

Yet another problem in the prior art is the monitoring of patient health status, minimizing response time and ensuring effective and optimal patient care. For example, when a patient is resting in his or her room, she is monitored specialized equipment that is usually wired to a corresponding area of the patient's body. Therefore, the patient can only be monitored while the patient is in his or her hospital room. Further, information about the patient monitored is only displayed at the monitoring equipment itself, or at the nurse's station. These conditions present limitations on the effective monitoring of patients.

The above-defined issues represent serious impediments to quality patient care as well as increasing the cost and adding inefficiency to the delivery of medical services.

BRIEF SUMMARY OF THE INVENTION

A healthcare management system and method provide efficient and secure access to private information. A portable physical device, referred to herein as a Personal Digital Key or "PDK", stores one or more profiles (e.g., a biometric profile) in a tamper-proof memory. The biometric profile is acquired in a secure trusted process and is uniquely associated with an individual that is authorized to use and is associated with the PDK. The PDK can wirelessly transmit the identification information including a unique PDK identification number and the biometric profile over a secure wireless channel for use in an authentication process. The PDK is configured to wirelessly communicate with a reader. A provider interface coupled to the reader, and the reader is further configured to receive profile information from the PDK. The healthcare management system also includes an auto login server configured to communicate with the provider interface to allow access to information in a patient database.

Typically, the reader wirelessly receives the profile from the PDK in order to access private information. In one embodiment, the reader acquires a biometric input from the individual carrying the PDK at the point of request for access. The biometric input can be acquired by, for example, a fingerprint scan, iris scan, retinal scan, palm scan, face scan, DNA analysis, signature analysis, voice analysis or any other input mechanism that provides physical or behavioral characteristics uniquely associated with the individual. The reader compares the biometric profile received from the PDK to the biometric input obtained at the point of the request for access to determine if access should be authorized.

In one embodiment, the auto login server of the healthcare management system is configured to receive profile information from a second PDK while access for the first PDK is being allowed. The received profile information of the second PDK is associated with the first PDK.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

FIG. 11A is a flowchart illustrating one embodiment of a process for profile testing using a biometric input.

FIG. 11B is a flowchart illustrating one embodiment of a process for profile testing using a personal identification number.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Figure 1:
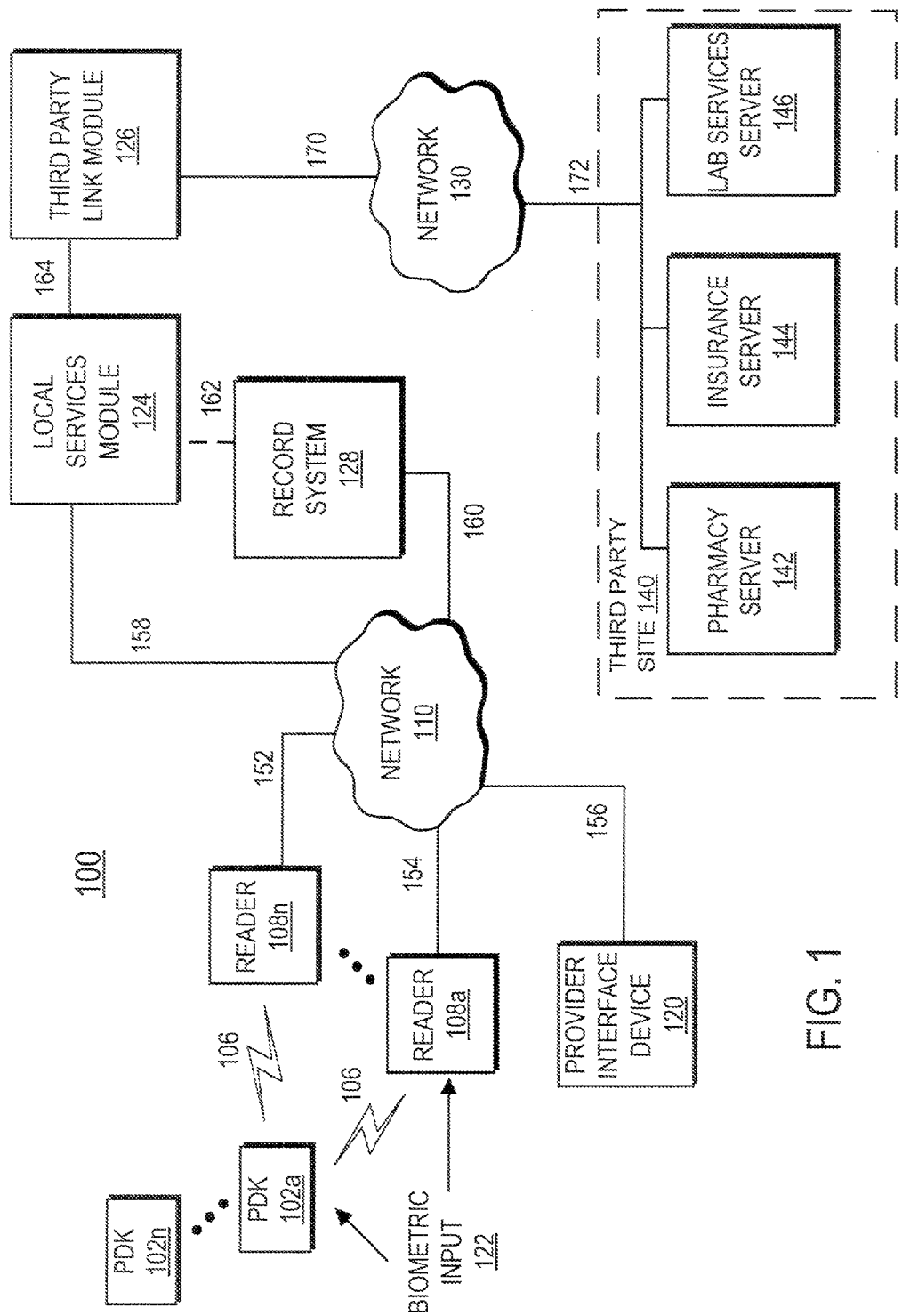
FIG. 1 is a high level block diagram illustrating a system for secure electronic authentication for medical services and applications.

FIG. 1 is a high level block diagram illustrating a system for securely authenticating an individual for transaction-processing and/or access control applications for medical services and applications. The system 100 comprises a Personal Digital Key (PDK) 102, a Reader 108, a network 110, a provider interface device 120, a local services module 124, a third party link module 126, a record system 128, a network 130 and a remote services site 140, which includes pharmacy services 142, insurance services 144 and lab services 146. The Reader 108 is coupled to PDK 102 by a wireless link 106 and coupled to a network 110 by either a wired or wireless link represented by lines 152 and 154. The Reader 108 is also adapted to receive a biometric input 122 from a user and is capable of displaying status to a user. The PDK 102 is also adapted to receive biometric input 122 from a user. The network 110 couples the local services module 124 and third party link module 126 to the Reader 108. The network 110 also couples the local servers 124 and third party link module 126 to the record system 128 via signal lines 158 and 160. In alternative embodiments, different or additional external services, registries or databases (not shown) are coupled to the network 110. In another embodiment, the Reader 108 operates as a standalone device without a connection to the network 110. The network 130 couples the third party link module 126 to the third party site 140 and associated third party services such as the pharmacy server 142, insurance server 144 and lab services server 146.

The system 100 addresses applications where it is important to ensure a specific individual is authorized to perform a given transaction. A transaction as used herein include executing a purchase or financial dealing, enabling access to physical and/or digital items, providing identification or personal information or executing other tasks where it is important to authenticate an individual for use. In one embodiment, the Reader 108 wirelessly receives information stored in the PDK 102 that uniquely identifies the PDK 102 and the individual carrying the PDK 102. In another embodiment, the Reader 108 can also receive a biometric input 122 from the individual. The PDK 102 can also receive biometric input 122 from the individual. Based on the received information, the Reader 108 determines if the transaction should be authorized. Beneficially, the system 100 provides comprehensive authentication without the need for PINs or passwords. Moreover, personal biometric information need not be stored in any local or remote storage database and is only stored on the user's own PDK. Furthermore, in one embodiment, purchase transactions can be efficiently completed without requiring the use of physical credit cards, tokens or other user action beyond initiating the transaction.

The PDK 102 is a compact, portable uniquely identifiable wireless device typically carried by an individual or affixed to an object or device. The PDK 102 stores digital information in a tamper-proof format that uniquely associates the PDK 102 with an individual. Example embodiments of PDKs are described in more detail in U.S. patent application Ser. No. 11/292,330, entitled "Personal Digital Key And Receiver/Decoder Circuit System And Method" filed on Nov. 30, 2005; U.S. patent application Ser. No. 11/620,581 entitled "Wireless Network Synchronization Of Cells And Client Devices On A Network" filed on Jan. 5, 2007; and U.S. patent application Ser. No. 11/620,577 entitled "Dynamic Real-Time Tiered Client Access" filed on Jan. 5, 2007, the entire contents of which are all incorporated herein by reference.

To establish the trust, credibility and confidence of the authentication system, information stored in the PDK 102 is acquired by a process that is trusted, audited and easily verified. The process is ensured by a trusted third-party system, referred to herein as a Notary, that administers the acquisition and storage of information in the PDK 102 according to defined security protocols. In one embodiment, the Notary is a system and/or a trusted individual that witnesses the acquisition and storage either in person or remotely. In another embodiment, the Notary comprises trusted hardware that administers the initialization process by an automated system. Thus, once initialized by the trusted process, the PDK 102 can prove that the information it stores is that of the individual. Example embodiments of the initialization process are described in U.S. patent application Ser. No. 11/744,832 to John Giobbi, et al., entitled "Personal Digital Key Initialization and Registration For Secure Transaction" filed on May 5, 2007, the entire contents of which are incorporated herein by reference.

The Reader 108 wirelessly communicates with the PDK 102 when the PDK 102 is within a proximity zone of the Reader 108. The proximity zone can be, for example, several meters in radius and can be adjusted dynamically by the Reader 108. Thus, in contrast to many conventional RF ID devices, the Reader 108 can detect and communicate with the PDK 102 without requiring the owner to remove the PDK 102 from his/her pocket, wallet, purse, etc. Generally, the Reader 108 receives uniquely identifying information from the PDK 102 and initiates an authentication process for the individual carrying the PDK 102. In one embodiment, the Reader 108 is adapted to receive a biometric input 122 from the individual. The biometric input 122 comprises a representation of physical or behavioral characteristics unique to the individual. For example, the biometric input 122 can include a fingerprint, a palm print, a retinal scan, an iris scan, a photograph, a signature, a voice sample or any other biometric information such as DNA, RNA or their derivatives that can uniquely identify the individual. The Reader 108 compares the biometric input 122 to information received from the PDK 102 to determine if a transaction should be authorized. Alternatively, the biometric input 122 can be obtained by a biometric reader 470 (FIG. 4) on the PDK 102 and transmitted to the Reader 108 for authentication. In additional alternative embodiment, some or all of the authentication process can be performed by the PDK 102 instead of the Reader 108.

Figure 2:
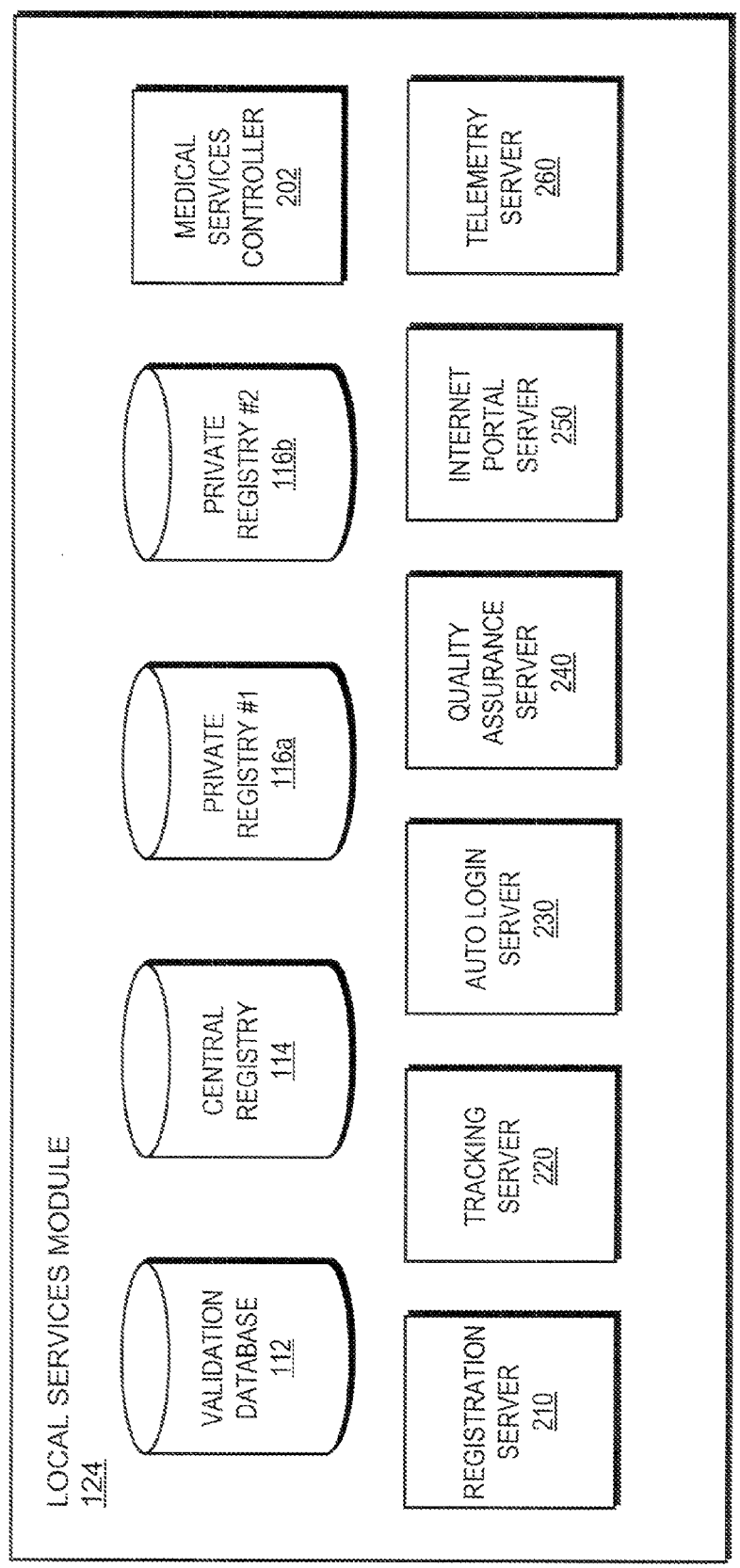
FIG. 2 is a block diagram illustrating one embodiment of a local services module.

The Reader 108 is further communicatively coupled to the network 110 in order to receive and/or transmit information to remote databases for remote authentication. In an alternative embodiment, the Reader 108 includes a non-volatile data storage that can be synchronized with one or more remote databases 112 or registries 114, 116*a*, 116*b* (FIG. 2). Such an embodiment alleviates the need for a continuous connection to the network 110 and allows the Reader 108 to operate in a standalone mode and for the local data storage to be updated when a connection is available. For example, a standalone Reader 108 can periodically download updated registry entries and perform authentication locally without any remote lookup.

The record system 128 stores complete personal health records of individuals. An example of a record system 128 is a server or servers of the Google™ Health website, provided by Google Inc. of Mountain View, Calif. and found at www.google.com/health. Another example of a record system 128 is the server or servers of the Microsoft™ HealthVault™, provided by Microsoft™ Corporation of Redmond, Wash. and found at www.healthvault.com.

The network 110 provides communication between the Reader 108 and the provider interface device 120, local services module 124, and third party link module 126. In alternative embodiments, one or more of these connections may not be present or different or additional network connections may be present. In one embodiment, the network 110 uses standard communications technologies and/or protocols. Thus, the network 110 can include links using technologies such as Ethernet, 802.11, 802.16, integrated services digital network (ISDN), digital subscriber line (DSL), asynchronous transfer mode (ATM), etc. Similarly, the networking protocols used on the network 110 can include the transmission control protocol/Internet protocol (TCP/IP), the hypertext transport protocol (HTTP), the simple mail transfer protocol (SMTP), the file transfer protocol (FTP), etc. The data exchanged over the network 110 can be represented using technologies and/or formats including the hypertext markup language (HTML), the extensible markup language (XML), etc. In addition, all or some of links can be encrypted using conventional encryption technologies such as the secure sockets layer (SSL), Secure HTTP and/or virtual private networks (VPNs). In another embodiment, the entities can use custom and/or dedicated data communications technologies instead of, or in addition to, the ones described above.

Similarly, the network 130 provides communication between the third party link module 126 and third party site 140. In alternative embodiments, one or more of these connections may not be present or different or additional network connections may be present. In one embodiment, the network 130 uses standard communications technologies and/or protocols. Thus, the network 130 can include links using technologies such as Ethernet, 802.11, 802.16, integrated services digital network (ISDN), digital subscriber line (DSL), asynchronous transfer mode (ATM), etc. Similarly, the networking protocols used on the network 110 can include the transmission control protocol/Internet protocol (TCP/IP), the hypertext transport protocol (HTTP), the simple mail transfer protocol (SMTP), the file transfer protocol (FTP), etc. The data exchanged over the network 110 can be represented using technologies and/or formats including the hypertext markup language (HTML), the extensible markup language (XML), etc. In addition, all or some of links can be encrypted using conventional encryption technologies such as the secure sockets layer (SSL), Secure HTTP and/or virtual private networks (VPNs). In another embodiment, the entities can use custom and/or dedicated data communications technologies instead of, or in addition to, the ones described above.

FIG. 2 is a block diagram illustrating a local services module 124, which includes one or more external databases including a validation database 112, a Central Registry 114 and one or more private registries 116a, 116b. The local services module 124 also includes a medical services controller 202, a registration server 210, a tracking server 220, an auto login server 230, a quality assurance server 240, and an internet portal server 250.

The validation database 112 stores additional information that may be used for authorizing a transaction to be processed at the Reader 108. For example, in purchase transactions, the validation database 112 is a credit card validation database that is separate from the merchant providing the sale. Alternatively, a different database may be used to validate different types of purchasing means such as a debit card, ATM card, or bank account number. As another example in healthcare systems, the validation database 112 is a medical record number validation database that separate from the healthcare institution providing the patient care, which provides confirmation of the patient's identification.

The registries 114, 116a, 116b are securely-accessible databases coupled to the network 110 that store, among other items, PDK, Notary, and Reader information. In one embodiment, the registries 114, 116a, 116b do not store biometric information. In an alternative embodiment, the registries 114, 116a, 116b store biometric information in an encoded format that can only be recovered using an algorithm or encoding key stored in the PDK 102. Information stored in the registries 114, 116a, 116b can be accessed by the Reader 108 via the network 110 for use in the authentication process. There are two basic types of registries 114, 116a, 116b illustrated: private registries 116a, 116b and the Central Registry 114. Private registries 116a, 116b are generally established and administered by their controlling entities (e.g., a health care provider, business authority, or other entity administering authentication). Private registries 116a, 116b can be custom configured to meet the specialized and independent needs of each controlling entity. The Central Registry 114 is a single highly-secured, centrally-located database administered by a trusted third-party organization. In one embodiment, all PDKs 102 are registered with the Central Registry 114 and may be optionally registered with one or more selected private registries 116a, 116b. In alternative embodiments, a different number or different types of registries 114, 116a, 116b may be coupled to the network 110.

The medical services controller 202 enables communication between the servers and modules of the local services module 124 and third party link module 126 with the provider interface device 120. In one embodiment, the medical services controller 202 receives information and requests from the provider interface device 120 via the network 110. In another embodiment, the medical services controller 202 coordinates the operation of the various servers and modules of the local services module 124 and third party link module 126. For example, when a patient registration request is received from the Reader 108, the medical services controller 202 routes the request to the registration server 210 and forwards registration confirmation to the appropriate destination, such as the provider interface device 120.

The registration server 210 automates the process of registering new patients and ensures that a patient never needs to register more than once. In one embodiment, the registration server 210 resides in the local services module 124, which is couple to the network via signal line 158. In one embodiment, the registration server 210 is coupled to the validation database 112, central registry 114 and private registries 116a, 116b. The registration server 210 receives patient registration requests from Readers 108 via the network 110 and sends information to the provider interface device 120 also via the network 110. One embodiment of the registration server 210 is described in more detail below with reference to FIG. 16.

The tracking server 220 enables real-time tracking of individuals, equipment and supplies. In one embodiment, the tracking server 220 resides in the local services module 124, which is coupled to the network 110 via signal line 158. The tracking server 220 receives information from the Readers 108 and sends information back to the Readers 108 and PDK 102. One embodiment of the tracking server 220 is described in more detail below with reference to FIG. 18.

The auto login server 230 allows for automated logging in of providers into the healthcare computer system. In one embodiment, the auto login server 230 resides in the local services module 124 and is coupled to the validation database 112, central registry 114 and private registries 116a, 116b. The auto login server receives login requests from the Readers 108 and sends login authorization to the provider interface device 120. One embodiment of the auto login server 230 is described in more detail below with reference to FIG. 20.

The quality assurance server 240 provides recommendations for improving patient care by monitoring treatment and provider activity. In one embodiment, the quality assurance server 240 resides in the local services module. The quality assurance server 240 receives information from the Readers 108 and sends information to the PDK 102 via the Readers 108. The quality assurance server 240 also sends information to the provider interface device 120. The quality assurance server 240 also determines provider salary adjustments by monitoring provider activity. One embodiment of the quality assurance server 240 is described in more detail below with reference to FIG. 22.

The internet portal server 250 provides a consistent interface to the third party link module 126. In one embodiment, the internet portal server 250 resides in the local services module 124. The internet portal server 250 is coupled to the third party link module 126 to allow communication between the third party link module 126 and related third party services, and local services module 124 and provider interface device 120. One embodiment of the internet portal server 250 is described in more detail below with reference to FIG. 24. Such third party services may include accessing a patient's virtual database records or insurance information or sending prescription requests to remote pharmacies. More detailed information describing the components and functions of these servers is described in more detail below.

The telemetry server 260 provides automatic updates and alerts for monitored patients. The telemetry server 260 receives information from Readers 108 and sends information to the provider interface device 120. In one embodiment, the telemetry server 260 resides in the local services module 124. One embodiment of the telemetry server 260 is described in more detail below with reference to FIG. 36.

Figure 3:
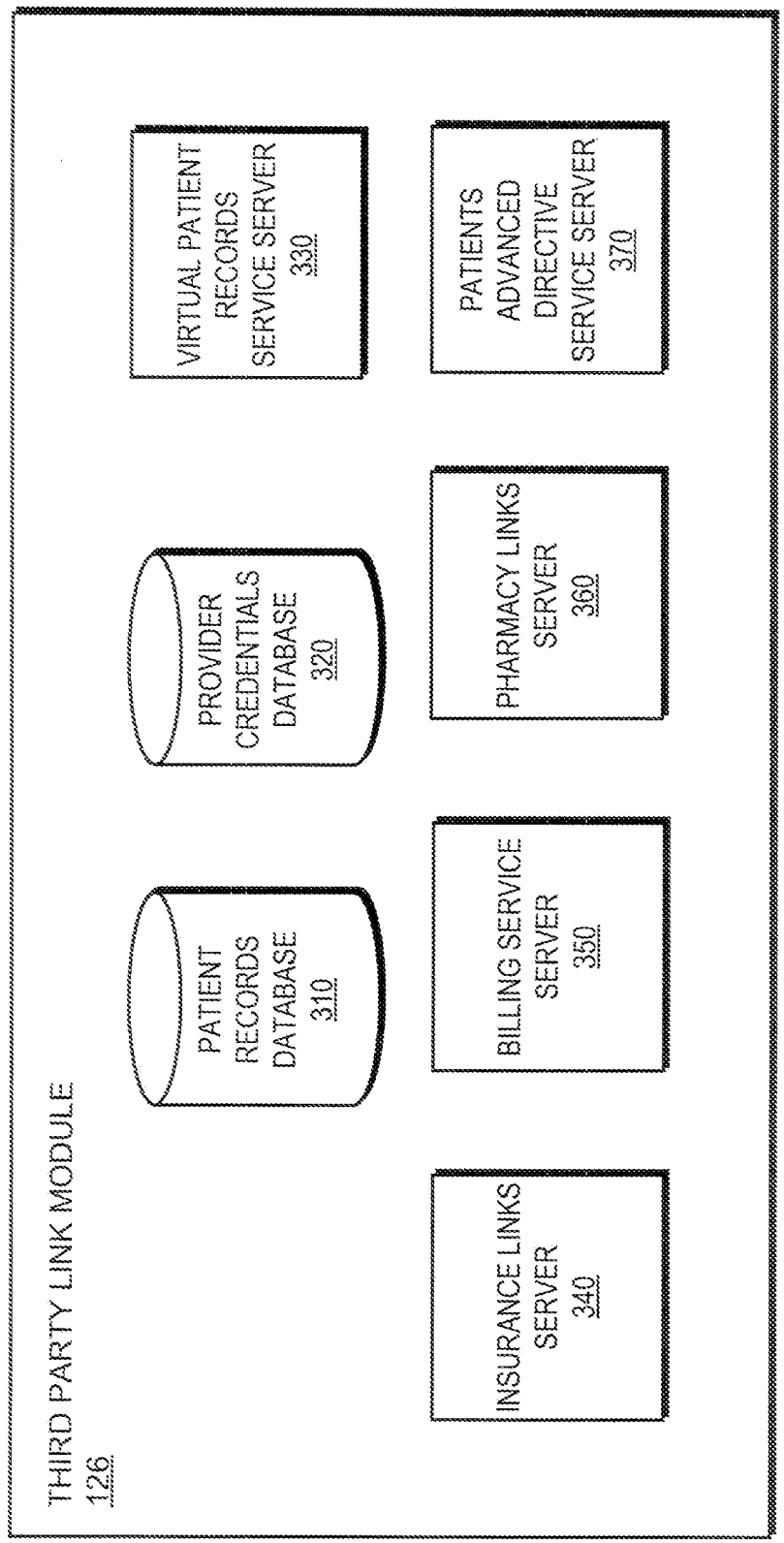
FIG. 3 is a block diagram illustrating one embodiment of a third party link module.

FIG. 3 is a block diagram illustrating a third party link module 126, which includes a patient records database 310, a provider credentials database 320, a virtual patient records service server 330, an insurance links server 340, a billing service server 350, a pharmacy links server 360 and a patient's advanced directive service server 370.

The patient records database 310 stores private patient information. Such information includes a patient's name, medical record number, address, insurance information, prescribed medication, medical and personal history, family information and picture as well as other information related to the patient's health. The patient records database 310 receives requests for patient information and sends patient data to the requesting entity. In one embodiment, the patient records database 310 resides in the third party link module 126 and is coupled to some or all of the modules within the third party link module 126.

The provider credentials database 320 stores information identifying provider information. Such information includes the provider's name, employee number, license number and picture, as well as other information unique to the specific provider. The provider credentials database 320 receives provider authentication requests from the Readers 108 and 720 and sends authentication confirmation to the provider interface device 120. In one embodiment, the provider credentials database 320 resides in the third party link module 126 and is coupled to some or all of the modules within the third party link module 126.

The virtual patient records service server 330 provides a virtual database of a complete record of a patient's medical files by automatically creating links to participating providers' records and enabling centralized and automated access to those records. The virtual patient records service server 330 receives requests for patient information from the provider interface device 120 and retrieves information from the record system 128. In one embodiment, the virtual patient records service server 330 receives request for patient information from the provider interface device 120 via the network 110 and signal lines 156, 158 and retrieves information from the record system 128 via signal line 162. In one embodiment, the record system 128 resides within the local services module 124 and the virtual patient records service server 330 retrieves information from the record system 128 via signal line 164. One embodiment of the virtual patient records service server 330 is described in more detail below with reference to FIG. 26.

The insurance links server 340 provides a portal of communication between the providers and patients' insurance providers and acts in conjunction with the billing services server 350 to update and report patients' billing statements. In one embodiment, the insurance links server 340 resides in the third party link module 126 and is coupled to and communicates with the insurance server 144 to send requests to and receive information from the insurance server 144. The insurance links server 340 is also coupled to the billing services server 350. In one embodiment, the insurance link server 340 is coupled to the internet portal server 250 and communicates with the provider interface device 120 via the internet portal server 250. One embodiment of the insurance links server 340 is described in more detail below with reference to FIG. 28.

The billing service server 350 works in cooperation with the insurance link sever 340 to update patient billing information. In one embodiment, the billing service server 350 resides in the third party link module 126 and is coupled to the insurance links server 340 and patient records database 310. The billing services server receives insurance information from the insurance links server 340 and sends billing information to the patient records database 310. One embodiment of the billing service server 350 is described in more detail below with reference to FIG. 30.

The pharmacy links server 360 provides a portal of communication between health care providers and patients pharmacies. In one embodiment, the pharmacy links server 360 resides in the third party link module 126 is coupled to and communicates with the pharmacy server 142 to send requests to and receive information from the pharmacy server 142. In one embodiment, the pharmacy links server 360 is coupled to the internet portal server 250 and communicates with the provider interface device 120 via the internet portal server 250. One embodiment of the pharmacy links server 360 is described in more detail below with reference to FIG. 32.

The patient's advanced directive service server 370 provides storage for and secure access to patients' advanced directives. An advanced directive is a legal document that allows a person to convey their decisions about end-of-life care. In one embodiment, the patient's advanced directive service server 370 resides in the third party link module 126. The patient's advanced directive service server 370 receives requests from and sends retrieved documents to the provider interface device 120. One embodiment of the patient's advanced directive service server 370 is described in more detail below with reference to FIG. 34. More detailed information describing the components and functions of the aforementioned servers is described in more detail below.

Figure 4:
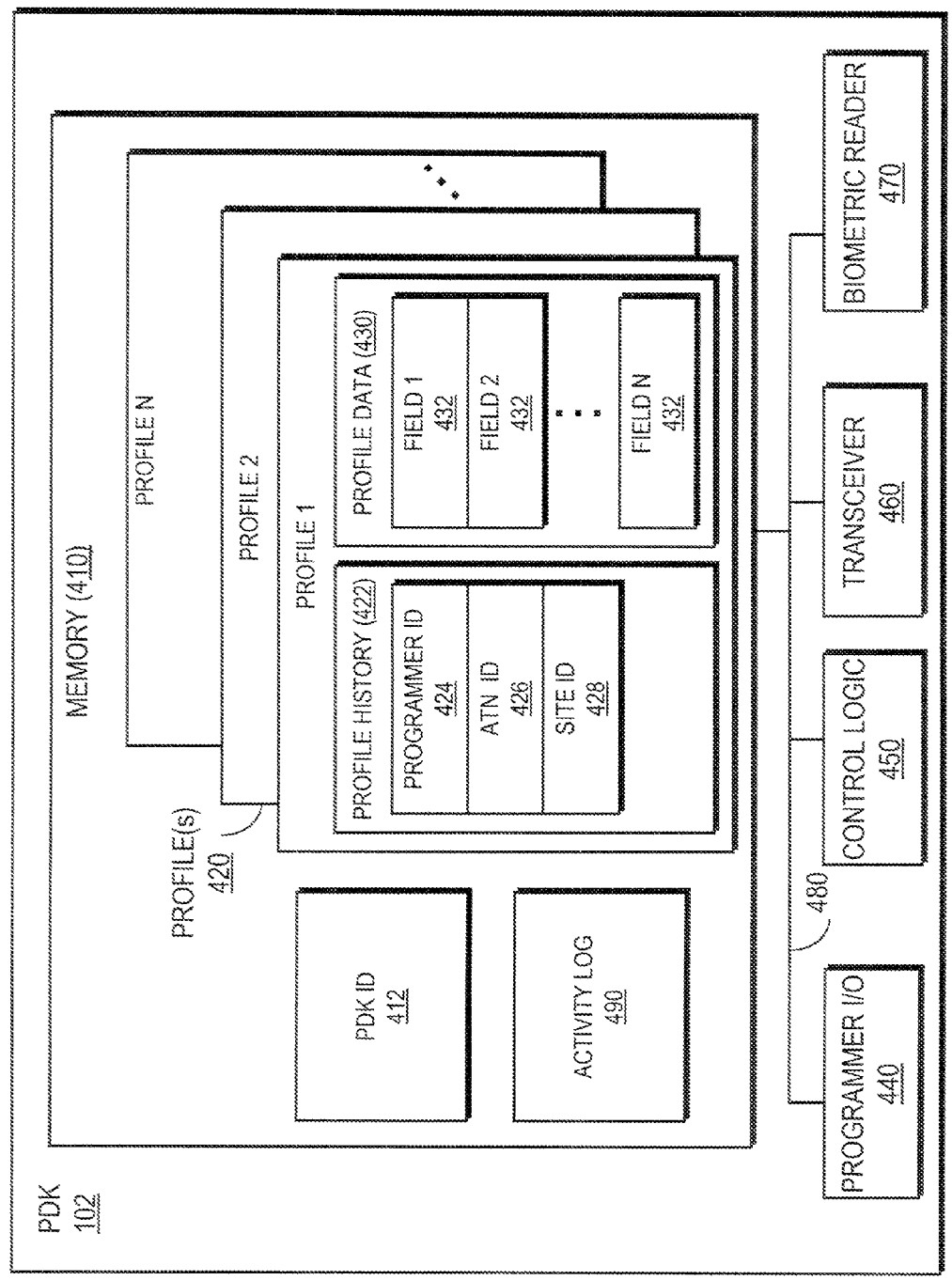
FIG. 4 is a block diagram illustrating one embodiment of a Personal Digital Key (PDK).

Turning now to FIG. 4, an example embodiment of a PDK 102 is illustrated. The PDK 102 comprises a memory 410, a programmer I/O 440, control logic 450, a transceiver 460 and a biometric reader 470 coupled by a bus 480. The PDK 102 can be standalone as a portable, physical device or can be integrated into commonly carried items. For example, a PDK 102 can be integrated into a portable electronic device such as a cell phone, Personal Digital Assistant (PDA), or GPS unit, an employee identification tag or badge, clothing, or jewelry items such as watches, rings, necklaces or bracelets. In one embodiment, the PDK 102 can be, for example, about the size of a Subscriber Identity Module (SIM) card and be as small as a square inch in area or less. In another embodiment, the PDK 102 can be easily contained in a pocket, on a keychain, or in a wallet. In yet another embodiment, a PDK 102 can be integrated into a sticker, tag or other item attachable to various items or equipment. In other embodiments, the PDK 102 can be integrated into a clipboard, patient wristband or other patient identification tags or badges. In some embodiments, where the PDK 102 is attached to equipment for tracking purposes, the PDK 102 also includes a button or switch that can be activated or deactivated to indicate whether the equipment is in use.

The memory 410 can be a read-only memory, a once-programmable memory, a read/write memory or any combination of memory types including physical access secured and tamperproof memories. The memory 410 typically stores a unique PDK ID 412, a activity log 490 and one or more profiles 420. The PDK ID 412 comprises a public section and a private section of information, each of which can be used for identification and authentication. In one embodiment, the PDK ID 412 is stored in a read-only format that cannot be changed subsequent to manufacture. The PDK ID 412 is used as an identifying feature of a PDK 102 and distinguishes between PDKs 102 in private 116 or Central 114 registry entries. In an alternative embodiment, the registries can identify a PDK 102 by a different ID than the PDK ID 412 stored in the PDK 102, or may use both the PDK ID 412 and the different ID in conjunction. The PDK ID 412 can also be used in basic PDK authentication to ensure that the PDK 102 is a valid device.

The activity log 490 stores information associated with various activities of the PDK. For example, if the PDK 102 is a patient's PDK, the activity log 490 stores information identifying the patient's location throughout various times. In one embodiment, the activity log 490 keeps track of each time the patient visits the healthcare facility. In another embodiment, the activity log 490 stores the patient's location throughout various points as the patient is in the provider's facility. Similarly, the if PDK 102 is attached to a piece of equipment or a cart of supplies, the activity log 490 stores location information as well. In another embodiment, if the PDK 102 is that of a provider, the activity log 490 stores information associated with the provider's rounds, i.e. each time a provider visits a certain patient or uses a particular medical device.

The profile fields 420 can be initially empty at the time of manufacture but can be written to by authorized individuals (e.g., a Notary) and/or hardware (e.g., a Programmer). In one embodiment, each profile 420 comprises a profile history 422 and profile data 430. Many different types of profiles 420 are possible. A biometric profile, for example, includes profile data 430 representing physical and/or behavioral information that can uniquely identify the PDK owner. A PDK 102 can store multiple biometric profiles, each comprising a different type of biometric information. In one embodiment, the biometric profile 420 comprises biometric information transformed by a mathematical operation, algorithm, or hash that represents the complete biometric information (e.g., a complete fingerprint scan). In one embodiment, a mathematical hash is a "one-way" operation such that there is no practical way to re-compute or recover the complete biometric information from the biometric profile. This both reduces the amount of data to be stored and adds an additional layer of protection to the user's personal biometric information. In one embodiment, the biometric profile is further encoded using an encoding key and/or algorithm that is stored with the biometric profile data. Then, for authentication, both the biometric profile data and the encoding key and/or algorithm are passed to the Reader 108.

In one embodiment the PDK 102 also stores one or more biometric profile "samples" associated with each biometric profile. The biometric profile sample is a subset of the complete profile that can be used for quick comparisons of biometric data. In one embodiment, the profile samples can be transmitted over a public communication channel or transmitted with reduced level of encryption while the full biometric profiles are only transmitted over secure channels. In the case of fingerprint authentication, for example, the biometric profile sample may represent only small portion area of the full fingerprint image. In another embodiment, the fingerprint profile sample is data that describes an arc of one or more lines of the fingerprint. In yet another embodiment, the fingerprint profile sample can be data representing color information of the fingerprint.

In another embodiment, the stored profiles 420 include a PIN profile that stores one or more PINs or passwords associated with the PDK owner. Here, the number or password stored in the PIN profile can be compared against an input provided by the user at the point of transaction to authenticate the user. In one embodiment, a PIN profile sample is also stored with the PIN profile that comprises a subset of the full PIN. For example, a PIN profile sample can be only the first two numbers of the PIN that can be used to quickly compare the stored PIN profile to a PIN obtained at the point of transaction.

In yet another embodiment, the PDK 102 stores a picture profile that includes one or more pictures of the PDK owner. In a picture profile authentication, the picture stored in the PDK 102 is transmitted to a display at the point of transaction to allow an administrator (e.g., a clerk or security guard) to confirm or reject the identity of the individual requesting the transaction. In another embodiment, an image is captured of the individual at the point of transaction and compared to the picture profile by an automated image analysis means. Furthermore, picture profiles could be used, for example, in place of conventional passports or drivers licenses to authenticate the identity of an individual and allow for remote identification of individuals. For example, a police officer following a vehicle could obtain an image and identity of the driver while still maintaining a safe distance from the vehicle. In the hospitality industry, a host could greet a guest at the door of a hotel, casino or restaurant and easily recognize the guest by obtaining the guest's picture profile as he/she enters. In healthcare, a doctor or nurse can ensure that he or she is administering the correct medication to the right patient by looking at the profile picture associated with that patient.

A registry or database profile typically stores information associating the user with a registry. The registry profile can be used to determine if the individual is associated with the controlling entity for that registry and if different types of transactions are authorized for the individual. A registry profile can further include additional user information for use with the registry. For example, a private registry profile associated with a particular merchant may include a credit card number that the user has selected as a default for that merchant. In one embodiment, a profile can further include spending limits that limits the amount of purchases a user can make with a particular vendor or using a particular profile.

A profile can further include personal identification information such as name, address, phone number, etc., insurance information, credit/debit card information, or information regarding visited providers. This information can be useful for certain types of transactions. For example, patient office visits, a PDK 102 can automatically transmit address, insurance and billing information to the Reader 108 at the conclusion of the office visit.

Generally, some types of profile information (e.g., a biometric profile) can only be acquired during a trusted initialization process that is administered by a trusted Notary. In one embodiment, other secure information such as medical conditions are also stored to the PDK 102 in the presence of a Notary. Alternatively, certain types of low-risk information can be added by the user without a Notary, such as, for example a change of address. In another embodiment, once an initial profile has been stored to the PDK 102, a user can add information to the PDK 102 using a Programmer without a Notary through self-authentication. For example, in one embodiment, a PDK 102 that has a stored biometric profile can be "unlocked" by providing a matching biometric input. Then, once unlocked, the user can add or remove additional profiles, insurance cards, personal information, etc. to the PDK 102 using a Programmer. For example, in one embodiment, a user that has unlocked his/her own PDK 102 can store additional biometric information (such as fingerprint information for other fingers) in his/her PDK 102. In another example, a user that cancels an insurance card, can unlock his/her PDK 102 to remove the insurance card information. In another embodiment, the user can make copies of the PDK 102 or move profiles from one PDK 102 to another once the PDK 102 is unlocked.

The profile history 422 includes a programmer ID field 424, a Notary ID 426, and a site ID field 428. The profile history 422 relates to the specific hardware, Notary, and site used at the time the profile data was created and stored to the PDK. Typically each profile 420 stores its specific profile history 422 along with the profile data 430. The profile history 422 can be recalled for auditing purposes at a later time to ensure the credibility of the stored data. In one embodiment, transaction history can also be stored to the PDK memory 410. Here, the PDK 102 stores information associated with any transactions made with the PDK 102 such as the healthcare provider, reason for office visit and insurance used, etc.

The PDK 102 also includes a programmer I/O 440 that provides an interface to a trusted Programmer (not shown). The Programmer comprises trusted hardware that is used to program the memory 410 of the PDK 102. An example embodiment of a Programmer is described in U.S. patent application Ser. No. 11/744,832 to John Giobbi, et al., entitled "Personal Digital Key Initialization and Registration For Secure Transaction" filed on May 5, 2007, the entire contents of which are incorporated herein by reference. The programmer I/O 440 can be, for example, a USB interface, serial interface, parallel interface, or any other direct or wireless link for transferring information between the PDK 102 and the Programmer. When coupled to the Programmer, the programmer I/O 440 receives initialization data, registration data or other information to be stored in the memory 410.

The control logic 450 coordinates between functions of the PDK 102. In one embodiment, the control logic 450 facilitates the flow of information between the programmer I/O 440, transceiver 460 and memory 410. The control logic 450 can further process data received from the memories 410, programmer I/O 440 and transceiver 460. Note that the control logic 450 is merely a grouping of control functions in a central architecture, and in other embodiments, the control functions can be distributed between the different modules of the PDK 102. The operation of the control logic will be understood to those skilled in the art based on the description below corresponding to FIGS. 8-11D.

The transceiver 460 is a wireless transmitter and receiver for wirelessly communicating with a Reader 108 or other wireless device. The transceiver 460 sends and receives data as modulated electromagnetic signals. Moreover, the data can be encrypted by the transceiver 460 and transmitted over a secure link. Further, the transceiver 460 can actively send connection requests, or can passively detect connection requests from another wireless source. In one embodiment, the transceiver 460 is used in place of a separate programmer I/O 440 and is used to wirelessly communicate with the Programmer for programming. In one embodiment, the transceiver 460 is adapted to communicate over a range of up to around 5 meters.

Optionally, the PDK 102 can also include a built in biometric reader 470 to acquire a biometric input from the user. The biometric reader 470 is configured to obtain a representation of physical or behavioral characteristics derived from the individual. The biometric input can be used to unlock the PDK 102 for profile updates, or for various types of authentication. For example, in one embodiment, a biometric input is received by the PDK 102 and compared to stored biometric information. Then, if the user is authenticated, the PDK 102 can indicate to the Reader 108 that the user is authenticated and transmit additional information (e.g., a credit card number) needed to complete a transaction.

Figure 5:
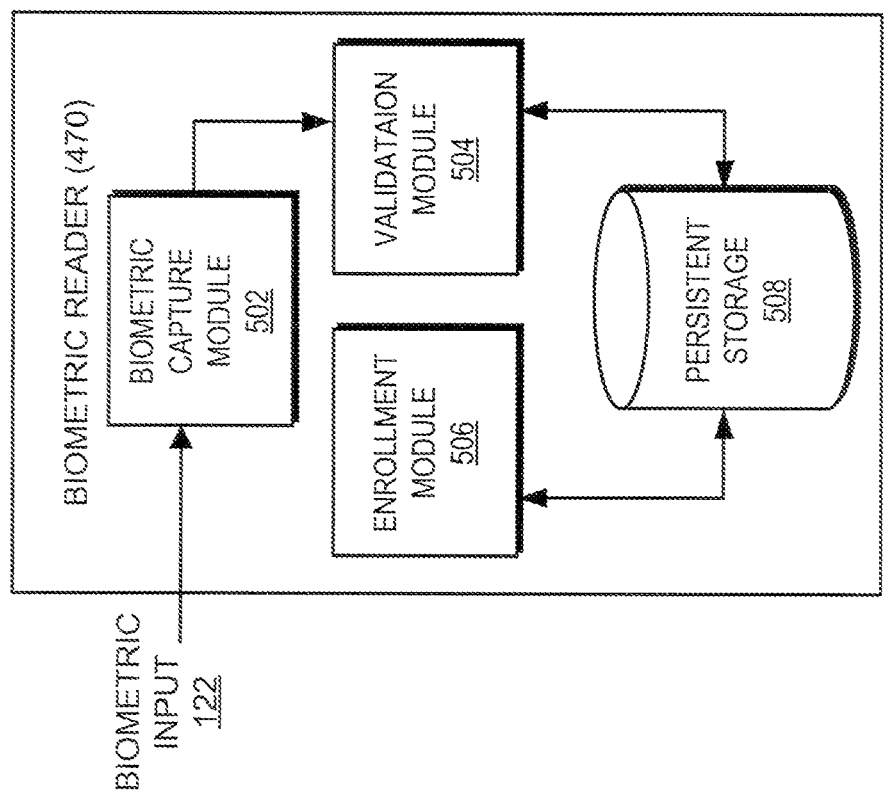
FIG. 5 is a block diagram illustrating one embodiment of a biometric reader of a PDK.

FIG. 5 is a block diagram illustrating one embodiment of a biometric reader 470 of a PDK 102. The biometric reader 470 includes a biometric capture module 502, a validation module 504, an enrollment module 506 and persistent storage 508. In one embodiment, the enrollment module 506 registers a user with a PDK 102 by persistently storing biometric data associated with the user. Further, enrollment module 506 registers PDK 102 with a trusted authority by providing the code (e.g., device ID) to the trusted authority. Or conversely, the trusted authority can provide the code to PDK 102 to be stored therein.

The biometric capture module 502 comprises a scan pad to capture scan data from a user's fingerprint (e.g., a digital or analog representation of the fingerprint). Other embodiments of the biometric capture module 502 includes retinal scanners, iris scanners, facial scanner, palm scanners, DNA/RNA analyzers, signature analyzers, cameras, microphones, and voice analyzers to capture other identifying biometric data. Using the biometric data, validation module 504 determines whether the user's fingerprint, or other biometric data, matches the stored biometric data from enrollment. Conventional techniques for comparing fingerprints can be used. For example, the unique pattern of ridges and valleys of the fingerprints can be compared. A statistical model can be used to determine comparison results. Validation module 504 can send comparison results to control logic 450 of the PDK 102.

In other embodiments, validation module 504 can be configured to capture biometric data for other human characteristics. For example, a digital image of a retina, iris, and/or handwriting sample can be captured. In another example, a microphone can capture a voice sample.

Persistent storage 508 persistently stores biometric data from one or more users which can be provided according to specific implementations. In one embodiment, at least some of persistent storage 508 is a memory element that can be written to once but cannot subsequently be altered. Persistent storage 508 can include, for example, a ROM element, a flash memory element, or any other type of non-volatile storage element. Persistent storage 508 is itself, and stores data in, a tamper-proof format to prevent any changes to the stored data. Tamper-proofing increases reliability of authentication because it does not allow any changes to biometric data (i.e., allows reads of stored data, but not writes to store new data or modify existing data). Furthermore, data can be stored in an encrypted form.

In one embodiment, persistent storage 508 also stores the code that is provided by the PDK 102 responsive to successful verification of the user. Further, in some embodiments persistent storage 508 stores other data utilized during the operation of PDK 102. For example, persistent storage 508 can store encryption/decryption keys utilized to establish secure communications links.

An example embodiment of PDK with a biometric reader is described in U.S. patent application Ser. No. 11/314,199 to John Giobbi, et al., entitled "Biometric Personal Data Key (PDK) Authentication", the entire contents of which are incorporated herein by reference.

Figure 6:
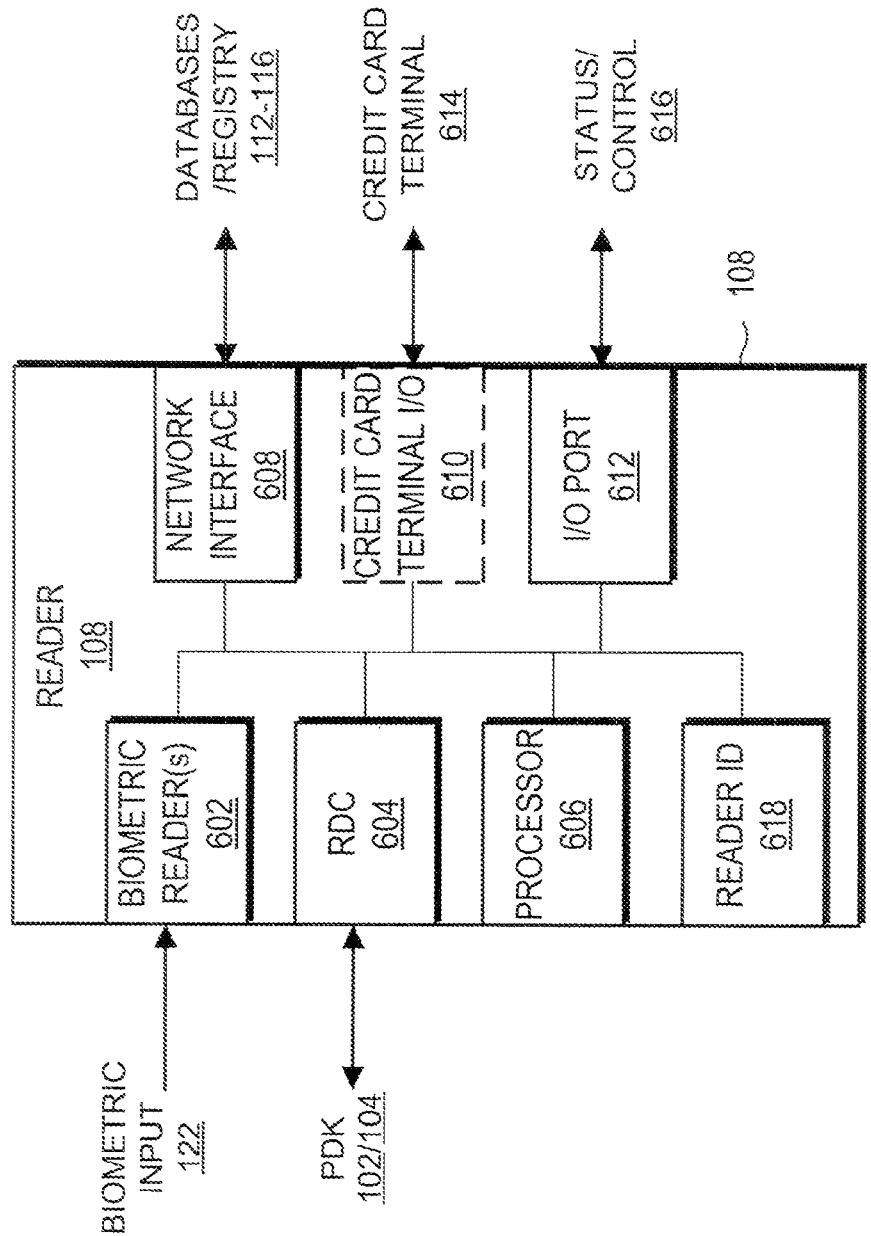
FIG. 6 is a block diagram illustrating one embodiment of a reader.

Turning now to FIG. 6, an example embodiment of a Reader 108 is illustrated. The embodiment includes one or more biometric readers 602, a receiver-decoder circuit (RDC) 604, a processor 606, a network interface 608, an I/O port 612, optionally a credit card terminal I/O 610 and a reader ID 618. In alternative embodiments, different or additional modules can be included in the Reader 108.

The RDC 604 provides the wireless interface to the PDK 102. Generally, the RDC 604 wirelessly receives data from the PDKs 102 in an encrypted format and decodes the encrypted data for processing by the processor 306. An example embodiment of an RDC is described in U.S. patent application Ser. No. 11/292,330 entitled "Personal Digital Key And Receiver/Decoder Circuit System And Method", the entire contents of which are incorporated herein by reference. Encrypting data transmitted between the PDK 102 and Reader 108 minimizes the possibility of eavesdropping or other fraudulent activity. In one embodiment, the RDC 604 is also configured to transmit and receive certain types of information in an unencrypted or public format.

The biometric reader 602 receives and processes the biometric input 122 from an individual and is configured to obtain a representation of physical or behavioral characteristics derived from the individual. In one embodiment, the biometric reader 602 is a fingerprint scanner. Here, the biometric reader 602 includes an image capture device adapted to capture the unique pattern of ridges and valleys in a fingerprint also known as minutiae. Other embodiments of biometric readers 602 include retinal scanners, iris scanners, facial scanner, palm scanners, DNA/RNA analyzers, signature analyzers, cameras, microphones, and voice analyzers. Furthermore, the Reader 108 can include multiple biometric readers 602 of different types. In one embodiment, the biometric reader 602 automatically computes mathematical representations or hashes of the scanned data that can be compared to the mathematically processed biometric profile information stored in the PDK 102.

The processor 606 can be any general-purpose processor for implementing a number of processing tasks. Generally, the processor 606 processes data received by the Reader 108 or data to be transmitted by the Reader 108. For example, a biometric input 122 received by the biometric reader 602 can be processed and compared to the biometric profile 420 received from the PDK 102 in order to determine if a transaction should be authorized. In different embodiments, processing tasks can be performed within each individual module or can be distributed between local processors and a central processor. The processor 606 further includes a working memory for use in various processes such as performing the method of FIGS. 8-11D.

The network interface 608 is a wired or wireless communication link between the Reader 108 and one or more external databases such as, for example, a validation database 112, the Central Registry 114 or a private registry 116a, 116b. For example, in one type of authentication, information is received from the PDK 102 at the RDC 604, processed by the processor 606, and transmitted to an external database 112-116 through the network interface 608. The network interface 608 can also receive data sent through the network 110 for local processing by the Reader 108. In one embodiment, the network interface 608 provides a connection to a remote system administrator to configure the Reader 108 according to various control settings.

The I/O port 612 provides a general input and output interface to the Reader 108. The I/O port 612 may be coupled to any variety of input devices to receive inputs such as a numerical or alphabetic input from a keypad, control settings, menu selections, confirmations, and so on. Outputs can include, for example, status LEDs, an LCD, or other display that provides instructions, menus or control options to a user.

The credit card terminal I/O 610 optionally provides an interface to an existing credit card terminal 614. In embodiments including the credit card terminal I/O 610, the Reader 108 supplements existing hardware and acts in conjunction with a conventional credit card terminal 614. In an alternative embodiment, the functions of an external credit card terminal 614 are instead built into the Reader 108. Here, a Reader 108 can completely replace an existing credit card terminal 614.

In one embodiment, a Reader 108 is adapted to detect and prevent fraudulent use of PDKs that are lost, stolen, revoked, expired or otherwise invalid. For example, the Reader 108 can download lists of invalid PDKs IDs 412 from a remote database and block these PDKs 102 from use with the Reader 108. Furthermore, in one embodiment, the Reader 108 can update the blocked list and/or send updates to remote registries 114, 116a, 116b or remote Readers 108 upon detecting a fraudulently used PDK 102. For example, if a biometric input 122 is received by the Reader 108 that does not match the biometric profile received from the PDK 102, the Reader 108 can obtain the PDK ID 412 and add it to a list of blocked PDK IDs 412. In another embodiment, upon detecting fraudulent use, the Reader 108 can send a signal to the PDK 102 that instructs the PDK 102 to deactivate itself. The deactivation period can be, for example, a fixed period of time, or until the rightful owner requests re-activation of the PDK 102. In yet another embodiment, the Reader 108 can send a signal instructing the fraudulently obtained PDK 102 to send alarm signals indicating that the PDK 102 a stolen device. Here, a stolen PDK 102 can be tracked, located and recovered by monitoring the alarm signals. In one embodiment, the Reader 108 stores biometric or other identifying information from an individual that attempts to fraudulently use a PDK 102 so that the individual's identity can be determined.

The reader ID 618 is memory that stores the reader's unique identification number. The memory can be a read-only memory, a once-programmable memory, a read/write memory or any combination of memory types including physical access secured and tamperproof memories. The reader ID 618 plays an integral role in the process for tracking equipment, supplies and individuals as will be explained in more detail below.

Generally, the Reader 108 is configured to implement at least one type of authentication prior to enabling a transaction. In many cases, multiple layers of authentication are used. A first layer of authentication, referred to herein as "device authentication," begins any time a PDK 102 moves within range of a Reader 108. In device authentication, the Reader 108 and the PDK 102 each ensure that the other is valid based on the device characteristics, independent of any profiles stored in the PDK 102. In some configurations, when fast and simple authentication is desirable, only device authentication is required to initiate the transaction. For example, a Reader 108 may be configured to use only device authentication for office visit check-ins. The configuration is also useful in other types of low risk transactions where speed is preferred over additional layers of authentication.

Other configurations of the Reader 108 require one or more additional layers of authentication, referred to herein as "profile authentication" based on one or more profiles stored in the PDK 102. Profile authentication can include, for example, a biometric authentication, a PIN authentication, a photo authentication, a registry authentication, etc. or any combination of the above authentication types. Profile authentications are useful when a more exhaustive authentication process is desired, for example, for invasive patient treatments or drug administration.

Figure 7:
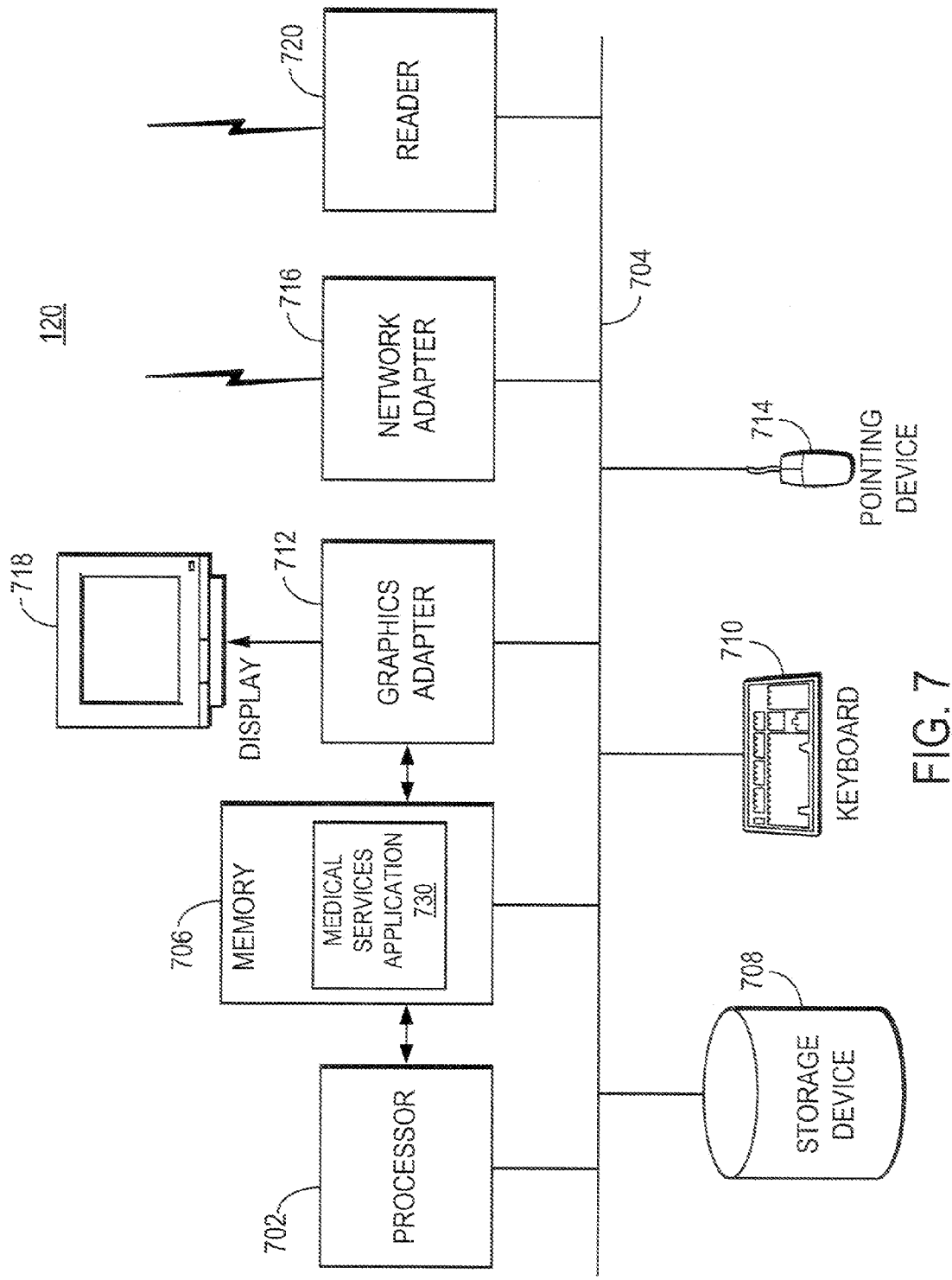
FIG. 7 is a block diagram illustrating one embodiment of a provider interface device.

FIG. 7 is a high-level block diagram of one embodiment of a provider interface device 120. In one embodiment, the provider interface device 120 is a personal computer. In another embodiment, the provider interface device 120 is a smart phone or other mobile computing and communication device. Illustrated are at least one processor 702 coupled to a bus 704. Also coupled to the bus 704 are a memory 706, a storage device 708, a keyboard 710, a graphics adapter 712, a pointing device 714, a network adapter 716 and a reader 720. In one embodiment, the functionality of the bus 704 is provided by an interconnecting chipset. A display 718 is coupled to the graphics adapter 712.

The memory 706 includes a medical services application 730. In one embodiment, the medical services application 730 enables the provider interface device 120 to communicate with the local services 124 and third party link module 126. In another embodiment, the medical services application 730 processes information and data received from the readers 720 and various modules and servers of the local services 124 and third party link module 126.

The storage device 708 is any device capable of holding data, like a hard drive, compact disk read-only memory (CD-ROM), DVD, or a solid-state memory device. The memory 706 holds instructions and data used by the processor 702. The pointing device 714 may be a mouse, track ball, or other type of pointing device, and is used in combination with the keyboard 710 to input data into the provider interface device 120. The graphics adapter 712 displays images and other information on the display 718. The network adapter 716 couples the provider interface device 120 to a local or wide area network.

As is known in the art, a provider interface device 120 can have different and/or other components than those shown in FIG. 7. In addition, the provider interface device 120 can lack certain illustrated components. In one embodiment, a provider interface device 120 lacks a keyboard 710, pointing device 714, graphics adapter 712, and/or display 718. Moreover, the storage device 708 can be local and/or remote from provider interface device 120 (such as embodied within a storage area network (SAN)). The reader 720 includes all or some of the same components as the Reader 108 as shown in FIG. 6.

As is known in the art, the provider interface device 120 is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device 708, loaded into the memory 706, and executed by the processor 702.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

Figure 8:
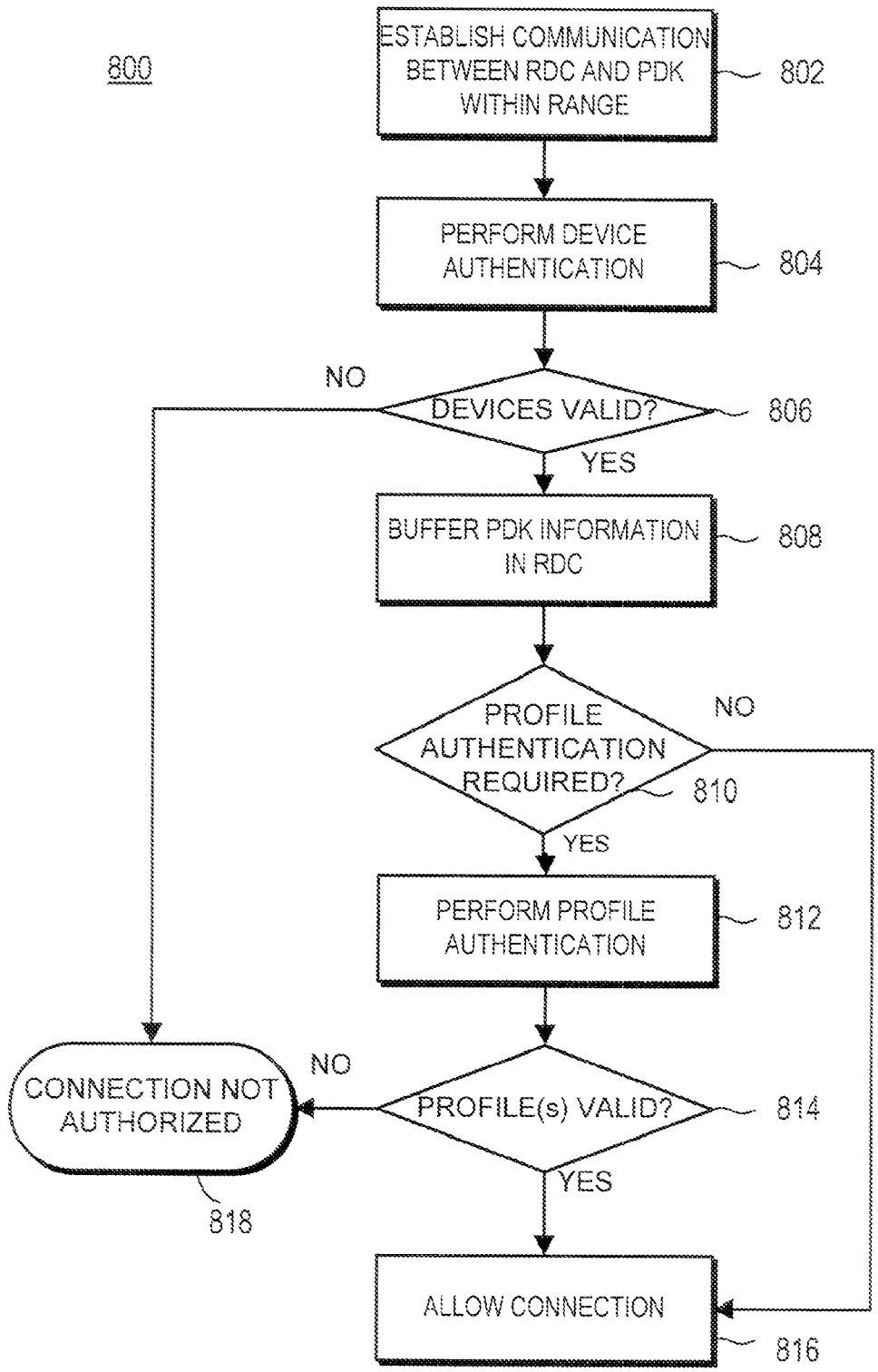
FIG. 8 is a flowchart illustrating one embodiment of a process for authorizing a communication connection using secure authentication.

FIG. 8 is a flowchart illustrating one embodiment of a process for authorizing a communication connection using secure authentication. When a PDK 102 comes within range of a Reader 108, communication is automatically established 802 between the RDC 604 of the Reader 108 and the PDK 102. It should be noted that the processes described herein with regards to Reader 108 may be also performed with reader 720 of the provider interface device 120.

In one embodiment, the RDC 604 continually transmits beacons that are detected by the PDK 102 when it enters a proximity zone of the Reader 108. In an alternative embodiment, the communication is instead initiated by the PDK 102 and acknowledged by the Reader 108. Generally, initial communication between the Reader 108 and the PDK 102 is not encrypted in order to provide faster and more power efficient communication.

In step 804, a device authentication is performed. Here, the Reader 108 establishes if the PDK 102 is a valid device and PDK 102 establishes if the Reader 108 is valid. Furthermore, device authentication determines if the PDK 102 is capable of providing the type of authentication required by the Reader 108.

Figure 9:
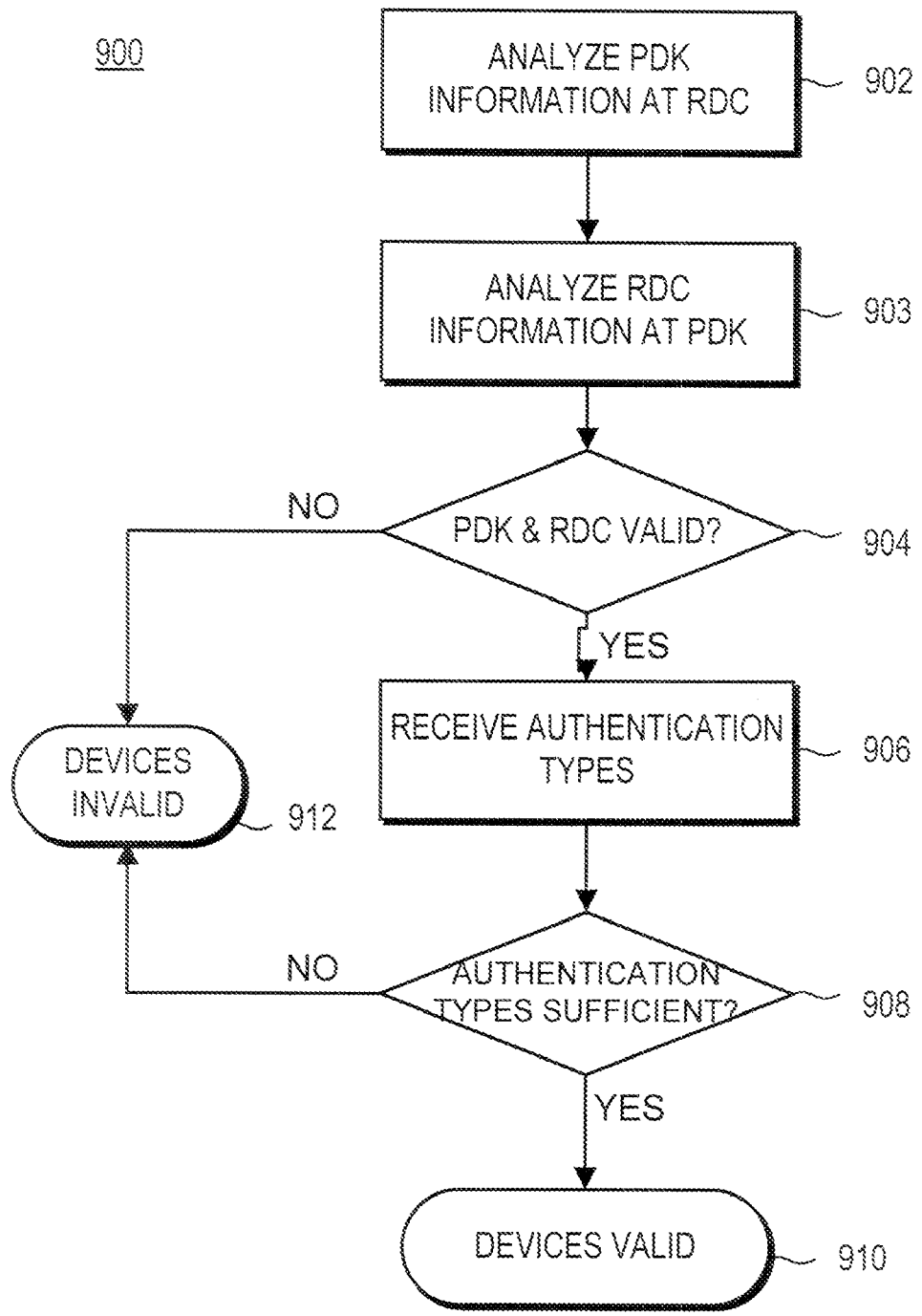
FIG. 9 is a flowchart illustrating one embodiment of a process for device authentication by a reader.

An example embodiment of a method for performing 804 device authentication is illustrated in FIG. 9. The RDC 604 receives and analyzes 902 information from the PDK 102; and the PDK 102 receives and analyzes 902 information received from the RDC 604. Generally, this initial information is transmitted over a public communication channel in an unencrypted format. Based on the received information, each device 102, 604 determines 904 if the other is valid. As will be apparent to one of ordinary skill in the art, a number of different protocols can be used for this type of authentication such as, for example, a challenge-response authentication or a challenge handshake authentication protocol (CHAP). If either of the devices 102, 604 is invalid 912, the process ends. If both the PDK 102 and the RDC 604 are determined by the other to be valid, the Reader 108 requests and receives 906 authentication type information from the PDK 102 indicating the different types of authentication the PDK 102 is capable of satisfying based on the types of profiles the PDK 102 stores. The available profile types in the PDK 102 are compared against the authentication types that can be used by the Reader 108. For example, a particular Reader 108 may be configured to perform only a fingerprint authentication and therefore any PDK without a fingerprint biometric profile cannot be used with the Reader 108. In one embodiment, the Reader 108 can allow more than one type of profile to be used. In another embodiment, the Reader 108 requires more than one type of profile for authentication, while in yet further embodiments no profile authentications are required. Next, the method determines 908 whether the PDK 102 has one or more profiles sufficient for authentication. If the PDK 102 does not have one or more profiles sufficient for authentication with the Reader 108, the devices 102, 604 are determined to be invalid 912 because they cannot be used with each other. If the PDK 102 does have one or more sufficient types of profiles, the devices are valid 910.

Turning back to FIG. 8, if either the PDK 102 or RDC 604 is not found valid during device authentication 804, the connection is not authorized 818 and the process ends. If the devices are valid, the RDC 604 temporarily buffers 808 the received PDK information. It is noted that in one embodiment, steps 802-808 are automatically initiated each time a PDK 102 enters the proximity zone of the Reader 108. Thus, if multiple PDKs 102 enter the proximity zone, the Reader 108 automatically determines which PDKs 102 are valid and buffers the received information from each valid PDK 102.

The method next determines 810 whether profile authentication is required based on the configuration of the Reader 108, the type of transaction desired or by request of a merchant or other administrator. If the Reader 108 configuration does not require a profile authentication in addition to the PDK authentication, then the Reader 108 proceeds to complete the transaction for the PDK 102. If the Reader 108 does require profile authentication, the profile authentication is performed 812 as will be described below with references to FIGS. 10-11D. If a required profile is determined 814 to be valid, the Reader 108 allows 816 the connection. Otherwise, the Reader 108 indicates that the connection is not authorized 818. In one embodiment, allowing 816 the connection includes enabling access to secure patient records. In another embodiment, allowing 816 the connection includes enabling the automatic logging in and out of software and system applications. Patient or provider name or medical record number (typically stored in a profile memory field 432) can be transmitted by the PDK 102 for identification purposes. In one embodiment, the PDK 102 is configured with multiple purchasing means and a default is configured for different types of transactions. In another embodiment, each insurance card or medical billing information is displayed to the customer by the Reader 108 and the customer is allowed to select which to apply to the office visit.

Figure 10:
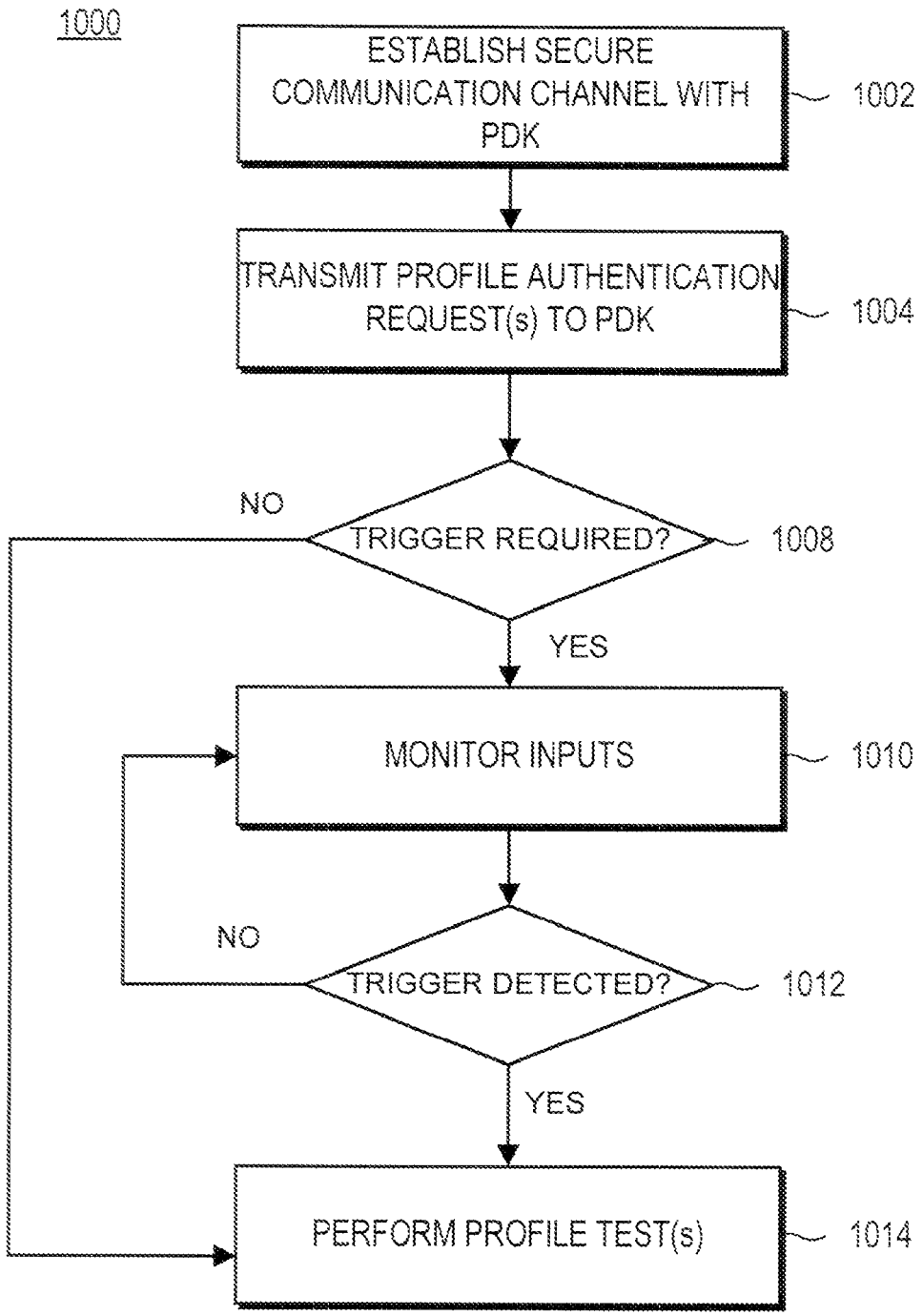
FIG. 10 is a flowchart illustrating one embodiment of a process for profile authentication by a reader.

Turning now to FIG. 10, an embodiment of a process for profile authentication is illustrated. In step 1002, a secure communication channel is established between the RDC 604 and the PDK 102. Information sent and received over the secure channel is in an encrypted format that cannot be practically decoded, retransmitted, reused, or replayed to achieve valid responses by an eavesdropping device. The Reader 108 transmits 1004 profile authentication requests to the PDK 102 requesting transmission of one or more stored profiles over the secure channel. At 1008, the process determines whether a "trigger" is required for authentication. The requirement for a trigger depends on the configuration of the Reader 108, the specific type of transaction to be executed and the type of authentication requested.

In a first configuration, a trigger is required to continue the process because of the type of authentication being used. For example, in biometric authentication, the authentication process cannot continue until the Reader detects a biometric contact and receives biometric information. It is noted that biometric contact is not limited to physical contact and can be, for example, the touch of a finger to a fingerprint scanner, the positioning of a face in front of a facial or retinal scanner, the receipt of a signature, the detection of a voice, the receipt of a DNA sample, RNA sample, or derivatives or any other action that permits the Reader 108 to begin acquiring the biometric input 122. By supplying the biometric contact, the user indicates that the authentication and transaction process should proceed. For example, a PDK holder that wants log in to the healthcare software application system via the provider interface device 120 initiates the logon process by touching a finger to the reader 720 of the provider interface device 120. The provider interface device 120 then displays confirmation of the user's login.

In a second configuration, some other user action is required as a trigger to proceed with the transaction even if the authentication process itself doesn't necessarily require any input. This can be used for many purchasing transactions to ensure that the purchase is not executed until intent to purchase is clear. For example, a Reader 108 at a gas station can be configured to trigger the transaction when a customer begins dispensing gas. At a supermarket, a Reader 108 can be configured to trigger the transaction when items are scanned at a checkout counter. Similarly, a user may log in to healthcare software application system via the provider interface device 120 by simply being in the proximity zone of the reader 720 of a provider interface device 120 and beginning to use the keyboard 710 or pointing device 714 of the provider interface device 120.

In a third configuration, no trigger is used and the Reader 108 automatically completes the remaining authentication/transaction with no explicit action by the user. This configuration is appropriate in situations where the mere presence of a PDK 102 within range of the Reader 108 is by itself a clear indication of the person associated with the PDK 102 desires to complete a transaction. For example, a Reader 108 can be positioned inside the entrance to a doctor's office or clinic. When a patient having an associated PDK walks through the entrance, the Reader 108 detects the PDK 102 within range, authenticates the user, and notifies the receptionist that the patient has arrived for his or her appointment. Thus, if no trigger is required, the process next performs 1014 the requested profile authentication tests.

If a trigger is required, the Reader 108 monitors 1010 its inputs (e.g., a biometric reader, key pad, etc.) and checks for the detection 1012 of a trigger. If the required trigger is detected, the process continues to perform 1014 one or more profile authentication test. FIGS. 11A-11D illustrate various embodiments of profile authentication tests. According to different configurations of the Reader 108, one or more of the illustrated authentication processes may be used. Further, in some embodiments, one or more of the processes may be repeated (e.g., for different types of biometric inputs).

Referring first to FIG. 11A, it illustrates a process for biometric authentication. In biometric authentication, a Reader 108 compares a biometric profile stored in the PDK 102 to the biometric input 122 acquired by the biometric reader 602. Advantageously, the biometric input 122 is not persistently stored by the Reader 108, reducing the risk of theft or fraudulent use. If 1102 biometric authentication is requested, the Reader 108 scans 1104 the biometric input 122 supplied by the user. In one embodiment, scanning 1104 includes computing a mathematical representation or hash of the biometric input 122 that can be directly compared to the biometric profile.

Furthermore, in one embodiment, scanning 1104 also includes obtaining a biometric input sample from the biometric input according to the same function used to compute the biometric profile sample stored in the PDK 102. Optionally, the Reader 108 receives 1108 a biometric profile sample from the PDK 102 and determines 1110 if the biometric profile sample matches the biometric input sample. If the biometric profile sample does not match the input sample computed from the scan, the profile is determined to be invalid 1118. If the biometric profile sample matches, the full biometric profile 1112 is received from the PDK 102 to determine 1114 if the full biometric profile 1112 matches the complete biometric input 122. If the profile 1112 matches the scan, the profile 1112 is determined to be valid 1120, otherwise the profile 1112 is invalid 1118. It is noted that in one embodiment, steps 1108 and 1110 are skipped and only a full comparison is performed. In one embodiment, the biometric profile and/or biometric profile sample is encoded and transmitted to the Reader 108 along with an encoding key and/or algorithm. Then, the Reader 108 uses the encoding key and/or algorithm to recover the biometric profile and/or biometric profile sample. In another alternative embodiment, only the encoding key and/or algorithm is transmitted by the PDK 102 and the biometric profile data is recovered from a remote database in an encoded form that can then be decoded using the key and/or algorithm.

It will be apparent to one of ordinary skill that in alternative embodiments, some of the steps in the biometric profile authentication process can be performed by the PDK 102 instead of the Reader 108 or by an external system coupled to the Reader 108. For example, in one embodiment, the biometric input 122 can be scanned 1104 using a biometric reader built into the PDK 102. Furthermore, in one embodiment, the steps of computing the mathematical representation or hash of the biometric input and/or the steps of comparing the biometric input to the biometric profile can be performed by the PDK 102, by the Reader 108, by an external system coupled to the Reader 108, or by any combination of the devices. In one embodiment, at least some of the information is transmitted back and forth between the PDK 102 and the Reader 108 throughout the authentication process. For example, the biometric input 122 can be acquired by the PDK 102, and transmitted to the Reader 108, altered by the Reader 108, and sent back to the PDK 102 for comparison. Other variations of information exchange and processing are possible without departing from the scope of the invention. The transfer of data between the PDK 102 and the Reader 108 and/or sharing of processing can provide can further contribute to ensuring the legitimacy of each device.

FIG. 11B illustrates a process for PIN authentication. If PIN authentication is requested 1124, a PIN is acquired 1126 from the user through a keypad, mouse, touch screen or other input mechanism. Optionally, the Reader 108 receives 1128 a PIN sample from the PDK 102 comprising a subset of data from the full PIN. For example, the PIN sample can comprise the first and last digits of the PIN. If the Reader 108 determines 1130 that the PIN sample does not match the input, the profile is immediately determined to be invalid 1136. If the PIN sample matches, the full PIN profile is received 1132 from the PDK and compared to the input. If the Reader 108 determines 1134 that the profile matches the input, the profile is determined to be valid and is otherwise invalid 1136. It is noted that in one embodiment, steps 1128 and 1130 are skipped.

Figures 11C, 11D:
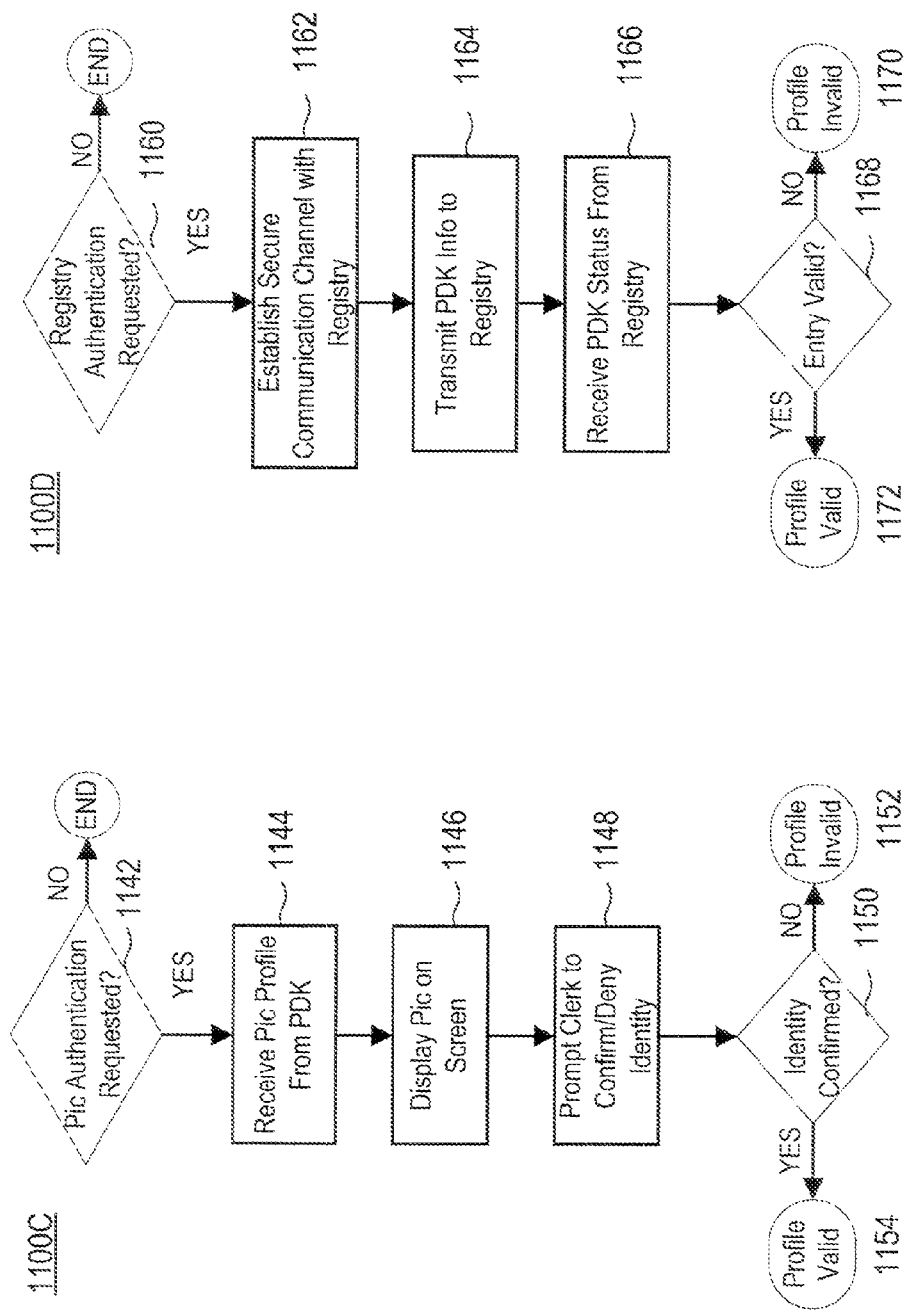
FIG. 11C is a flowchart illustrating one embodiment of a process for profile testing using a picture profile.
FIG. 11D is a flowchart illustrating one embodiment of a process for profile testing using a private or central registry.

FIG. 11C illustrates a process for a picture authentication. If the Reader 108 determines 1124 that picture authentication is requested, a picture profile is received 1144 from the PDK 102 by the Reader 108 and displayed 1146 on a screen. An administrator (e.g., a clerk, security guard, etc.) is prompted 1148 to compare the displayed picture to the individual and confirms or denies if the identities match. If the administrator confirms that the identities match, the picture profile is determined to be valid 1164 and is otherwise invalid 1152. In an alternative embodiment, the process is automated and the administrator input is replaced with a process similar to that described above with reference to FIG. 11A. Here, an image of the user is captured and face recognition is performed by comparing picture profile information received from the PDK 102 to the captured image.

FIG. 11D illustrates a process for authentication with a private registry 116a, 116b or the Central Registry 114. If the Reader 108 determines that registry authentication is requested, a secure communication channel is established 1162 over the network 110 between the Reader 108 and one or more registries (e.g., the Central Registry 114, any private registry 116a, 116b, or other validation database 112). If any additional information is needed to process the registry authentication (e.g., an insurance policy number), the Reader 108 requests and receives the additional information from the PDK 102. Identification information is transmitted 1164 from the Reader 108 to the registry 114, 116a, 116b through the network interface 608. The PDK status is received 1166 from the registry to determine 1168 if the status is valid 1172 or invalid 1170. In one embodiment, the information is processed remotely at the registry 114, 116a, 116b and the registry 114, 116a, 116b returns a validation decision to the Reader 108. In another embodiment, the Reader 108 queries the private 116a, 116b or Central registry 114 for information that is returned to the Reader 108. The information is then analyzed by the Reader 108 and the authorization decision is made locally. In one embodiment, the process involves transmitting credit card (or other purchasing information) to a validation database 112 to authorize the purchase and receive the status of the card. Status information may include, for example, confirmation that the card is active and not reported lost or stolen and that sufficient funds are present to execute the purchase.

Figure 12:
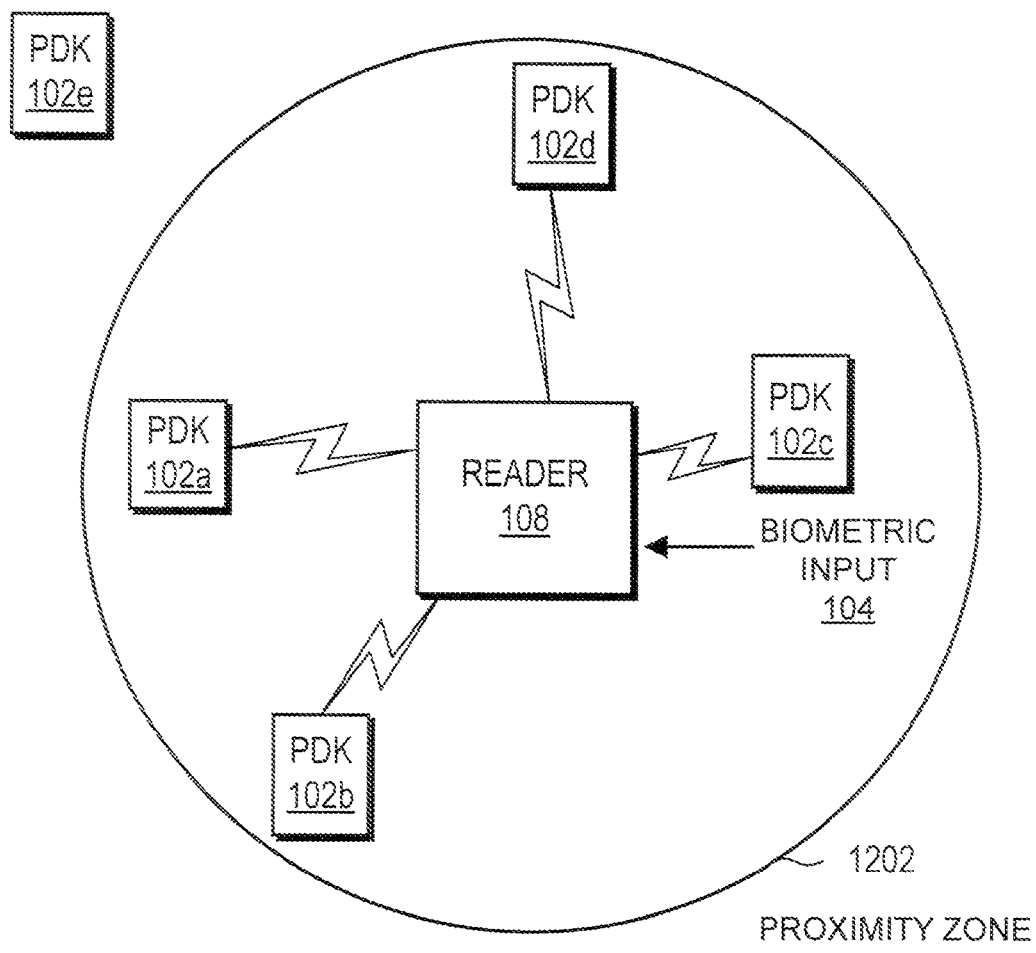
FIG. 12 illustrates an example scenario of a reader operating in a congested area with multiple PDKs within its proximity zone.

Turning now to FIG. 12 a scenario is illustrated where multiple PDKs 102a-e are present near a Reader 108. This scenario is common when a Reader 108 is located in a high occupancy area such as, for example, a hospital lobby or waiting area. Here, the Reader 108 can communicate with PDKs 102a-d within the proximity zone 1202 and does not communicate with PDKs 102e-f outside the proximity zone 1202. In one embodiment, the Reader 108 receives the unique PDK ID from a PDK 102 when it enters the proximity zone 1202 and records its time of arrival. In one embodiment, the Reader 108 further initiates a device authentication of the PDK 102 after a predefined period of time (e.g., 5 seconds) that the PDK 102 is within the proximity zone 1202. For profile authentication, the Reader 108 automatically determines which PDK 102 should be associated with an authentication test and the transaction. For example, if the Reader 108 receives a biometric input 122 from an individual, the Reader 108 automatically determines which PDK 102a-d is associated with the individual supplying the biometric input 122. In another embodiment, a different trigger is detected (e.g., a PIN input) to initiate the differentiation decision. In yet another embodiment, the differentiation decision is initiated without any trigger. It is noted that in some embodiments, where no trigger is required (such as a registry authentication), no differentiation decision is made and authentications are instead performed for each PDK 102 within the proximity zone 1202.

Figure 13:
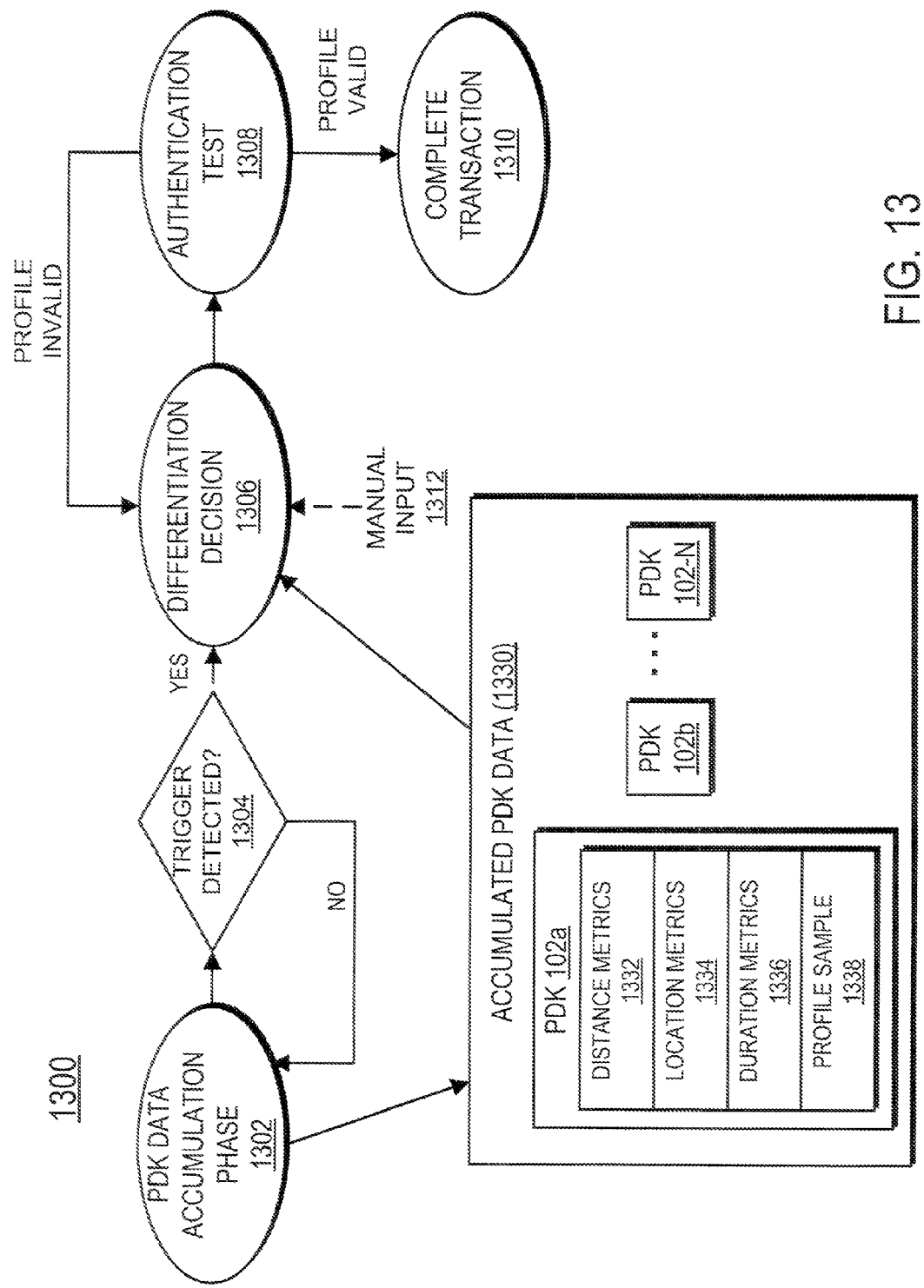
FIG. 13 is a flowchart illustrating one embodiment of a process for differentiating between multiple PDKs in completing a secure authentication process.

FIG. 13 illustrates an embodiment of an authentication process 1300 for the scenario where multiple PDKs 102 are present within the proximity zone 1202 of the Reader 108. In a PDK data accumulation phase 1302, PDK data 1330 is accumulated and buffered in the Reader 108 for any valid PDKs 102 that enter the proximity zone 1202. In one embodiment, the accumulation phase 1302 begins for a PDK 102 after it has been within the proximity zone 1202 for a predetermined period of time. In one embodiment, the PDK data accumulation phase 1302 is similar to the steps 802-808 described above in detail with reference to FIG. 8 for each PDK 102a-d in the proximity zone 1202.

As illustrated, the accumulated PDK data 1330 includes one or more differentiation metrics from each valid PDK 102 within range of the Reader 108. The differentiation metrics can include any information that can be used by the Reader 108 to determine which PDK 102 should be associated with the authentication and/or transaction request. According to various embodiments, differentiation metrics can include one or more of distance metrics 1332, location metrics 1334 and duration metrics 1336.

In one embodiment, a distance metric 1332 indicates the relative distance of a PDK 102 to the Reader 108. This information is useful given that a PDK 102 having the shortest distance to the Reader 108 is generally more likely to be associated with a received authentication trigger (e.g., a biometric input, a PIN input or a transaction request). The distance metrics 1332 can include, for example, bit error rates, packet error rates and/or signal strength of the PDKs 102. These communication measurements can be obtained using a number of conventional techniques that will be apparent to those of ordinary skill in the art. Generally, lower error rates and high signal strength indicate the PDK 102 is closer to the Reader 108.

Location metrics 1334 can be used to determine a location of a PDK 102 and to track movement of a PDK 102 throughout an area. This information can be useful in determining the intent of the PDK holder to execute a transaction. For example, a PDK holder that moves in a direct path towards a cashier and then stops in the vicinity of the cashier is likely ready to make a purchase (or may be waiting in line to make a purchase). On the other hand, if the PDK moves back and forth from the vicinity of a cashier, that PDK holder is likely to be browsing and not ready to make a purchase. Examples of systems for determining location metrics are described in more detail below with reference to FIGS. 14-15.

The differentiation metrics can also include duration metrics 1336 that tracks the relative duration a PDK 102 remains within the proximity zone 1202. Generally, the PDK 102 with the longest time duration within the proximity zone 1202 is most likely to be associated with the authentication request. For example, if the Reader 108 is busy processing a purchasing transaction at a cashier and another PDK 102 has a long duration within the proximity zone 1202, it is likely that the user is waiting in line to make a purchase. In one embodiment, the Reader 108 tracks duration 1336 by starting a timer associated with a PDK 102 when the PDK 102 enters the proximity zone 1202 and resetting the time to zero when the PDK exists. As another example, the Reader 108 tracks the duration when a PDK of a doctor enters the proximity zone of a patient's room. A long duration of the doctor's PDK within the proximity zone can provide evidence that the doctor is spending an adequate amount of time examining the patient. On the other hand, a short duration of the doctor's PDK within the proximity zone can provide evidence that the doctor just merely stopped by and did not perform any thorough examination. This information is useful in monitoring patient treatment and provider performance to help ensure quality patient care.

In one embodiment, the Reader 108 can also receive and buffer profile samples 1338 prior to the start of a profile authentication instead of during the authentication process as described in FIG. 11A-11B. In one embodiment, the Reader 108 determines which types of biometric profile samples 1338 to request based on, for example, the configuration of the Reader 108, the type of transactions performed by the Reader 108, or manual requests from a clerk, security guard, etc. In one embodiment, the PDK 102 transmits one or more of the requested sample types based on profiles available in the PDK 102 and/or user preferences. In another embodiment, the PDK 102 transmits one or more samples 1338 it has available and only samples that match the authentication types configured for the Reader 108 are buffered. For example, if a Reader 108 is configured for fingerprint authentication, a PDK 102 may transmit samples 1338 for several different fingerprint profiles (each corresponding to a different finger, for example). It will be apparent to one of ordinary skill in the art that other variations are possible to provide flexibility in both the configuration of the Reader 108 for various types of authentication and flexibility for the PDK owner to determine which types of authentication to use.

Because profile samples 1338 only comprise a subset of the profile information, in one embodiment, the samples can be safely transmitted over a public channel without needing any encryption. In another embodiment, the profile samples 1338 are transmitted with at least some level of encryption. In yet another embodiment, some of the data is transmitted over a public communication channel and additional data is transmitted over a secure communication channel. In different configurations, other types of profile information can be accumulated in advance. For example, in one embodiment, a photograph from a picture profile can be obtained by the Reader 102 during the data accumulation phase 1302. By accumulating the profile sample 1338 or other additional information in advance, the Reader 108 can complete the authentication process more quickly because it does not wait to receive the information during authentication. This efficiency becomes increasingly important as the number of PDKs 102 within the proximity zone 1202 at the time of the transaction becomes larger.

The PDK accumulation phase 1302 continues until a trigger (e.g., detection of a biometric input) is detected 1304 to initiate a profile authentication process. If a biometric input is received, for example, the Reader 108 computes a mathematical representation or hash of the input that can be compared to a biometric profile and computes one or more input samples from the biometric input. It is noted that in alternative embodiments, the process can continue without any trigger. For example, in one embodiment, the transaction can be initiated when a PDK 102 reaches a predefined distance from the Reader 108 or when the PDK 102 remains within the proximity zone 1202 for a predetermined length of time.

The process then computes a differentiation decision 1306 to determine which PDK 102*a-d* should be associated with the authentication. In one embodiment, the Reader 108 computes a differentiation result for each PDK using one or more of the accumulated data fields 1330. For example, in one embodiment, the differentiation result is computed as a linear combination of weighted values representing one or more of the differentiation metrics. In another embodiment, a more complex function is used. The differentiation results of each PDK 102 are compared and a PDK 102 is selected that is most likely to be associated with the transaction.

In another embodiment, for example, in a photo authentication, the differentiation decision can be made manually by a clerk, security guard, or other administrator that provides a manual input 1312. In such an embodiment, a photograph from one or more PDKs 102 within the proximity zone 1202 can be presented to the clerk, security guard, or other administrator on a display and he/she can select which individual to associate with the transaction. In yet another configuration, the decision is made automatically by the Reader 108 but the clerk is given the option to override the decision.

An authentication test 1308 is initiated for the selected PDK 102. The authentication test 908 can include one or more of the processes illustrated in FIGS. 11A-11D. Note that if profile samples 1338 are acquired in advance, they need not be acquired again in the authentication steps of FIGS. 11A-11B. It is additionally noted that in one embodiment, the Reader 108 compares the profile samples 1338 of the PDKs 102 to the computed input sample until a match is found before performing a full profile comparison. In one embodiment, the Reader first compares samples from the selected PDK 102 until a match is found. For example, a Reader 108 may have accumulated multiple fingerprint profiles samples 1338 (e.g., corresponding to different fingers) for the selected PDK 102. The Reader 108 receives a fingerprint input from, for example, the left index finger, computes the input sample, and does a quick comparison against the accumulated samples 1338 for the selected PDK 102 to efficiently determine a matching profile. The Reader 108 then performs the full comparison using the matching profile. In an alternative embodiment, the Reader 108 performs a comparison of a first sample from each PDK 102 and if no match is found, performs comparisons of second samples from each PDK 102. It will be apparent to one of ordinary skill in the art that samples can be compared in a variety of other orders without departing from the scope of the invention.

If the authentication test 1308 indicates a valid profile, the transaction is completed 1310 for the matching PDK 102. If the authentication test 1308 determines the profile is invalid, a new differentiation decision 1306 is made to determine the next mostly likely PDK 102 to be associated with the transaction. The process repeats until a valid profile is found or all the PDKs 102 are determined to be invalid.

Figure 14:
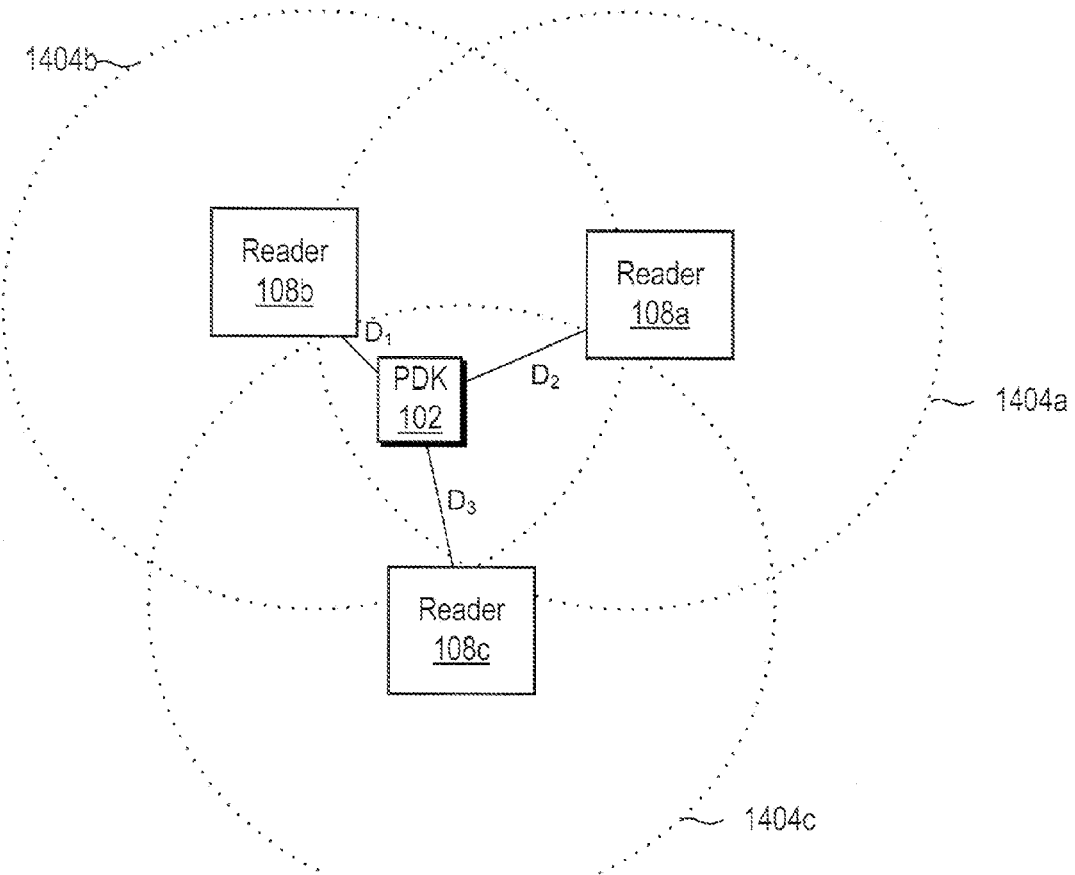
FIG. 14 is a block diagram illustrating an embodiment of a system for estimating location of a PDK using coordinate triangulation.

Turning now to FIG. 14, an example system is illustrated for determining a location metric 1334 of a PDK 102 using a coordinate triangulation technique. In one embodiment of coordinate triangulation, multiple transmitting devices (e.g., Readers 108a-c) are spaced throughout an area. In one embodiment, the Readers 108a-care coupled by a network. Each Reader 108a-c has a range 1404 and the ranges 1404 overlap. Each Reader 108a-c determines a distance D1-D3 between the Reader 108 and the PDK 102. Distance may be estimated, for example, by monitoring signal strength and/or bit error rate as previously described. Then using conventional trigonometry, an approximate location of the PDK 102 can be calculated from D1-D3. Although only three transmitters are illustrated, it will be apparent that any number of transmitters can be used to sufficiently cover a desired area. Location information can be computed at predetermined time intervals to track the movement of PDKs throughout a facility.

Figure 15:
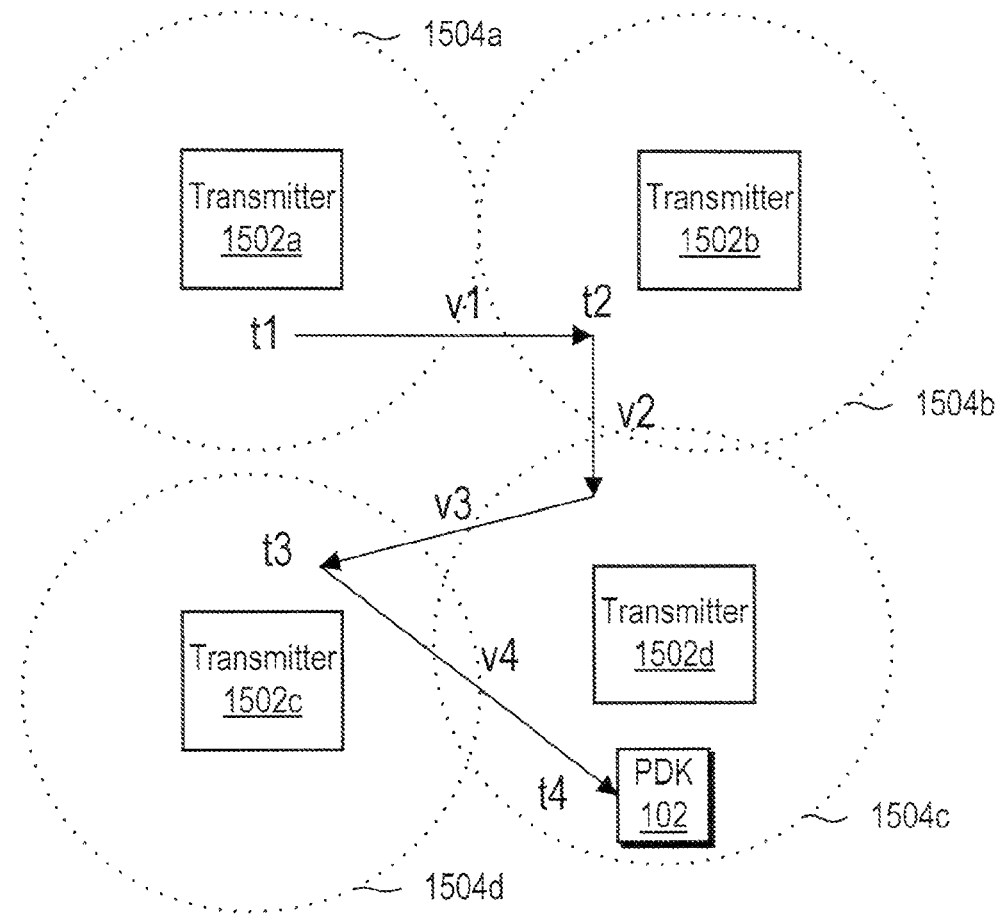
FIG. 15 is a block diagram illustrating an embodiment of a system for location tracking of a PDK.

Another embodiment of location tracking is illustrated in FIG. 15. Here, transmitters 1502 having ranges 1504 are distributed throughout an area. The ranges 1504 can vary and can be overlapping or non-overlapping. In this embodiment, each transmitter 1502 can detect when a PDK 102 enters or exists its range boundaries 1504. By time-stamping the boundary crossings, a location vector can be determined to track the PDK's movement. For example, at a first time, t1, the PDK 102 is detected within the range of transmitter 1502a. At a second time, t2, the PDK 102 is detected within the range of transmitter 1502b. At a third time, t3, the PDK 102 is within the range of transmitter 1502c and at a fourth time, t4, the PDK 102 is within the range of transmitter 1502d. Using the location and time information, approximate motion vectors, v1, v2, v3, and v4 can be computed to track the motion of the PDK 102 without necessarily computing exact distance measurements.

Figure 16:
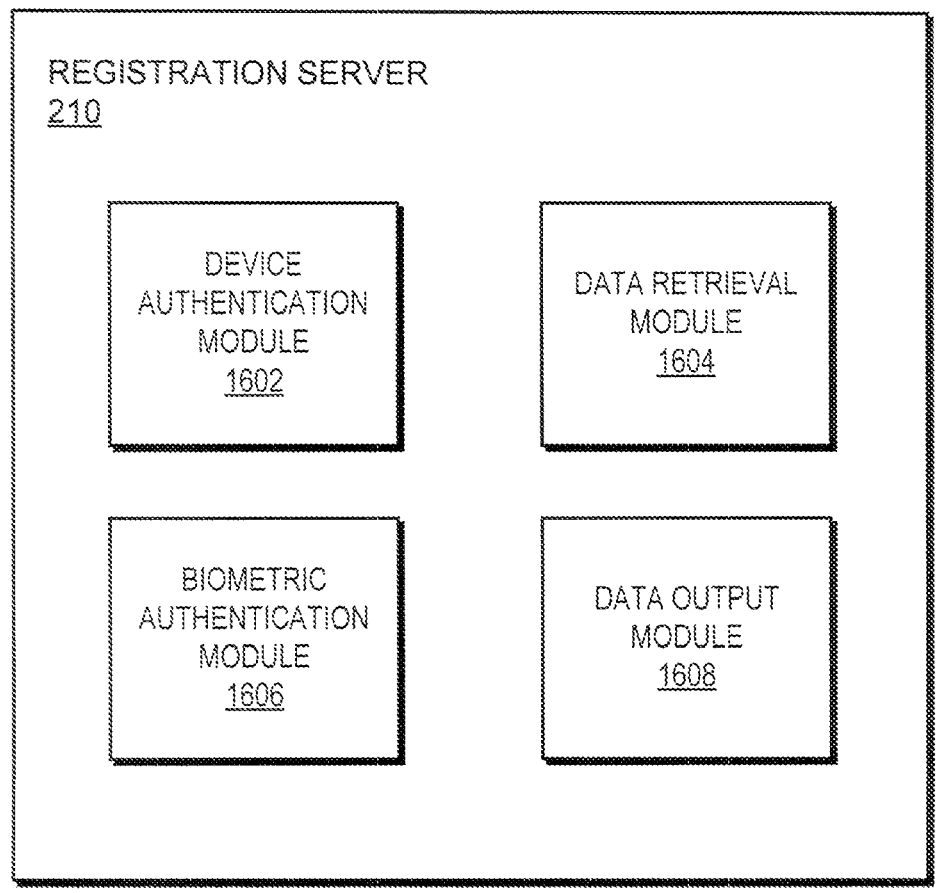
FIG. 16 is a block diagram illustrating an embodiment of a registration server.

FIG. 16 is a block diagram illustrating an embodiment of registration server 210. The registration server 210 includes software routines for automating the process of registering new patients and ensures that a patient never needs to register more than once. The registration server 210 includes a device authentication module 1602, data retrieval module 1604, biometric authentication module 1606 and data output module 1608. The device authentication module 1602 receives PDK information sent by a Reader 108 and is coupled to the biometric authentication module, which receives biometric data from the PDK 102 and performs biometric authentication. The device authentication is also coupled to the data retrieval module 1604. By automating patient registration, the registration server 210 saves time and expense as well as reduces errors and patient frustration.

Figure 17:
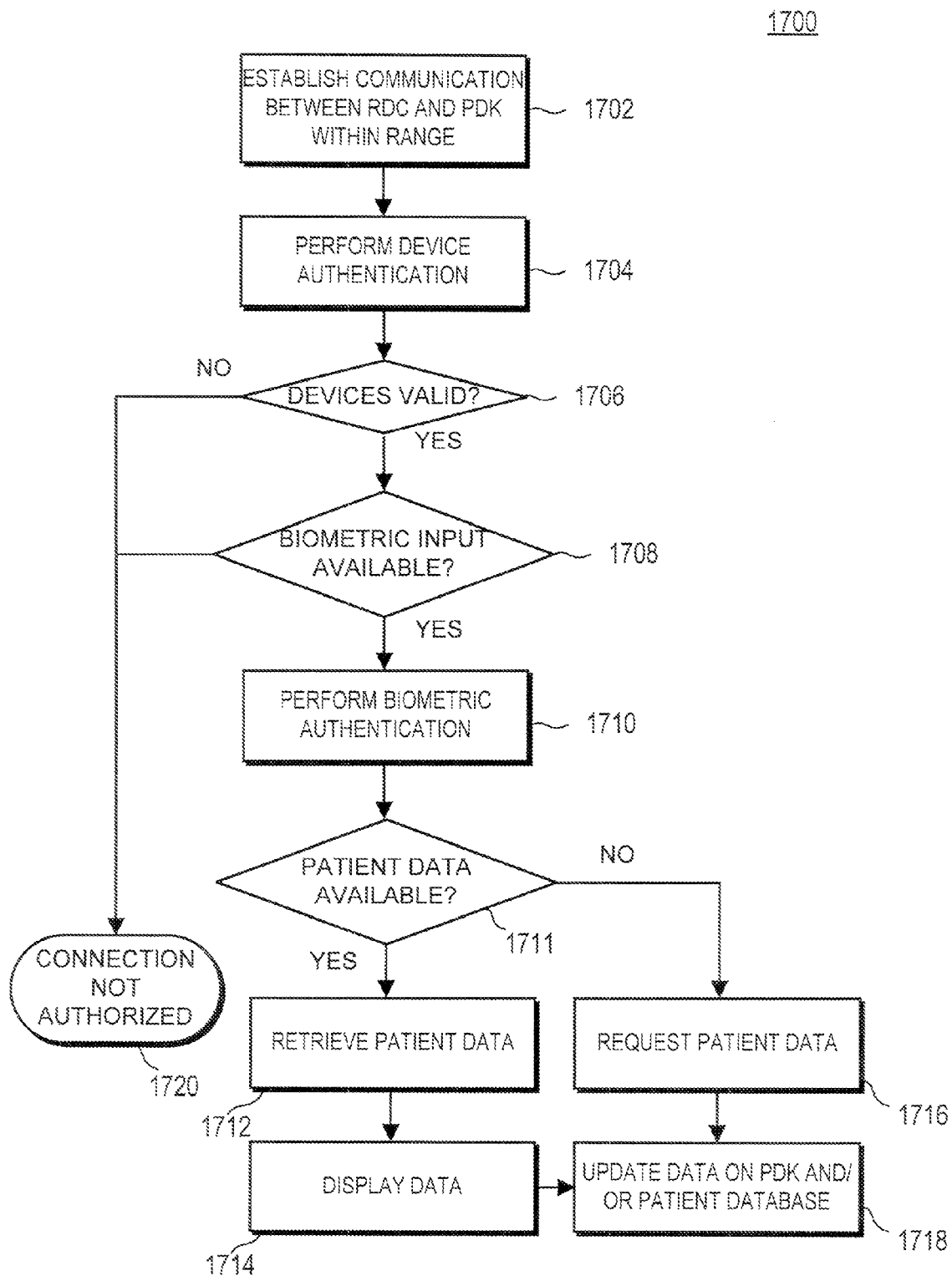
FIG. 17 is a flowchart illustrating one embodiment of a process for automatic patient registration.

FIG. 17 is a flowchart illustrating one embodiment of a process 1700 for automatic patient registration. When a patient carrying or wearing a PDK comes within the range of a Reader 108, communication is automatically established 1702 between the RDC 604 of the Reader 108. Once communication with the PDK 108 is established, device authentication 1704 is performed.

In one embodiment, the device authentication module 1602 performs 1704 device authentication. In another embodiment, the device authentication is performed by the Reader 108 as described in step 804 of FIG. 8. An example embodiment of a method for performing 1704 device authentication is illustrated in the previous FIG. 9.

Next, the device authentication module 1602 determines 1706 whether the PDK 102 is valid. If the PDK 102 is found to be invalid (1706-No), a connection is not authorized 1720 and the process ends and without automatic registration of the patient. However, if the PDK 102 is found to be valid (1706-Yes), the biometric authentication module 1606 determines 1708 whether biometric input is available and performs 1710 biometric authentication. In one embodiment, a patient provides biometric information by swiping their finger on a Reader 108. In another embodiment, the patient provides biometric information by swiping their finger on the biometric reader 470 of the PDK 102. If biometric information is not available (the patient has not swiped his finger or entered a PIN number), connection is not authorized 1720 and the process ends. If biometric information is available, biometric authentication is performed 1710. Example embodiments for performing biometric authentication are described in FIGS. 11A-D. Those skilled in the art will recognize that depending on the level of authentication desired, the need for steps 1708 and 1710 may be omitted. In other words, for routine procedures like a physical, biometric authentication is not required, while for other more invasive, complex and expensive procedures, biometric authentication is required.

Once biometric authentication is performed 1710, the data retrieval module 1602 of the registration server 210 retrieves information from the PDK 102 to determine 1711 whether patient information is available on the PDK 102. In some embodiments, patient core data is stored in the PDK 102. Patient core data includes some or all of the following information: the patient's name, social security number, emergency contacts, demographics, advanced directives, past medical and surgical history, family and social history, pharmacy contact information, medical insurance information, photo, software application serial number, and other information uniquely identifying the patient. If patient data is available (1711-Yes), the patient data is retrieved 1712 from the PDK 102 and displayed 1714 on the display 718 of the provider interface device 120. The health care provider can then review or update the information as needed. During the patient's visit, new information may be generated. While the PDK 102 is in range, e.g. in the doctor's office, the Reader 108 sends signals to the PDK 102 and the new information is automatically saved 1718 to the patient's PDK. In one embodiment, the new information is also saved to the Central Registry 114 and Private Registries 116a, 116b of the local services module 124. If patient data is not available (1711-No), the registration module 210 requests 1716 patient data. Patient data may then be entered via the provider interface device 120. Once data is entered, the information is saved 1718 to the PDK 102 and/or Central Registry 114 and Private Registries 116.

For example, when a patient enters a provider's facility, the process 1700 described above allows the patient to walk up to the registration table and simply swipe a finger on a biometric reader to check-in for an appointment. This replaces the cumbersome process of the traditional patient check-in procedure with a simple finger swipe, therefore improving patient experience, minimizing entry errors and lowering labor costs.

As another example, when a patient is being examined by a provider, the process 1700 described above allows the patient's retrieved core data to be automatically displayed on the provider interface device 120 in the examining room, operating room or emergency room, therefore making the patient's information easily accessible during examinations, surgery preparation or emergency room treatment.

Figure 18:
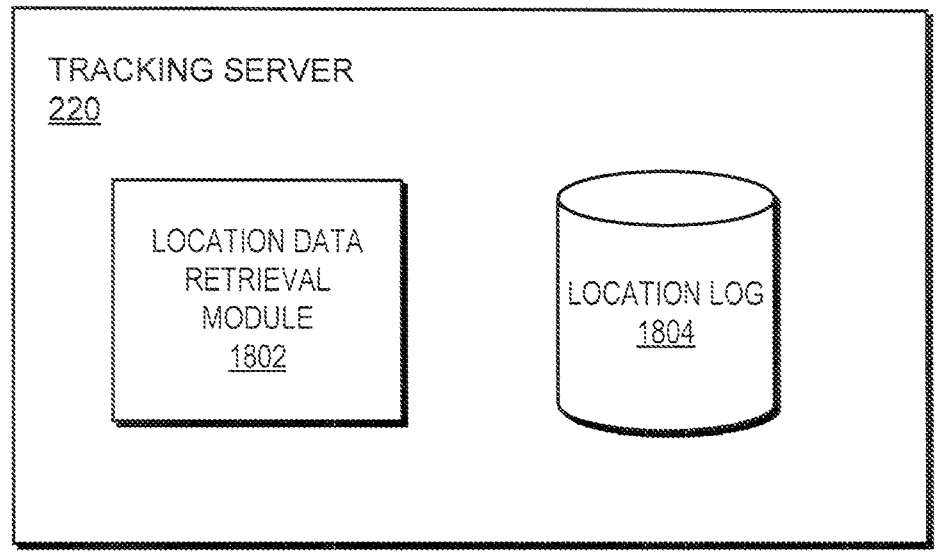
FIG. 18 is a block diagram illustrating an embodiment of a tracking server.

FIG. 18 is a block diagram illustrating an embodiment of a tracking server 220. The tracking server 220 enables real-time tracking of individuals, equipment and supplies by monitoring and storing location information of individuals, equipment or supplies with associated PDKs. Providers can be located immediately in case of an emergency. Location of patients can be monitored to ensure timely administration of medications. Additionally, location of equipment and supplies can also be constantly monitored therefore minimizing search time and inventory surplus requirements. One embodiment of the tracking server 220 includes a location data retrieval module 1802 and a location log. In one embodiment, the location log is a database, such as a Structured Query Language (SQL) database.

In one embodiment, multiple Readers 108 are placed at certain and known positions throughout the healthcare facility. For example, a Reader is placed above each doorway of every room and at every provider interface device 120. In another embodiment, Readers 108 are placed in a grid pattern throughout the healthcare facility. In one embodiment, every provider carries associated PDK uniquely identifying the provider and PDKs are attached to each piece of equipment and every cart of supplies. Example embodiments of a tracking system are described in U.S. patent application Ser. No. 11/939,451 to John Giobbi, et al., entitled "Tracking System Using Personal Digital Key Groups" filed on Nov. 13, 2007, the entire contents of which are incorporated herein by reference.

Figure 19A:
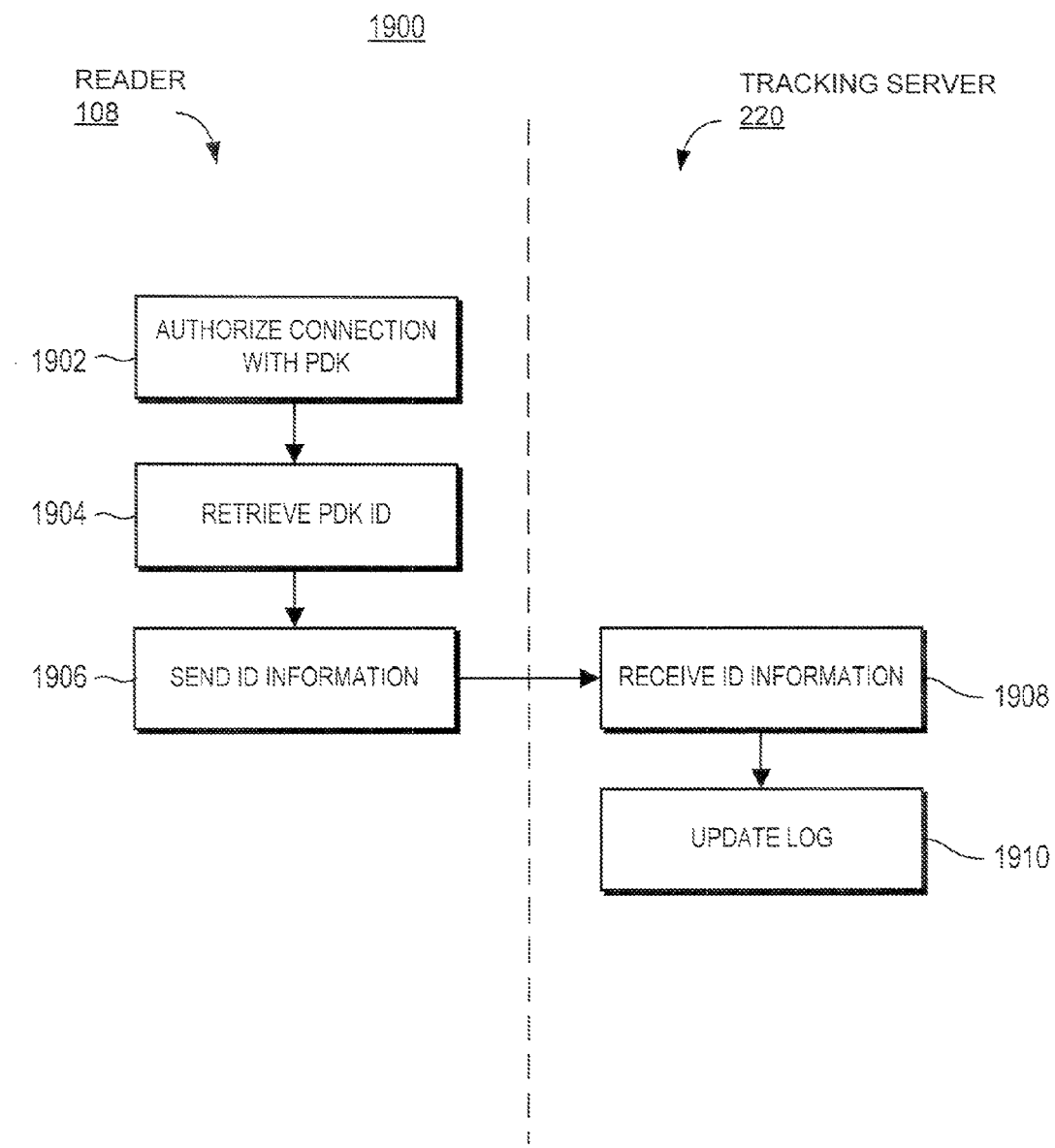
FIG. 19A is a flowchart illustrating one embodiment of a process for tracking of equipment and individuals.

A flowchart illustrating one embodiment of a process 1900 for tracking of equipment and individuals is shown in FIG. 19A. When a PDK comes within the range of a Reader 108, connection is authorized 1902 between the RDC 604 of the Reader 108 and the PDK 102. In one embodiment, the RDC 604 continually transmits beacons that are detected by the PDK 102 when it enters a proximity zone of the Reader 108. In an alternative embodiment, the communication is instead initiated by the PDK 102 and acknowledged by the Reader 108. As shown in the previous FIG. 8, device authentication is first performed and once the Reader 108 establishes if the PDK 102 is a valid device and PDK 102 establishes if the Reader 108 is valid, connection can be authorized.

Once connection is authorized 1902, the Reader 108 retrieves 1904 the PDK 102 information, such as PDK ID 412 and other information identifying the owner or entity associated with the PDK 102. In one embodiment, the reader ID 618 of the Reader 108 is sent to the PDK 102 and stored in the activity log 490 of the PDK 102. The reader and PDK information is sent 1906 to the tracking server 220. The location data retrieval module 1802 receives 1908 the information, including the PDK ID 412. The information is updated 1910 in the location log 1804 of the tracking server 220.

In one embodiment, the location log data is retrieved by the provider interface device 120. In such embodiments, the provider interface device 120 displays the locations of the individuals and equipment being tracked; therefore making it possible to locate anyone and any piece of equipment at any given moment. In some embodiments, the location log data is displayed graphically, for example, with a map of the facility and indications on the map identifying locations of tracked items and people. In other embodiments, the location log data is displayed on the provider interface device 120 with text describing the locations of the tracked items and people.

Figure 19B:
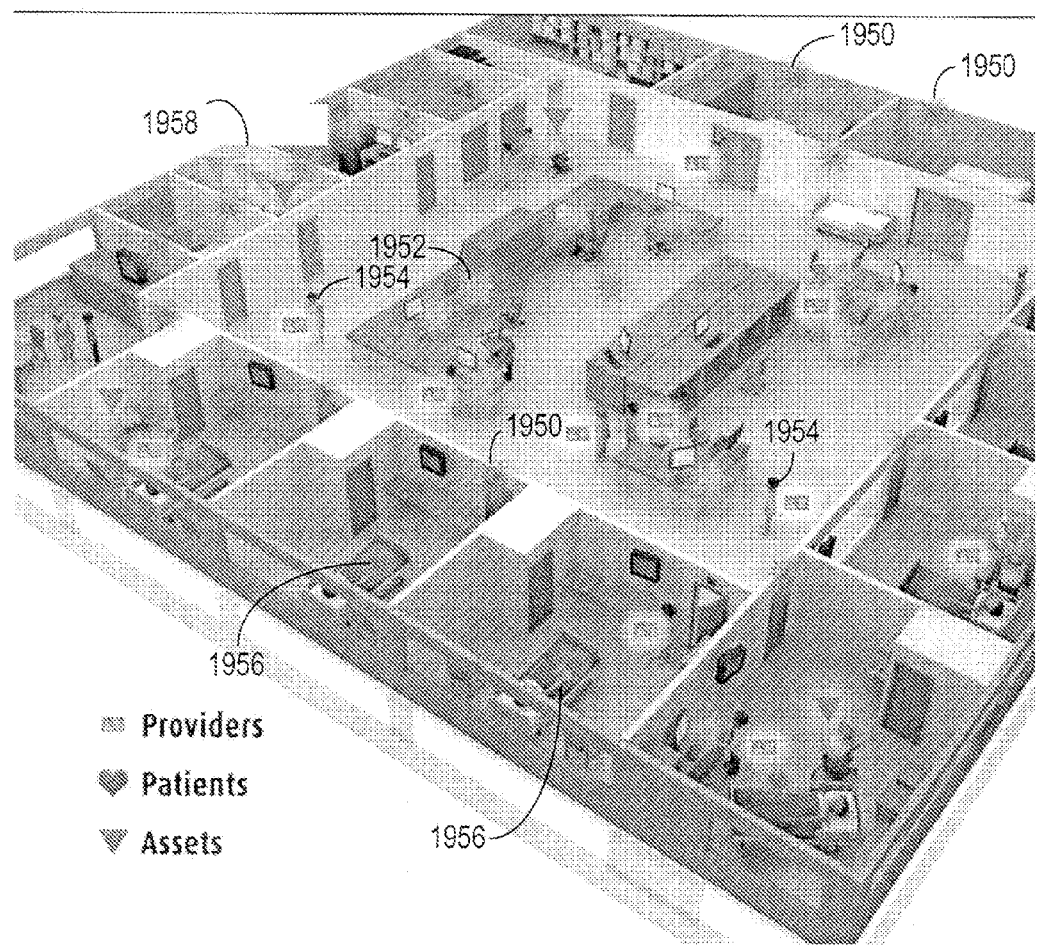
FIG. 19B is a graphical representation illustrating a patient, provider and equipment tracking within a healthcare facility.

This process 1900 occurs whenever a PDK 102 enters the proximity zone of each Reader 108 that it passes enabling constant tracking and location of individuals carrying PDKs and equipment with affixed PDKs. FIG. 19B is a graphical representation illustrating a patient, provider and equipment tracking within a healthcare facility. Readers 1950 are located at various locations throughout the healthcare facility to receive PDK information. Provider interface devices are also equipped with readers 1952 for receiving PDK information. The Readers 1950 and 1952 receive information from the provider PDKs 1954, patient PDKs 1956 and equipment PDKs 1958 enabling the location and tracking of providers, patients and equipment anywhere throughout the healthcare facility.

Figure 20:
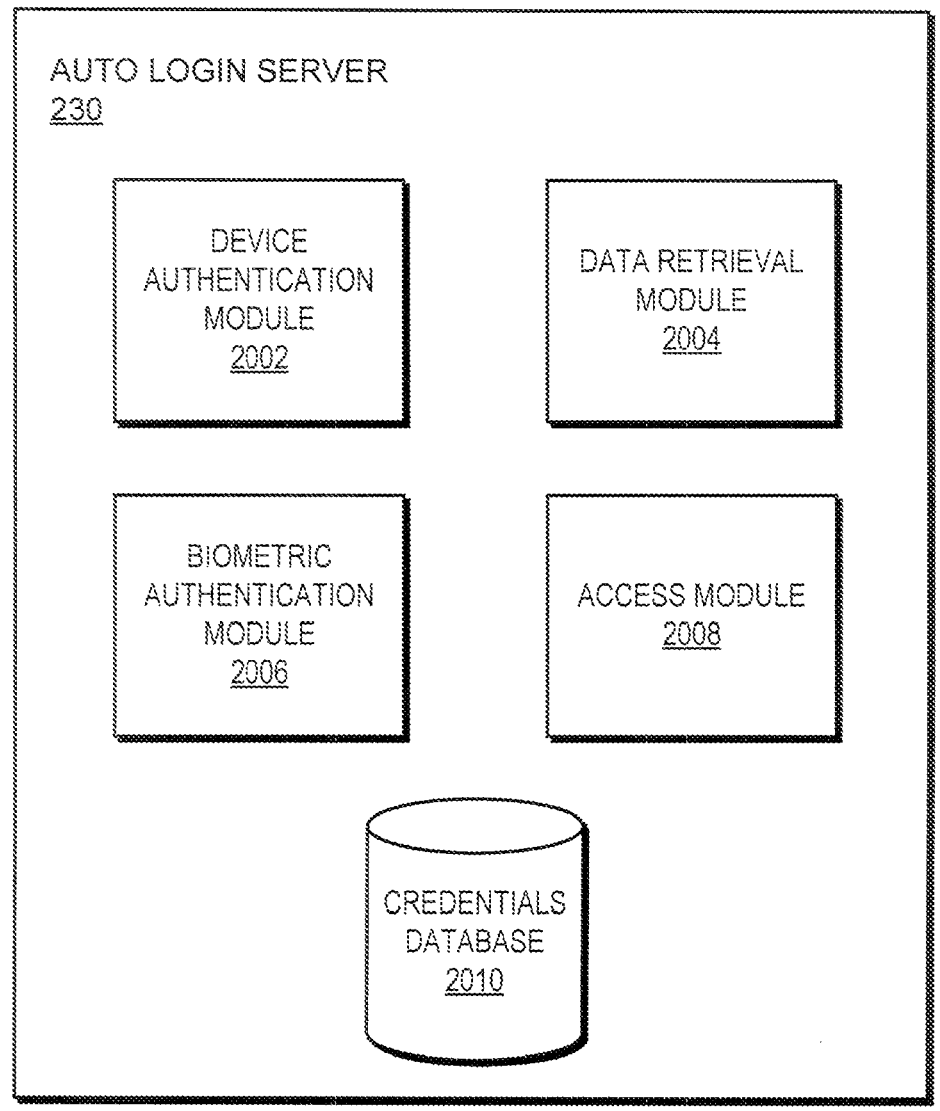
FIG. 20 is a block diagram illustrating an embodiment of an auto login server.

FIG. 20 is a block diagram illustrating an embodiment of an auto login server 230. The auto login server 230 allows for automated electronic signing on of providers into the healthcare computer system, therefore eliminating the constant and time-consuming login and logout of healthcare providers such as doctors, nurses, physician assistants, medical technicians, and other caregivers. In one embodiment, providers can utilize their PDKs to automatically log in to the application software system by simply approaching or entering the proximity zone of a Reader 720 of a provider interface device 120. In such embodiments, no manual input is necessary. The auto login server 230 includes a device authentication module 2002, a data retrieval module 2004, a biometric authentication module 2006, an access module 2008 and a credentials database 2010. In some embodiments the auto login server resides in the local services module 124. The auto login server includes input and output ports for receiving data from and sending data to Readers 108. The device authentication module 2002 is coupled to the biometric authentication module 2006 and data retrieval module 2004. The data retrieval module is couple to communicate with the access module, which is further configured to send access authorization to readers 720, 108 and provider interface device 120.

Figure 21A:
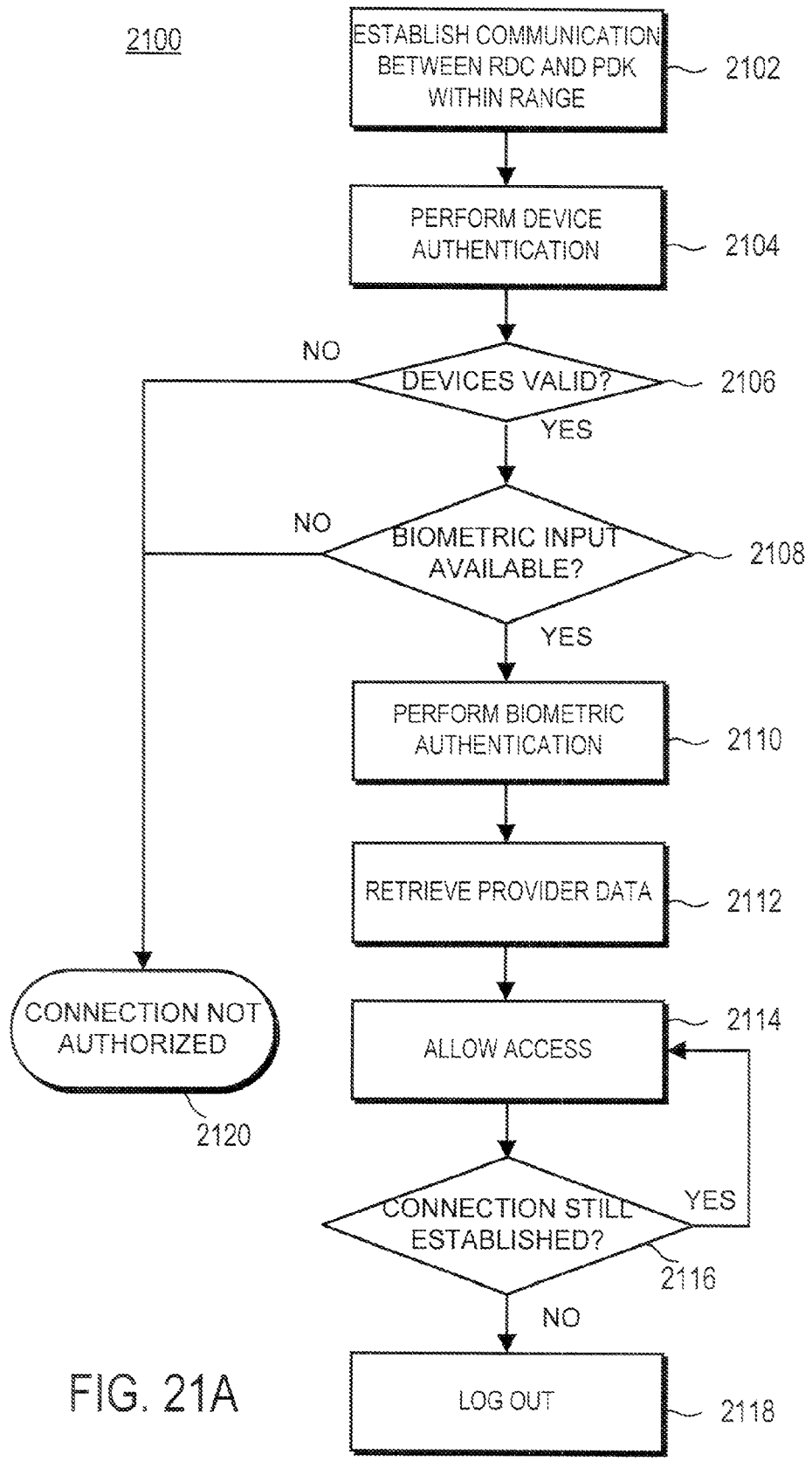
FIG. 21A is a flowchart illustrating one embodiment of a process for automatic login of providers.

FIG. 21A is a flowchart illustrating one embodiment of a process 2100A for automatic login of providers. When a provider carrying or wearing a PDK 102 comes within the range of a Reader 720 of a provider interface device 120, communication is automatically established 2102 between the RDC 604 of the Reader 720 of a provider interface device 120. In one embodiment, the PDK 102 is incorporated into an identification badge of the provider. Once communication with the PDK 108 is established, device authentication is performed 2104.

In one embodiment, the device authentication module 2002 performs 2104 device authentication. In another embodiment, the device authentication is performed by the Reader 108 as described in step 804 of FIG. 8. An example embodiment of a method for performing 2104 device authentication is illustrated in the previous FIG. 9.

Next, the device authentication module 2002 determines 2106 whether the PDK 102 is valid. If the PDK 102 is found to be invalid, connection is not authorized 2116 and the process ends without the logging in of the provider.

If the PDK is found to be valid, the biometric authentication module 2006 determines 2106 if biometric information is available. If biometric information is available, the biometric authentication module 2006 performs 2110 biometric authentication. In one embodiment, a provider provides biometric information by swiping their finger on a Reader 108 of the provider interface device 120. In another embodiment, the provider provides biometric information by entering a PIN number. In yet another embodiment, the provider provides biometric information be swiping their finger on the biometric reader 470 of the PDK 102. If biometric information is not available (the provider has not swiped his finger or entered a PIN number), connection is not authorized 2120 and the process ends. If biometric information is available, biometric authentication is performed 2110. Example embodiments for performing biometric authentication are described in FIGS. 11A-D.

Once biometric authentication is performed 2110, the data retrieval module 2004 of the registration server 210 retrieves information from the PDK 102 of the provider and the access module 2008 allows 2114 access into the healthcare software application system. In some embodiments where biometric authentication is not required, the access module 2008 compares the received data with data stored in the credentials database 2010 to allow or deny access.

In one embodiment, when a login window appears on the provider interface device 120, the medical services application 730 of the provider interface device 120 orchestrates the retrieval of the login credential information from the PDK 102 of the provider and enters the log in information into the login window. In another embodiment, when a login window appears on the provider interface device 120, the medical services application 730 of the provider interface device 120 orchestrates the retrieval of the login credential information from the credentials database 320 and enters the log in information into the login window In some embodiments, provider identifying information is stored in the PDK 102. As long as connection is established (2116-Yes) (the provider is in the proximity zone of the reader 720 of the provider interface device 120), access is allowed 2114. If the provider steps outside the proximity zone of the reader 720, connection is no longer established (2116-No) and the provider is logged out 2118 of the healthcare software application system. Those skilled in the art will recognize that depending on the level of authentication desired, the need for steps 2108 and 2110 may be omitted.

In some embodiments, various rules are applied. In one embodiment, biometric input is required for users who haven't logged in for an extended period of time. In one embodiment, the extended period of time is eight hours. In another embodiment, the extended period of time is twenty four hours. In one embodiment, a secure screen saver is utilized in place of a full login/logout procedure. In another embodiment, the system allows for multiple users to be simultaneously logged in to a single workstation.

Figure 21B:
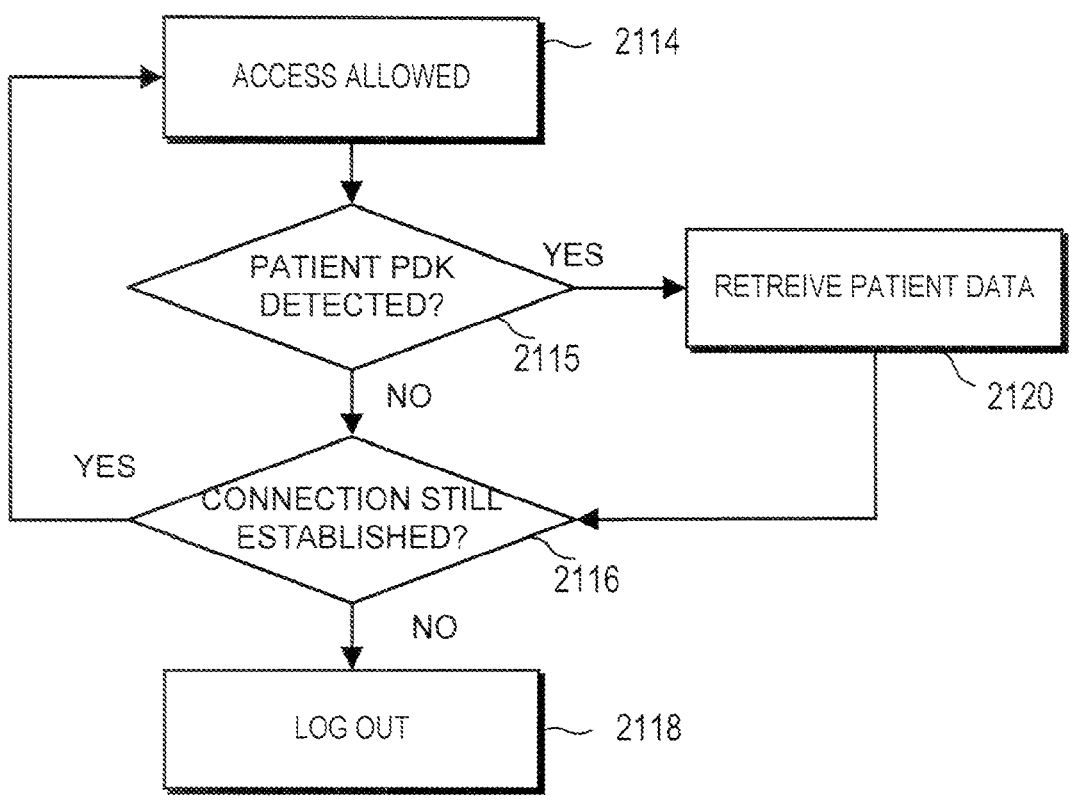
FIG. 21B is a flowchart illustrating another embodiment of a process for automatic login of providers.

FIG. 21B is a flowchart illustrating one embodiment of a process 2100B for automatic login of providers. The steps 2102-2114 of FIG. 21A are the same with the embodiment shown in FIG. 21B. This embodiment allows automatic login when a provider enters an examination room. Once access is allowed 2114, a determination 2115 is made as to whether a patient's PDK is detected, i.e. a patient is waiting in the exam room waiting to be examined. If a patient's PDK is detected (2115-Yes), the patient's data is retrieved 2120. As described above in FIG. 21A, the provider remains logged in as long as connection is still established (2116-Yes). If the patient's PDK is not detected (2115-No), patient data is not retrieved and the provider simply remains logged in as long as connection is established (2126-Yes).

In some embodiments, if the provider makes any changes or annotations to the patient's information while being logged into the system, a notation will be recorded in the patient's information that the particular provider made the change or annotation. This enables accurate tracking of recorded patient data and accountability for patient care.

Figure 21C:
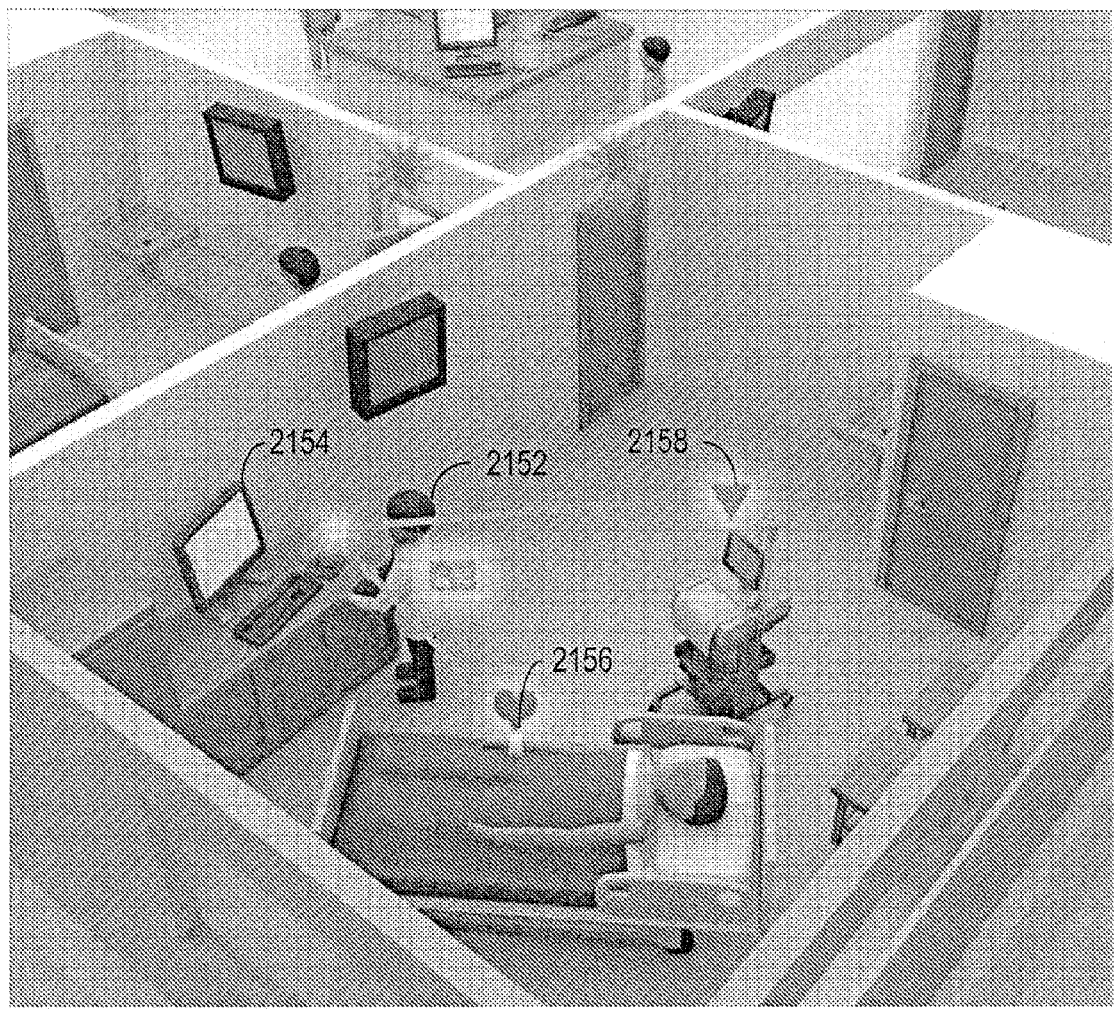
FIG. 21C is a graphical representation of one embodiment of automatic login of providers.

FIG. 21C is a graphical representation of one embodiment of automatic login of providers. In this illustration, a provider 2152 with a unique identifying PDK enters a patient's room and walks up to a provider interface device 2154. The reader of the provider interface device 2154 retrieves information from the provider's 2152 PDK and automatically logs the provider 2152 into the software system. The reader of the provider interface device 2154 also retrieves information from the PDKs 2156 and 2158 of the patient and equipment. The patient's information is then displayed on the provider interface device 2154. In some embodiments, whenever a logged in provider enters or edits a patient's information on the provider interface device 2154, an annotation is made identifying the logged in provider as the user who has made the additions or edits to the patient's information.

Figure 22:
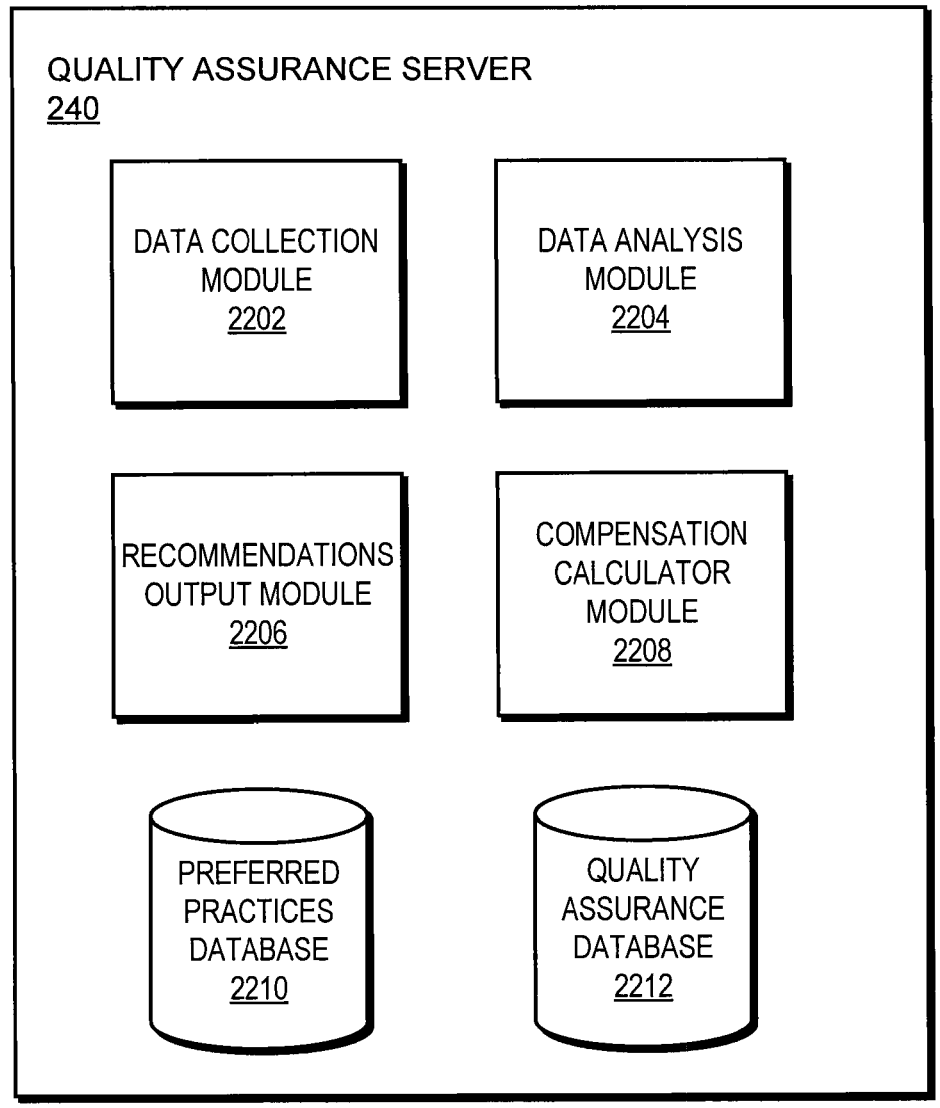
FIG. 22 is a block diagram illustrating an embodiment of a quality assurance server.

FIG. 22 is a block diagram illustrating an embodiment of a quality assurance server 240. The quality assurance server 240 provides recommendations for improving patient care by monitoring patient treatment and provider activity. The quality assurance server 240 includes input and output ports to send and receive data from PDK 102 via the Reader 108 and is also configured to send and receive data from the provider interface device 120. The quality assurance server 240 includes a data collection module 2202, a data analysis module 2204, a recommendations output module 2206, a compensation calculator module 2208, a preferred practices database 2210 and a quality assurance database 2212. The data collections module 2202 is configured to receive data from the Reader 108 and provider interface device 120 and send the data to the data analysis module 2204. The data analysis module 2204 is coupled to the recommendations output module 2206, the compensation calculator module 2208, a preferred practices database 2210 and the quality assurance database 2212. The recommendations output module 2206 is configured to send to the provider interface device 120 and the PDK 102 via the Reader 108.

Figure 23:
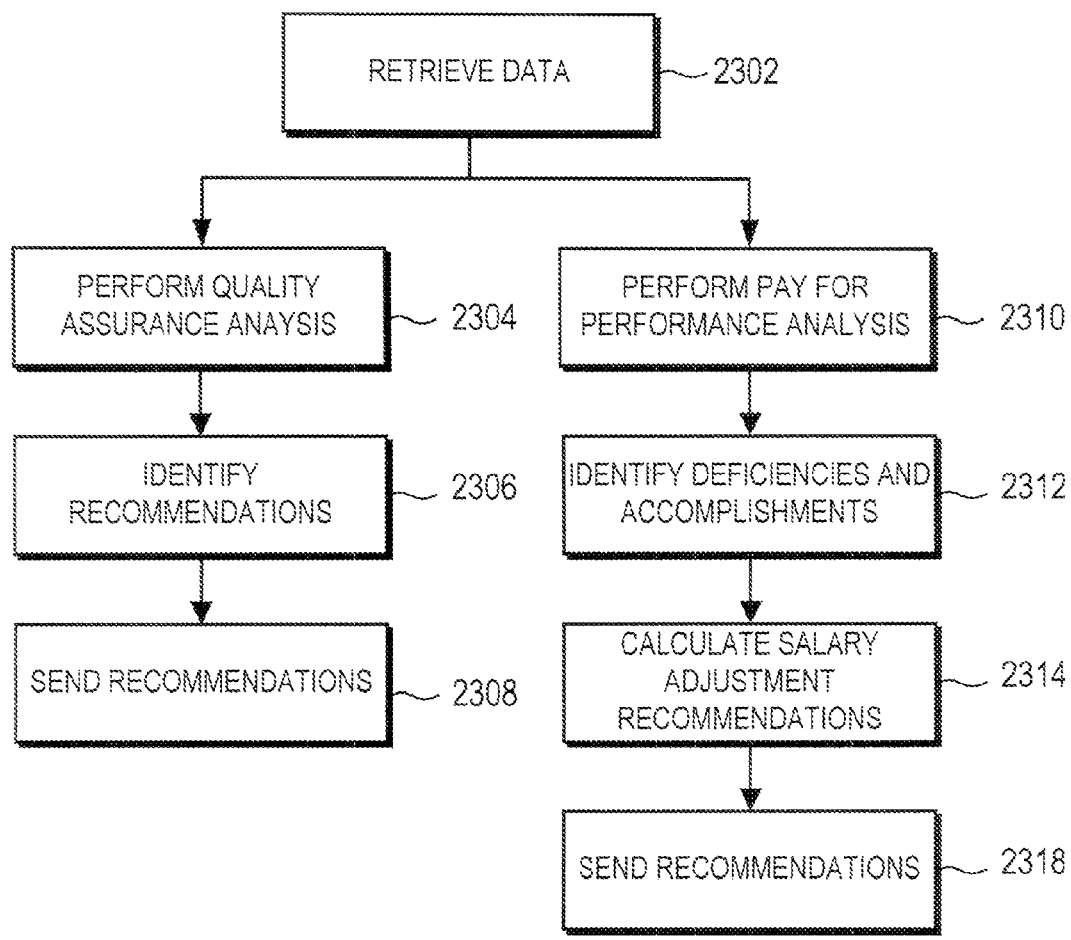
FIG. 23 is a flowchart illustrating one embodiment of a process for analyzing patient care and provider performance.

FIG. 23 is a flowchart illustrating one embodiment of a process 2300 for analyzing patient care and provider performance. The data collection module 2202 retrieves 2302 data from the patient's profile information. In one embodiment, the retrieved data includes the patient's treatment history, prescribed and administered medications, number of doctor's visits, and other information related to the current care and treatment of the patient. In one embodiment, the data is retrieved from the activity log 490 of the patient's PDK 102. A quality assurance analysis is performed 2304 on the data to ensure the optimal care for the patient. The retrieved data is compared with the standards and preferred practices stored in the preferred practices database 2210. The preferred practices database stores standards and preferred practices that define the optimal or recommended care appropriate for a given condition, service or treatment. Recommendations are identified 2306 and sent 2308 to the patient's profile for display on the provider interface device 120. For example, if the comparison of the received data from the activity log 490 shows that correct procedures and treatments have been administered, then this is recorded and stored in the activity log 490 for later use. In some embodiments, the compared information is stored in the quality assurance database 2212.

In another embodiment, analysis of the provider's performance is done 2310 to calculate effect on the provider's compensation. The log which stores the provider's rounds and various treatments given is analyzed and also compared to preferred practices stored in the preferred practices database 2210. Deficiencies and accomplishments are identified 2312. Appropriate salary adjustment is calculated 2314 and recommendations are sent 2318 to affect the provider's compensation.

To illustrate the above in an example, the preferred practices dictates that an admitted patient needs to be visited by his or her provider every four hours, three times a day. Each time a provider visits a patient, information is sent to the patient's PDK 102 and provider's PDK 102 and stored in the activity log 490. The activity data is retrieved 2302 be the data collection module 2202 of the quality assurance server 240. A quality assurance analysis is performed 2304 and monitored data from the activity log 490 is compared with the preferred practices stored in the preferred practices database 2210. In this example, the activity log 490 provides evidence that the doctor only visited the patient two times in one day. Since the preferred practices dictate that the patient should be seen three times, recommendations for more frequent visits are identified 2306 and sent 2308 to the patient's profile for display on the provider interface device 120.

Further, an analysis of the provider's performance is done 2310 to calculate effect on the provider's compensation. Deficiencies in the provider's care are identified 2312 and the appropriate salary adjustment is calculated 2314 and recommendations are sent 2318 to affect the provider's compensation.

Figure 24:
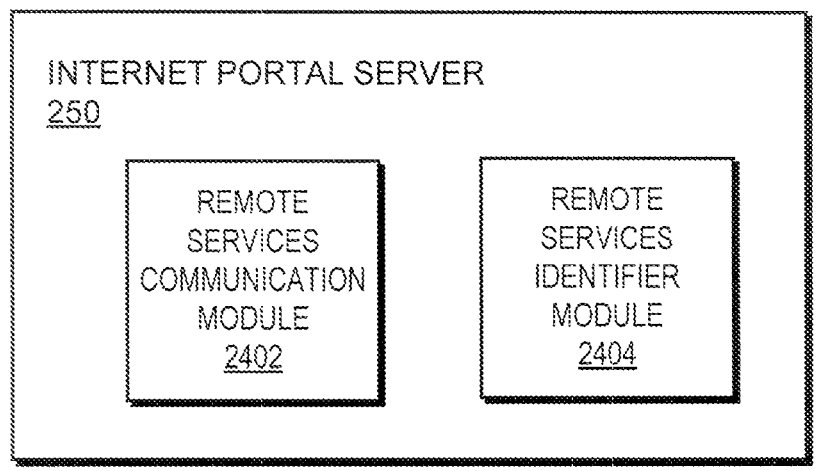
FIG. 24 is a block diagram illustrating an embodiment of an internet portal server.

FIG. 24 is a block diagram illustrating an embodiment of an internet portal server 250. The internet portal server 250 provides a consistent interface to the third party link module 126. Such services may include accessing a patient's virtual database records or insurance information or sending prescription requests to remote pharmacies. The internet portal server 250 includes a remote services communication module 2402 and a remote services identifier module 2404.

Figure 25:
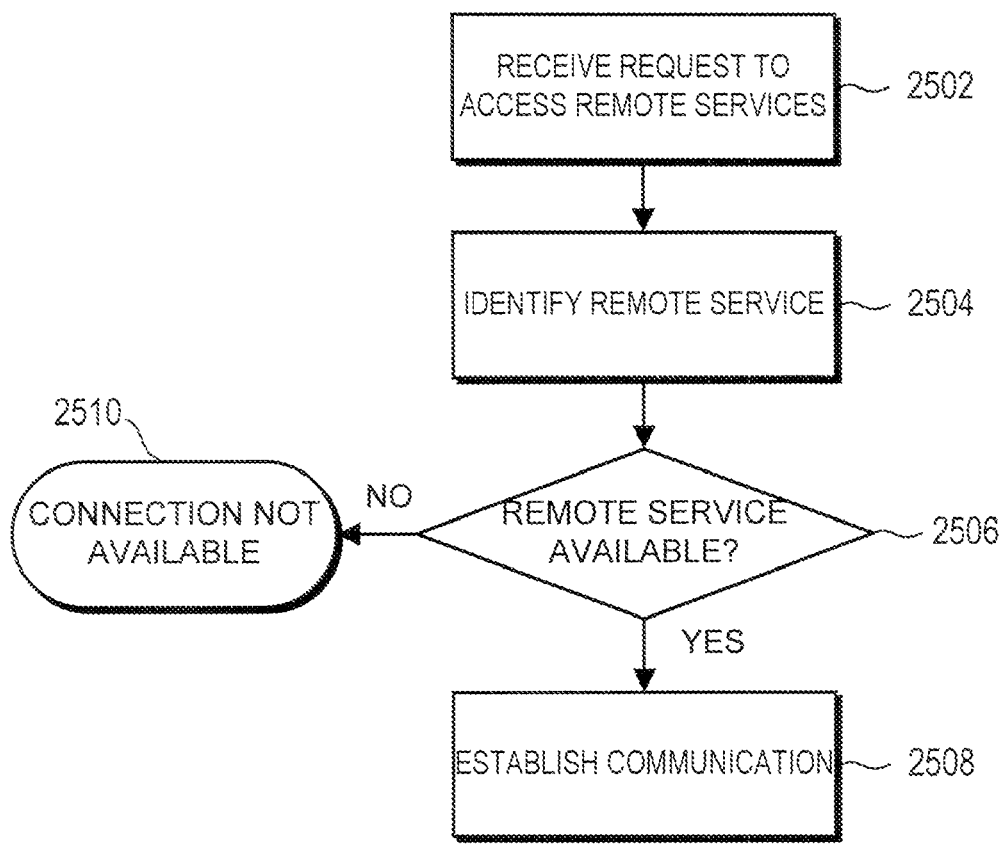
FIG. 25 is a flowchart illustrating one embodiment of a process for communicating with remote services.

FIG. 25 is a flowchart illustrating one embodiment of a process 2500 for communicating with remote services of the third party link module 126. The remote services communication module 2402 receives 2502 a request from a provider interface device 120 to access one of the remote services of the third party link module 126. The remote services identifier module 2404 identifies 2504 which remote service to contact. For example, if the request includes insurance information as well as payment information, the remote services identifier module 2404 determines that the request from the provider interface device 120 needs to communicate with the insurance links server 340 and the billing service server 350.

A determination is then made to determine whether the requested remote service is available 2506. If the remote service is not available (2506-No), then connection is not established. In some embodiments, an error message is sent to the provider interface device 120 with a notification of the unavailability of the requested remote service. If the remote service is available (2506-Yes), communication with that remote service is established 2508.

Figure 26:
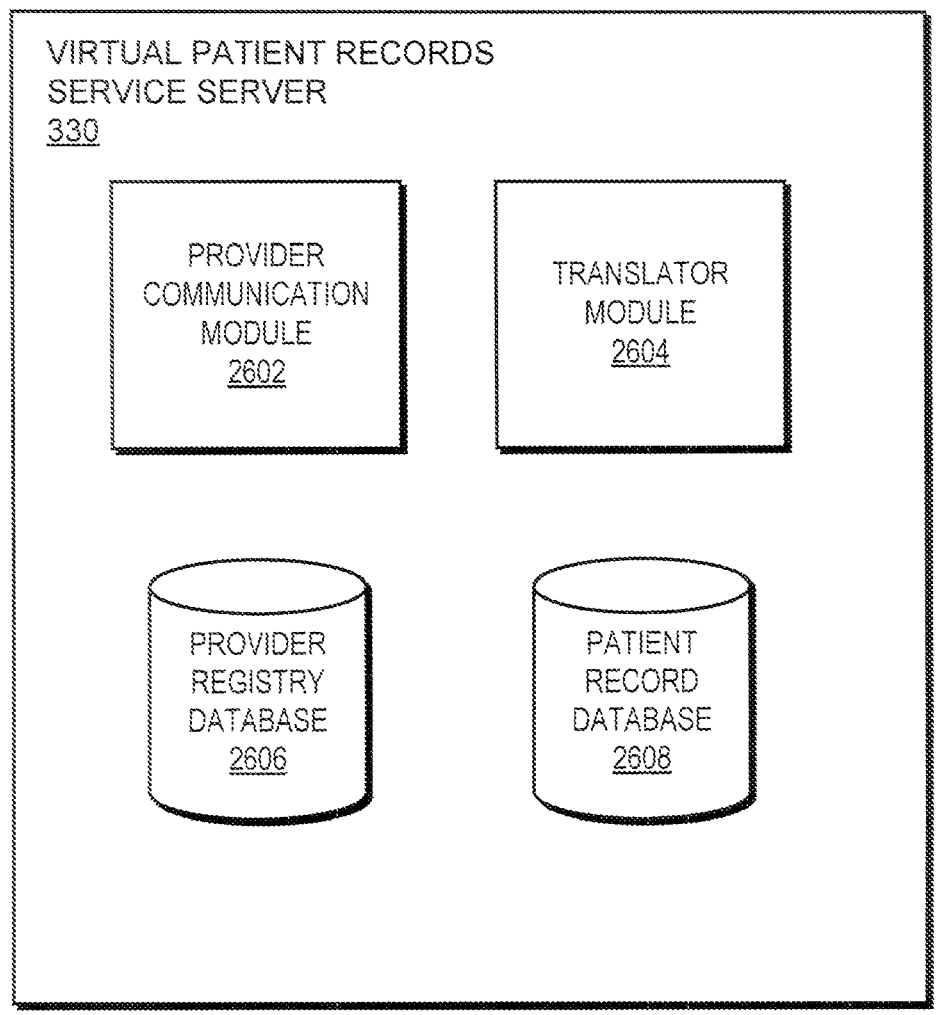
FIG. 26 is a block diagram illustrating an embodiment of a virtual patient records service server.

FIG. 26 is a block diagram illustrating an embodiment of a virtual patient records service server 330. The virtual patient records service server 330 provides a virtual database of a complete record of a patient's medical files by automatically creating links to participating providers' records and enabling centralized and automated access to those records. The virtual patient records service server 330 includes a provider communication module 2602, a translator module 2604, a provider registry database 2606 and a patient records database 2608. The virtual patient records service server 330 includes input and output ports for communicating with the provider interface device 120, the PDK 102 via the Reader 108, and the record system 128. The provider communication module 2602 is configured to receive data from the provider interface device 120 and the PDK 102 via the Reader 108. The provider communication module 2602 is coupled to the translator module 2604, which is coupled to the provider registry database 2606 and patient record database 2608 and configured to send and receive data from the record system 128.

When a patient visits a provider's facility, the patient's medical information may be limitedly available at that provider's facility. Some facilities may store basic information about the patient, such as the patient's name, address, and insurance carrier. However, additional, more detailed information may be needed. The virtual patient records service server 330 provides a seamless link in accessing such detailed information.

The patient records database 2608 stores core data associated with each patient. In one embodiment, core data includes the patient's medical identification number, the patient's provider identification number, medical software information and portal link information. The provider registry database 2606 stores core data associated with particular providers, such as the provider's identification number, the provider's name and contact information. The core data stored in these databases is used to access more detailed information. As described above, the record system 128 is a database for storage of individuals' person health records.

Figure 27:
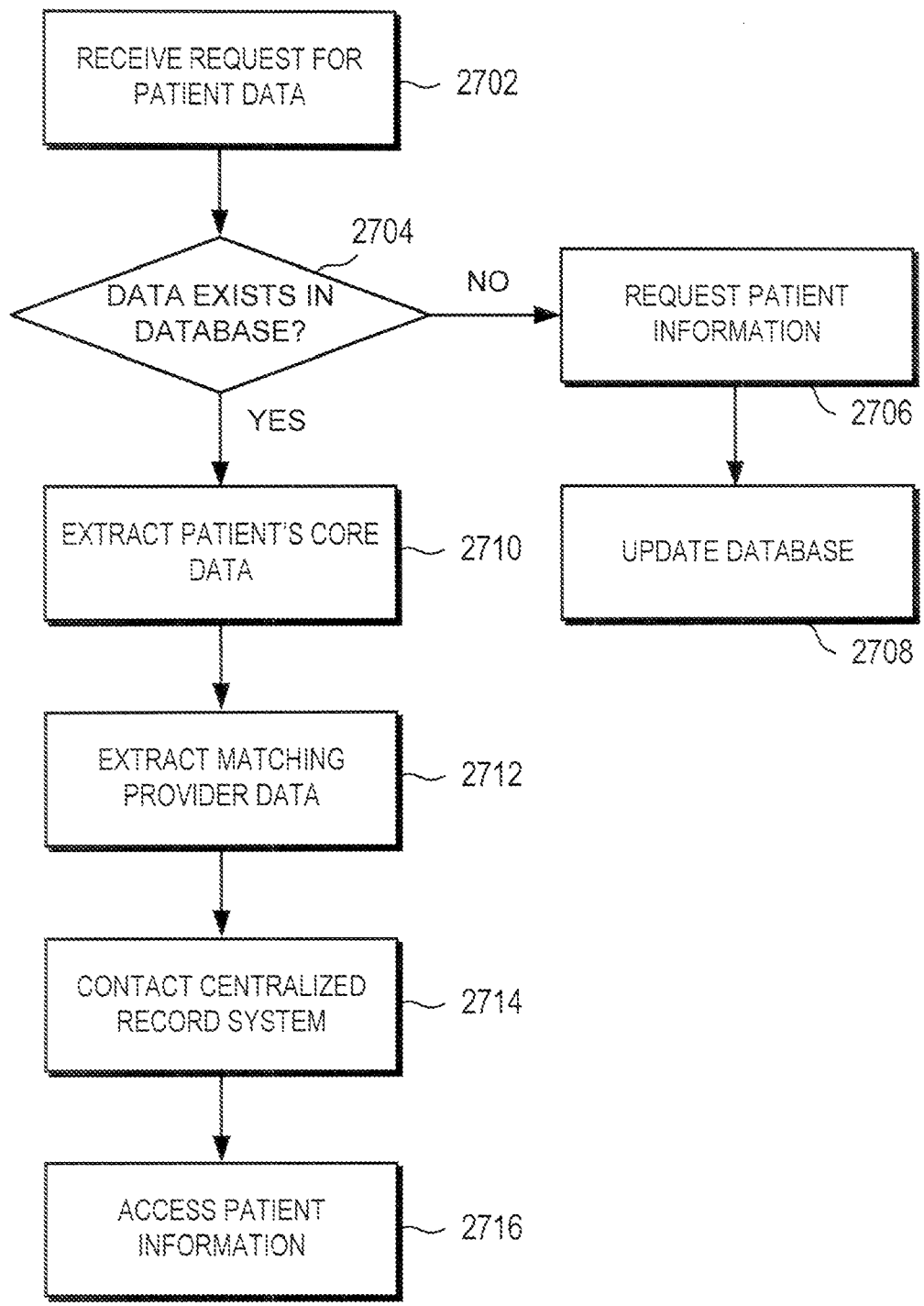
FIG. 27 is a flowchart illustrating one embodiment of a process for accessing virtual patient records.

FIG. 27 is a flowchart illustrating one embodiment of a process 2700 for accessing virtual patient records. The provider communication module 2602 of the virtual patient records service server 330 receives 2702 a request for patient data. A determination 2704 is made as to whether the data exists in the provider registry database 2606 or the patient records database. If the data does not exist (2704-No), patient information is requested 2706 and the provider registry database 2606 and patient records database 2608 are updated and information is stored for later use. The patient information is also sent to the record system 128 for storage. If the data does exist (2704-Yes) in the databases, the patient's core information is extracted from the patient records database 2608 and the corresponding information is extracted 2712 from the provider registry database 2606. The translator module 2604 of the virtual patient records service server 330 interprets the extracted data and contacts 2714 the record system 128. Detailed patient information can then be accessed 2716 from the centralized record system 128.

In one embodiment, any updates and changes stored in the memory 410 of the PDK 102 are sent to the record system 128. In one embodiment, a Reader 108 monitoring the location of an individual's PDK 102 detects when the PDK is about to exit the healthcare facility, for example, if the PDK 102 is approaching a Reader 108 located at a healthcare facility exit, and sends a notification to the virtual patient records service server 330. The virtual patient records service server 330 then instructs the Reader 108 to extract the information from the memory 410 of the PDK 102 and send the information to the records system 128. Similarly, any changes or edits made to the patient's personal health record in the record system 128 is uploaded to the patient's PDK before the patient exits the facility.

Figure 28:
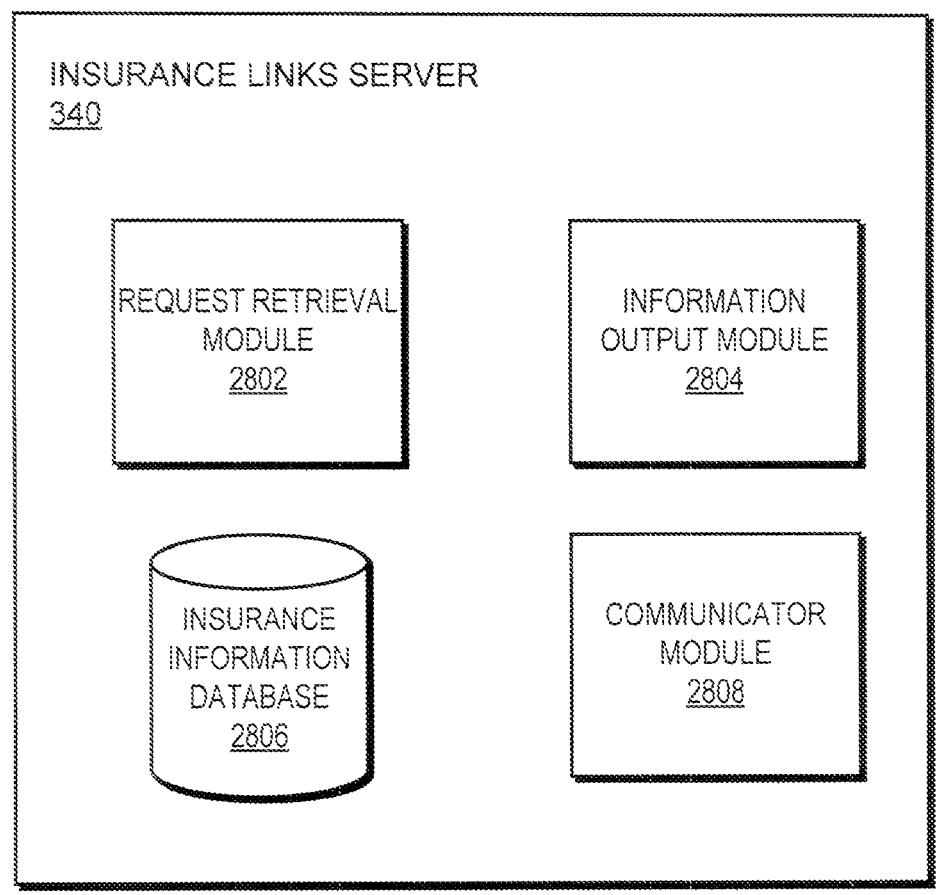
FIG. 28 is a block diagram illustrating an embodiment of an insurance links server.

FIG. 28 is a block diagram illustrating an embodiment of an insurance links server 340. The insurance links server 340 provides a portal of communication between the providers and insurance providers (payors), such as insurance server 144. The insurance links server 340 acts in conjunction with the billing services server 350 to effectively and efficiently update and report patients' billing statements. The insurance links server 340 includes a request retrieval module 2802, an information output module 2804, an insurance information database 2806 and a communicator module 2808.

Figure 29:
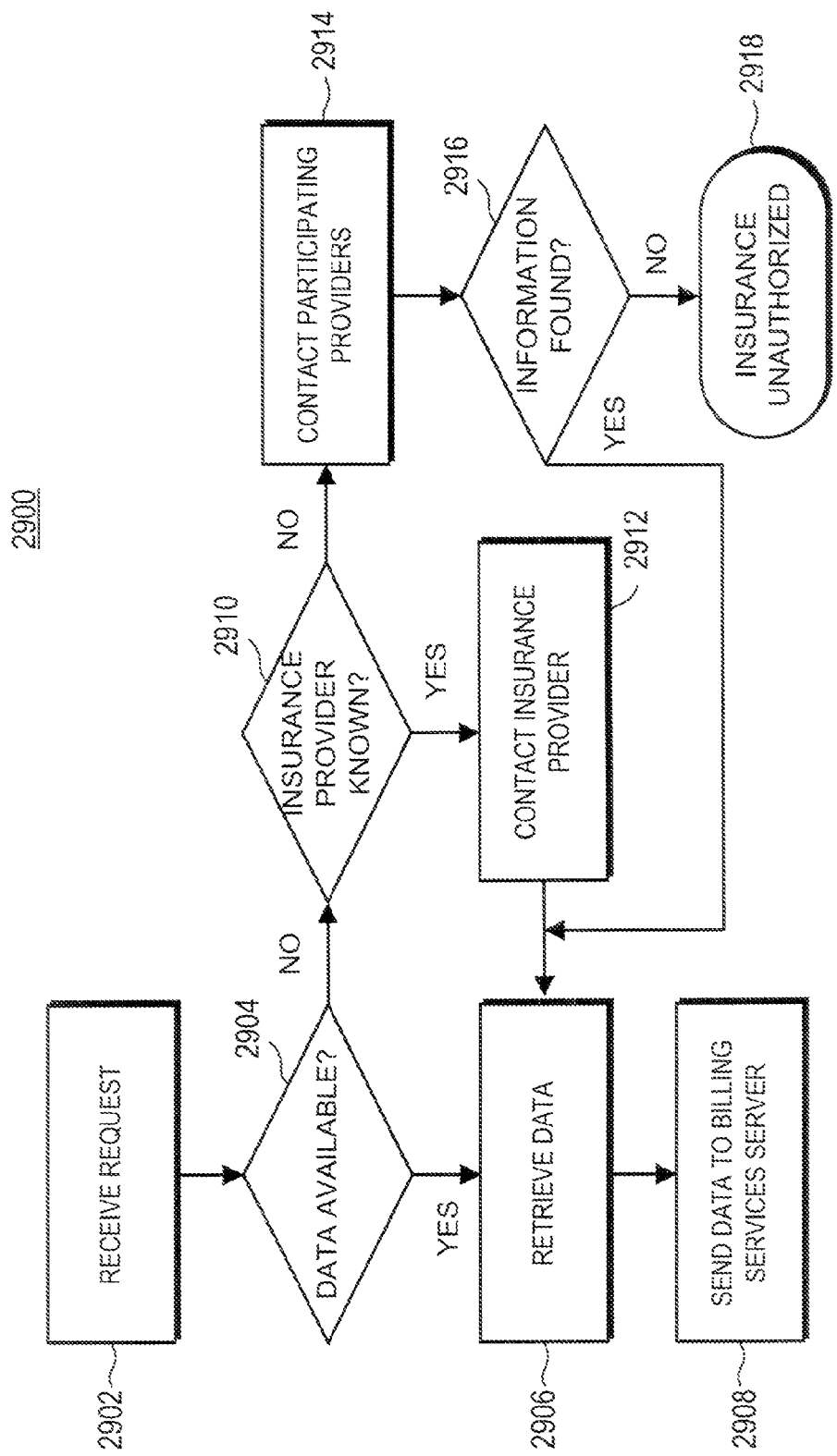
FIG. 29 is a flowchart illustrating one embodiment of a process for accessing patient insurance information.

FIG. 29 is a flowchart illustrating one embodiment of a process 2900 for retrieving and reporting patient insurance information. The request retrieval module 2802 receives 2902 a request for insurance information from an insurance provider service. A determination 2904 is made as to whether the insurance information is locally available in the insurance information database 2806 of the third party link module 126. If the data is locally available (2904-Yes), the insurance data is retrieved 2906 and sent 2908 to the billing services server for further processing. For example, if a patient visits a provider for a routine check-up, a request is sent via the provider interface device 120 to the insurance links server 340 to determine the patient's co-payment. If the co-payment information is available in the insurance information database 2806, that information is then sent to the billing services server 350 to update the patient's records and invoice accordingly.

If the data is not locally available in the insurance information database 2806 (2904-No), a determination is made as to whether the patient's insurance provider is known. If the insurance provider is known (2910-Yes) (i.e. the provider has provided the name of the insurance carrier with the request for information), the insurance provider is contacted 2912 by the communicator module 2808, which then retrieves 2906 the necessary insurance information and sends 2908 the information to the billing services server 350. If the insurance provider is not known (2910-No) (i.e. the provider has not provided the name of the insurance carrier with the request for information), the communicator module 2808 of the insurance links server 340 contacts participating insurance carriers to locate the patient's information. If the information is found (2916-Yes), the communicator module 2808 retrieves 2906 the necessary insurance information and sends 2908 the information to the billing services server 350. If the information is not found (2916-No) in any of the contacted providers, an error message is sent to the provider interface device 120 with a notification that the insurance was not authorized.

Figure 30:
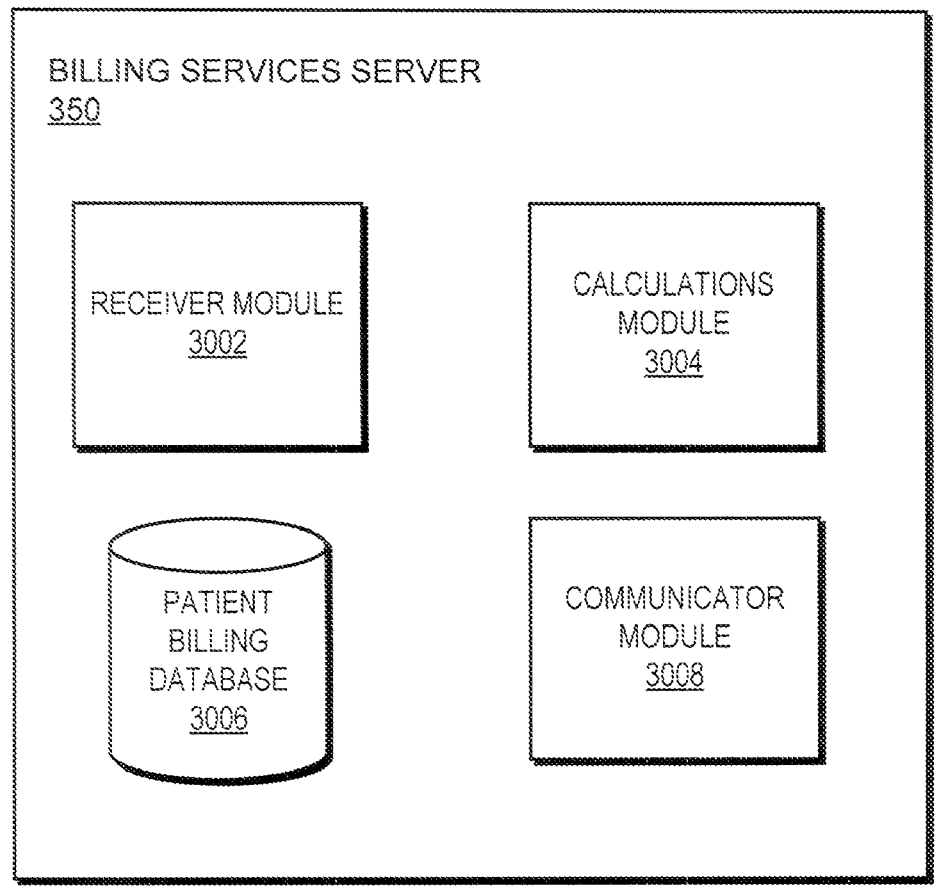
FIG. 30 is a block diagram illustrating an embodiment of a billing services server.

FIG. 30 is a block diagram illustrating an embodiment of a billing services server 350. The billing services server 350 includes a receiver module 3002, a calculations module 3004, a patient billing database 3006 and a communicator module 3008. The billing services server 350 works in cooperation with the insurance link sever 340 to update patient billing information.

Figure 31:
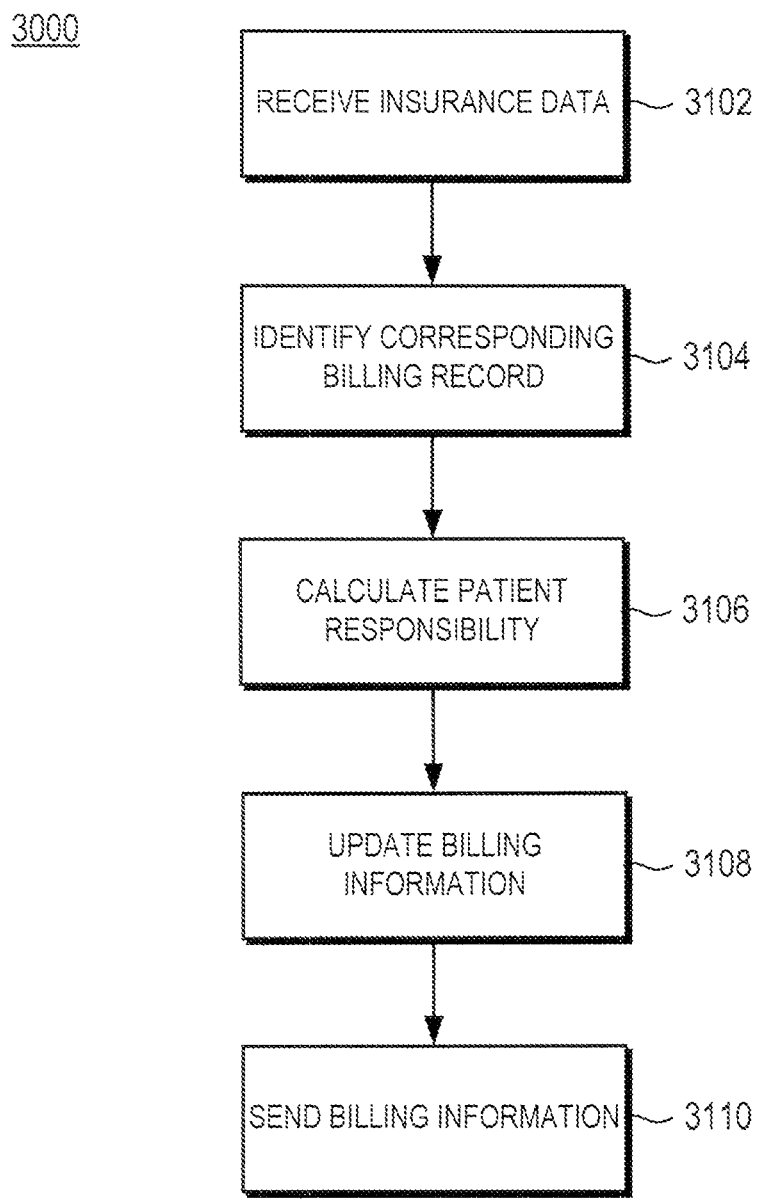
FIG. 31 is a flowchart illustrating one embodiment of a process for updating and reporting patient billing information.

FIG. 31 is a flowchart illustrating one embodiment of a process for updating and reporting patient billing information. The receiver module 3002 receives 3102 insurance data from the insurance links server 340. The corresponding patient billing record is identified 3104 within the patient billing database 3006. The calculations module 3004 calculates 3106 the patient's financial responsibility based on the received insurance information and billing information in the patient billing database 3006 and updates 3108 the patient's statement accordingly. In one embodiment, the updated billing information is stored in the patient billing database 3006. In another embodiment, the updated billing information is sent 3110 by the communicator module 3008 to be stored in the profile information of a patient's PDK.

Figure 32:
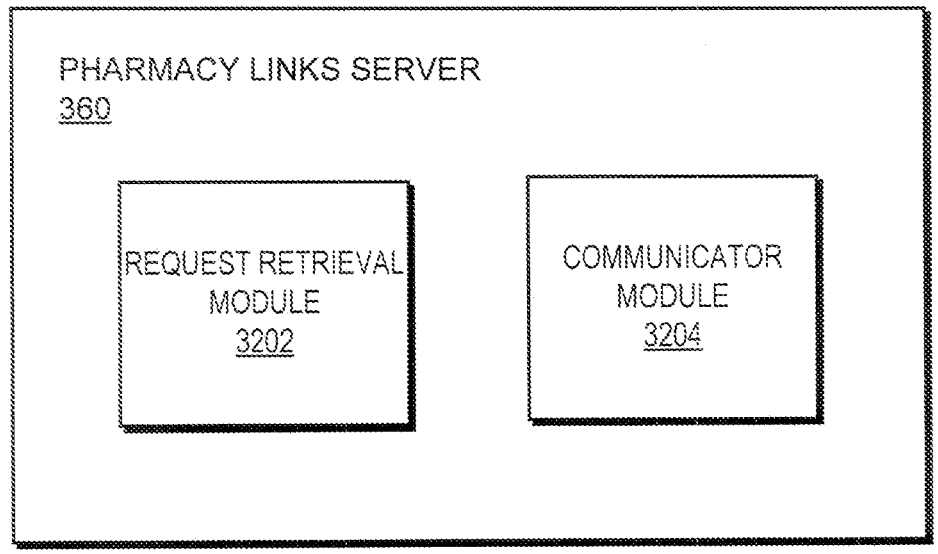
FIG. 32 is a block diagram illustrating an embodiment of a pharmacy links server.

FIG. 32 is a block diagram illustrating an embodiment of a pharmacy links server 360. The pharmacy links server 360 provides a portal of communication between health care providers and patients pharmacies, such as the pharmacy server 142 of the third party site 140 (FIG. 1). The pharmacy links server 360 therefore enables fast and effective filling out of patients' prescriptions. The pharmacy links server 360 includes a request retrieval module 3202 and a communicator module 3204.

Figure 33:
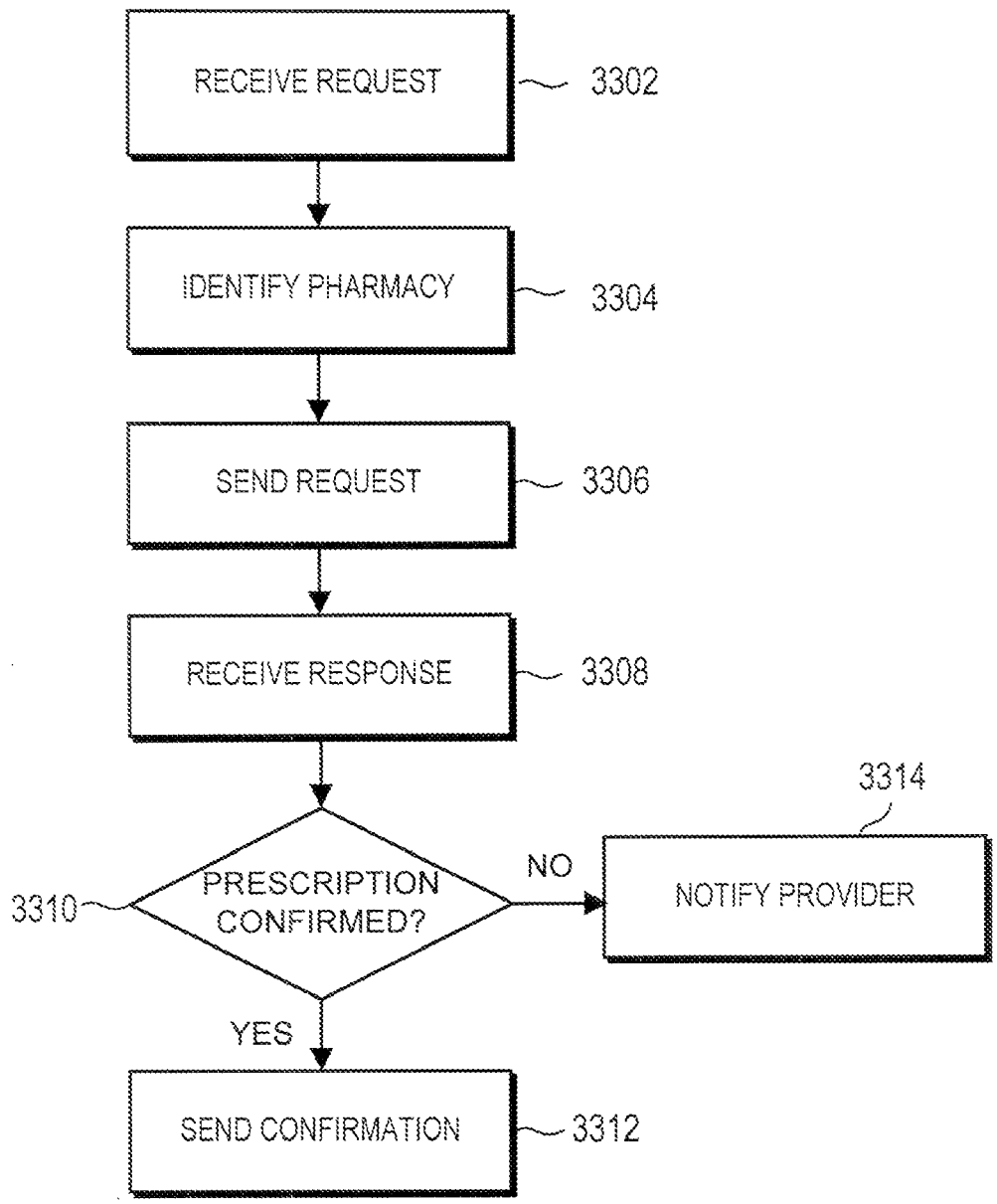
FIG. 33 is a flowchart illustrating one embodiment of a process for enabling communication with a remote pharmacy.

FIG. 33 is a flowchart illustrating one embodiment of a process 3300 for enabling communication with a remote pharmacy. The request retrieval module 3202 of the pharmacy links server 360 receives 3302 a request to fill out or re-fill a prescription for a patient. The communicator module 3204 identifies 3304 the appropriate pharmacy and sends 3306 a request for a prescription to the identified pharmacy. In one embodiment, once the request is received, a response is sent by the pharmacy and received 3308 by the communicator module 3204. In one embodiment, the response contains information as whether the prescription request was successful. If the prescription was confirmed (3310-Yes), a confirmation is sent 3312 to the provider interface device 120. If the prescription was not confirmed, for example, if the medication is not available or if the pharmacy needs more information, a notification is sent 3314 to the provider interface device 120 indicating the failure to fill out the prescription.

Figure 34:
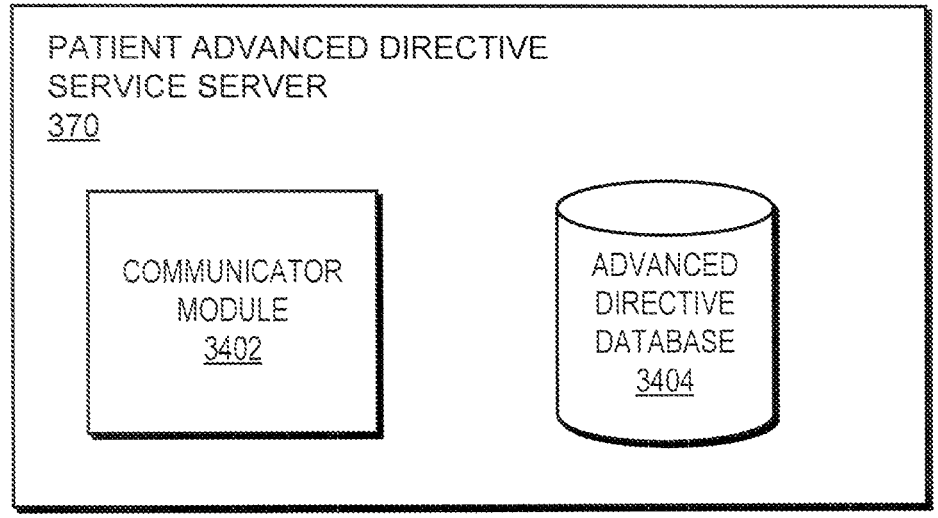
FIG. 34 is a block diagram illustrating an embodiment of a patient's advanced directive services server.

FIG. 34 is a block diagram illustrating an embodiment of a patient advanced directive services server 350. The patient advanced directive services server 350 provides storage for and secure access to a patient's advanced directive. The patient advanced directive services server 350 includes a communicator module 3402 and an advanced directive database 3404. The advanced directive database 3404 is a secure database that allows only authorized access.

Figure 35:
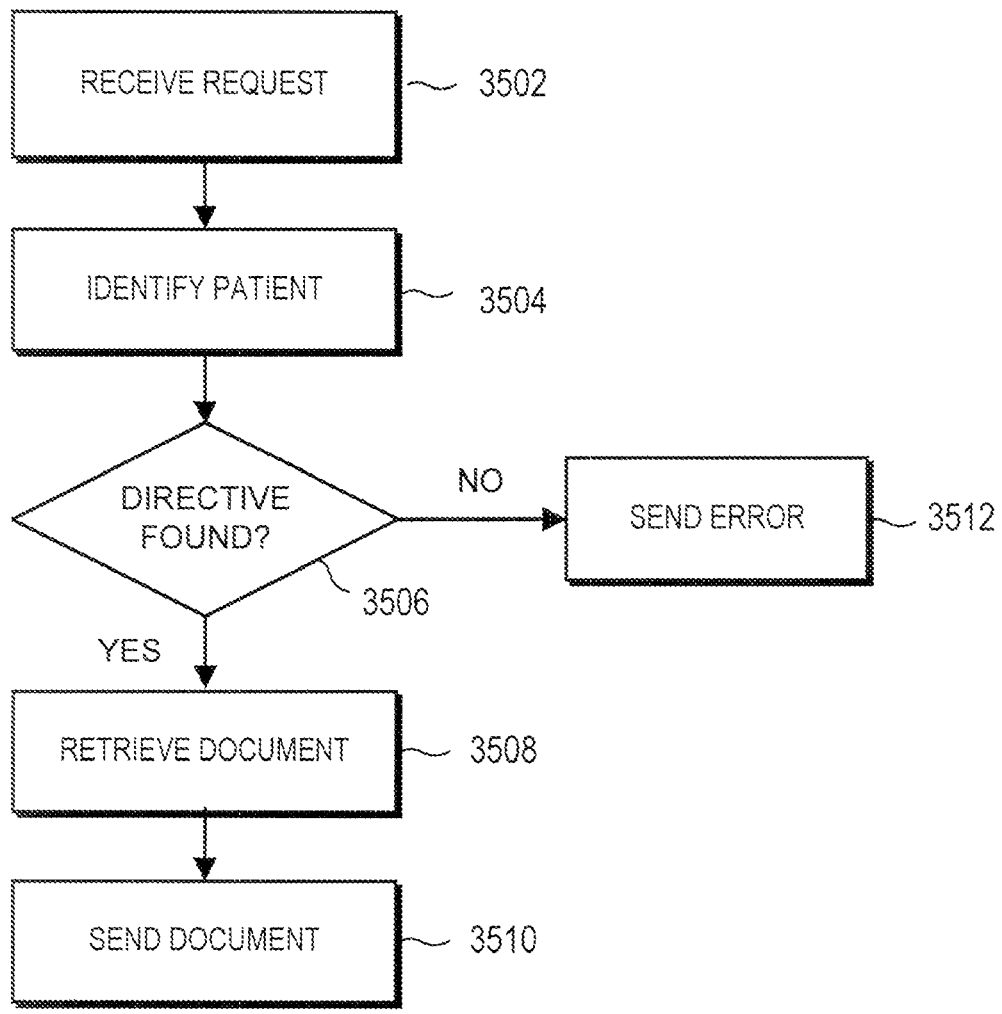
FIG. 35 is a flowchart illustrating one embodiment of a process for securely retrieving patient advanced directives.

FIG. 35 is a flowchart illustrating one embodiment of a process for securely retrieving patient advanced directives. The patient's advanced directive service server 350 receives 3502 a request for a patient's advanced directive. The patient is identified 3504 and a search is performed in the advanced directive database 3704. If the patients advanced is found (3506-Yes), the document is retrieved 350 and sent 3510 to the requestor. If the patients advanced is not found (3506-No), an error message is sent 3512 notifying the requester that the advanced directive does not exist for the patient.

Figure 36:
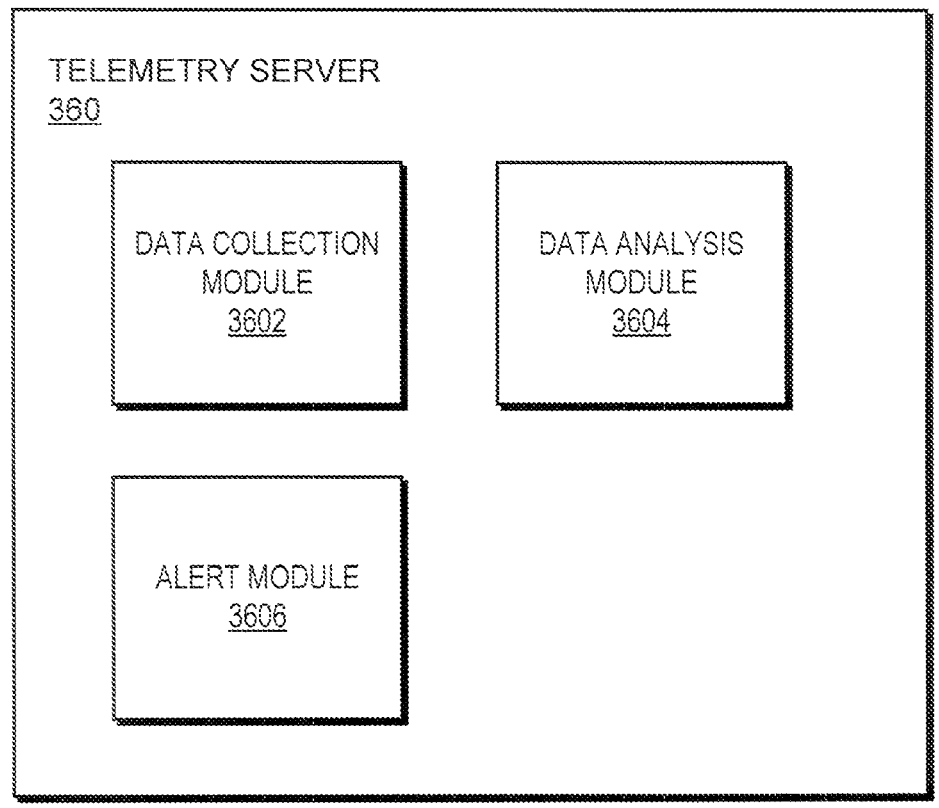
FIG. 36 is a block diagram illustrating an embodiment a telemetry server.

FIG. 36 is a block diagram illustrating an embodiment a telemetry server 260. The telemetry server 260 provides automatic updates and alerts for monitored patients presently located in a healthcare facility. The telemetry server 260 includes a data collection module 3602, a data analysis module 3604 and an alert module 3606. The data collection module 3602 is configured to receive patient status data from readers 108 located throughout the healthcare facility and is coupled to the data analysis module 3604, which is further coupled to the alert module 3606. The data analysis module 3604 receives the patient status data from the data collection module 3602 and processes the data to determine whether notifications should be sent. The alert module 3606 receives information from and sends it to one or more PDK 102 and/or provider interface devices 120.

In one embodiment, a telemetry monitor (not shown) continuously monitors a patient's status. In such embodiments, the PDK 102 is configured to wirelessly communicate with the telemetry monitor, which sends information to the PDK 102 to therefore be sent to the telemetry server 260. In another embodiment, the telemetry monitor is integrated into the PDK 102. In yet another embodiment, the telemetry monitor is configured to wirelessly communication with the Reader 108 or reader 720 of the provider interface device 120. In some embodiments, the telemetry monitor is integrated into the Reader 108 or the reader 720 of the provider interface device 120.

In one embodiment, automatic updates and alerts are available for monitored patients presently located in a healthcare facility. In such embodiments, Readers 108 automatically scans every monitored patient at regular intervals. The monitor data is compared to suggested normal data for each patient and when problems are detected, immediate alerts are issued to the appropriate individuals or areas within the healthcare facility. The monitored data is also automatically collected and stored.

Figure 37:
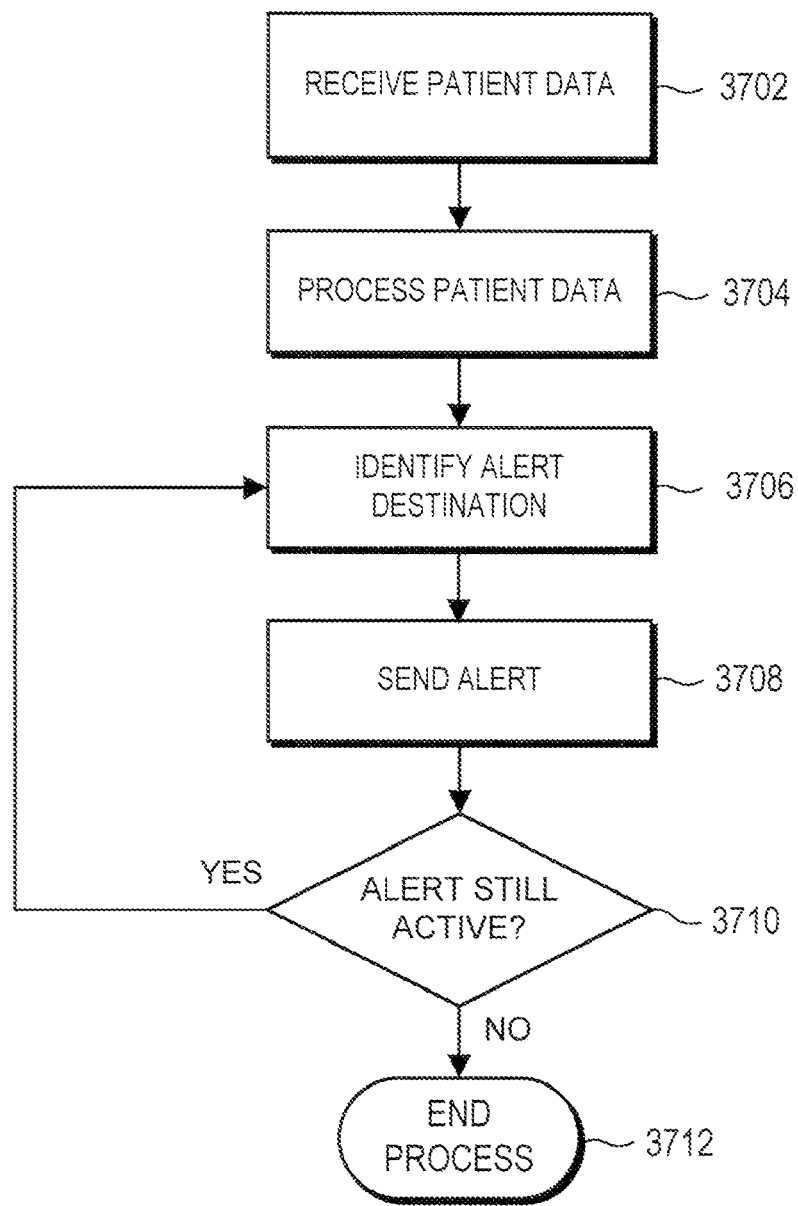
FIG. 37 is a flowchart illustrating one embodiment of a process for providing automatic updates and alerts for monitored patients.

FIG. 37 is a flowchart illustrating one embodiment of a process 3700 for providing automatic updates and alerts for monitored patients. The data collection module 3602 is receives 3702 patient status data from readers 108 located throughout the healthcare facility. The data analysis module 3604 receives the patient status data from the data collection module 3602 and processes 3704 the data to determine whether notifications should be sent. The alert module 3606 receives information from identifies 3706 the alert destination and sends 3708 it to the identified alert destination. A determination 3710 is made as to whether the alert is still active. If the alert is not active (3710-No) (i.e. there has been a response to the patient or the alert was deactivated at the alert destination), the process ends 3712. If the alert is still active (i.e. there has been no response to the patient or the alert was not deactivated at the alert destination) (3710-Yes), another alert destination is identified 3706 and the process repeats until the alert is no longer active. In one embodiment, if the alert is still active, the alert destination is broadened, for example, to be distributed to a wider area of coverage.

For example, a patient in the Intensive Care Unit (ICU) is continuously monitored to ensure a stable health status. If the electrocardiogram (EKG) machine detects that the patient's heart activity is abnormal, an alert is sent to the nurse's station. If a nurse sees the alert and responds to the patient, the nurse can deactivate the alert and the notification process ends. However, if no one is at the nurse's station, and the alert remains activated, another alert is sent to the PDK 102 of the patient's doctor. Further, if the patient's doctor does not respond and deactivate the alert, the alert may be broadened to be broadcasted to an entire unit, department, wing, floor or facility. In some embodiments, the alerts are continuously sent until a provider or other healthcare provider responds to the patient or deactivates the alert. In other embodiments, the patient can be monitored whether or not the patient is currently in their hospital room.

The order in which the steps of the methods of the present invention are performed is purely illustrative in nature. The steps can be performed in any order or in parallel, unless otherwise indicated by the present disclosure. The methods of the present invention may be performed in hardware, firmware, software, or any combination thereof operating on a single computer or multiple computers of any type. Software embodying the present invention may comprise computer instructions in any form (e.g., source code, object code, interpreted code, etc.) stored in any computer-readable storage medium (e.g., a ROM, a RAM, a magnetic media, a compact disc, a DVD, etc.). Such software may also be in the form of an electrical data signal embodied in a carrier wave propagating on a conductive medium or in the form of light pulses that propagate through an optical fiber.

While particular embodiments of the present invention have been shown and described, it will be apparent to those skilled in the art that changes and modifications may be made without departing from this invention in its broader aspect.

In the above description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to an apparatus for performing the operations herein. This apparatus can be specially constructed for the required purposes, or it can comprise a general-purpose computer selectively activated or reconfigured by a computer program stored in the computer. Such a computer program can be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and modules presented herein are not inherently related to any particular computer or other apparatus. Various general-purpose systems can be used with programs in accordance with the teachings herein, or it may prove convenient to construct more specialized apparatuses to perform the method steps. The required structure for a variety of these systems will appear from the description below. In addition, the present invention is not described with reference to any particular programming language. It will be appreciated that a variety of programming languages can be used to implement the teachings of the invention as described herein. Furthermore, as will be apparent to one of ordinary skill in the relevant art, the modules, features, attributes, methodologies, and other aspects of the invention can be implemented as software, hardware, firmware or any combination of the three. Of course, wherever a component of the present invention is implemented as software, the component can be implemented as a standalone program, as part of a larger program, as a plurality of separate programs, as a statically or dynamically linked library, as a kernel loadable module, as a device driver, and/or in every and any other way known now or in the future to those of skill in the art of computer programming. Additionally, the present invention is in no way limited to implementation in any specific operating system or environment.

It will be understood by those skilled in the relevant art that the above-described implementations are merely exemplary, and many changes can be made without departing from the true spirit and scope of the present invention.

What is claimed is:

1. A healthcare management system with automatic access to information, comprising:
    a first personal digital key (PDK) configured to wirelessly communicate with a reader within a proximity zone of the reader, wherein the first PDK includes a first profile uniquely associated with a first user, wherein the first user is a healthcare provider;
    a provider interface coupled to the reader, wherein the reader is further configured to differentiate between multiple PDKs including the first PDK and a second PDK within the proximity zone, select a PDK based on accumulated PDK data and receive profile information from the selected PDK, wherein the second PDK includes a second profile uniquely associated with a second user and the accumulated PDK data is accumulated in the reader a predetermined time after the selected PDK enters the proximity zone of the reader; and
    an auto login server configured to communicate with the provider interface to allow access, while the first PDK is within the proximity zone, to information in a patient database based on the profile information received from the first PDK-when the first PDK is the selected PDK.

2. The system of claim 1, wherein the auto login server further comprises:
    a biometric authentication module to perform biometric authentication based on the received profile information.

3. The system of claim 1, wherein the reader further comprises:
    a biometric reader configured to obtain a representation of physical or behavioral characteristics derived from the healthcare provider.

4. The system of claim 3, wherein the biometric reader is at least one of a fingerprint scanner, a retinal scanner, an iris scanner, a face scanner, a palm scanner, a DNA analyzer, a signature analyzer, and a voice analyzer.

5. The system of claim 1, wherein the first PDK further comprises:
    a biometric reader configured to obtain a representation of physical or behavioral characteristics derived from the healthcare provider.

6. The system of claim 5, wherein the biometric reader is at least one of a fingerprint scanner, a retinal scanner, an iris scanner, a face scanner, a palm scanner, a DNA analyzer, a signature analyzer, and a voice analyzer.

7. The system of claim 1, wherein the auto login server further comprises an access module for comparing the profile information received from the first PDK with data stored in a credentials database.

8. The system of claim 1, wherein the reader is further adapted to detect the first PDK in response to the first PDK entering the proximity zone of the reader, and request that the first PDK transmit the profile information.

9. The system of claim 1 wherein the auto login server further comprises a data retrieval module for retrieving data from the second PDK.

10. A method for automatic access to information in a healthcare management system, the method comprising:
    establishing a wireless connection between a reader and both a first personal digital key (PDK) and a second PDK within a proximity zone of the reader,
    wherein the first PDK includes a first profile uniquely associated with a first user and the second PDK includes a second profile uniquely associated with a second user, wherein the first user is a healthcare provider;
    differentiating between multiple PDKs within the proximity zone, the multiple PDKs including the first PDK and the second PDK;
    accumulating PDK data in the reader a predetermined time after the selected PDK enters the proximity zone of the reader;
    selecting the first PDK based on the accumulated PDK data;
    receiving profile information from the first PDK; and
    allowing access, while the first PDK is within the proximity zone, to a patient database based on the received profile information from the first PDK.

11. The method of claim 10, further comprising:
    performing biometric authentication based on the received profile information from the first PDK.

12. The method of claim 10, further comprising:
obtaining a representation of physical or behavioral characteristics derived from the healthcare provider.

13. The method of claim 12, wherein the physical or behavioral characteristics is received from at least one of a fingerprint scanner, a retinal scanner, an iris scanner, a face scanner, a palm scanner, a DNA analyzer, a signature analyzer, and a voice analyzer.

14. The method of claim 10, further comprising:
comparing the received profile information from the first PDK with data stored in a credentials database.

15. The method of claim 10, further comprising:
detecting the first PDK in response to the first PDK entering the proximity zone of the reader, and requesting that the first PDK transmit the profile information.

16. The method of claim 10 further comprising receiving data from the second PDK.

17. The method of claim 16 wherein the data received from the second PDK is associated with the first PDK.

* * * * *